US009353178B2

(12) United States Patent
Lukacs et al.

(10) Patent No.: US 9,353,178 B2
(45) Date of Patent: May 31, 2016

(54) STEM CELL FACTOR INHIBITOR

(71) Applicant: The Regents of the University of Michigan, Ann Arbor, MI (US)

(72) Inventors: Nicholas W. Lukacs, Brighton, MI (US); Vladislav A. Dolgachev, Ann Arbor, MI (US); Steven L. Kunkel, Ann Arbor, MI (US); Cory M. Hogaboam, Ann Arbor, MI (US); Sem H. Phan, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 13/937,852

(22) Filed: Jul. 9, 2013

(65) Prior Publication Data
US 2014/0023651 A1 Jan. 23, 2014

Related U.S. Application Data

(62) Division of application No. 13/347,459, filed on Jan. 10, 2012, now Pat. No. 8,911,729.

(60) Provisional application No. 61/431,246, filed on Jan. 10, 2011.

(51) Int. Cl.
*C07K 16/00* (2006.01)
*C07K 16/24* (2006.01)
*C07K 16/22* (2006.01)
*A61K 39/00* (2006.01)

(52) U.S. Cl.
CPC ................ *C07K 16/24* (2013.01); *C07K 16/22* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 4,946,778 A | 8/1990 | Ladner | |
| 5,225,539 A | 7/1993 | Winter | |
| 5,641,870 A | 6/1997 | Rinderknecht | |
| 5,731,168 A | 3/1998 | Carter | |
| 5,885,962 A * | 3/1999 | Lu ................................. | 514/7.9 |
| 6,207,417 B1 * | 3/2001 | Zsebo et al. ................... | 435/69.5 |
| 6,506,559 B1 | 1/2003 | Fire | |
| 7,144,731 B2 | 12/2006 | Zsebo et al. | |
| 7,285,640 B2 * | 10/2007 | Takeuchi et al. ............... | 530/387.1 |
| 7,582,297 B2 | 9/2009 | Reed | |
| 7,893,036 B2 | 2/2011 | Zamore | |
| 8,278,067 B2 | 10/2012 | Longley | |
| 2003/0194405 A1 | 10/2003 | Takeuchi et al. | |
| 2005/0112698 A1 | 5/2005 | Neben | |
| 2005/0136057 A1 | 6/2005 | Sato et al. | |
| 2005/0282233 A1 | 12/2005 | Eriksson et al. | |
| 2007/0253951 A1 | 11/2007 | Ng et al. | |
| 2008/0025958 A1 | 1/2008 | Hannon | |
| 2008/0200420 A1 | 8/2008 | Zamore | |
| 2008/0247951 A1 | 10/2008 | Koch et al. | |
| 2008/0269147 A1 | 10/2008 | Tuschl | |
| 2009/0123974 A1 | 5/2009 | Gantier et al. | |
| 2010/0305003 A1 | 12/2010 | Tang | |

FOREIGN PATENT DOCUMENTS

| | | |
|---|---|---|
| EP | 125023 | 11/1984 |
| EP | 171496 | 2/1986 |
| EP | 173494 | 3/1986 |
| EP | 184187 | 6/1986 |
| EP | 0676470 A1 | 10/1995 |
| WO | 8702671 | 5/1987 |
| WO | 8601533 | 3/1989 |
| WO | 03070966 A2 | 8/2003 |
| WO | 2005038054 A1 | 4/2005 |
| WO | 2005054270 | 6/2005 |
| WO | 2006066048 | 6/2006 |
| WO | 2008006369 | 1/2008 |
| WO | 2008043753 | 4/2008 |
| WO | 2008051306 | 5/2008 |
| WO | 2009117769 A1 | 10/2009 |
| WO | 2011016238 A1 | 2/2011 |

OTHER PUBLICATIONS

Powell et al., "Epithelial cells and their neighbors I. Role of intestinal myofibroblasts in development, repair, and cancer." Am J Physiol Gastrointest Liver Physiol. Jul. 2005; 289(1):G2-7.
Powell et al., "Myofibroblasts. II. Intestinal subepithelial myofibroblasts." Am J Physiol. Aug. 1999; 277(2 Pt 1): C183-201.
Remington's pharmaceutical sciences, 17th ed. Edited by Alfonso R. Gennaro. Mack Publishing Co., 20th and Northampton Streets, Easton, PA 18042. 1985.
S.P.C. Cole, D. Kozbor and J.C. Roder. "The EBV-hybridoma technique and its application to human lung cancer." In, Monoclonal Antibodies and Cancer Therapy (vol. 27, UCLA Symposia on Molecular and Cellular Biology, New Series) (eds. R.A. Reisfeld and S.Sell), pp. 77-96, Alan R. Liss, Inc. N.Y., 1985.
Sastry et al., "Cloning of the immunological repertoire in *Escherichia coli* for generation of monoclonal catalytic antibodies: construction of a heavy chain variable region-specific cDNA library." Proc Natl Acad Sci U S A. Aug. 1989; 86(15):5728-32.
Schubert et al., "Local RNA target structure influences siRNA efficacy: systematic analysis of intentionally designed binding regions." J Mol Biol. May 13, 2005;348(4):883-93.
Shalaby et al., "Development of humanized bispecific antibodies reactive with cytotoxic lymphocytes and tumor cells overexpressing the HER2 protooncogene." J Exp Med. Jan. 1, 1992;175(1):217-25.
Shaw et al., "Mouse/human chimeric antibodies to a tumor-associated antigen: biologic activity of the four human IgG subclasses." J Natl Cancer Inst. Dec. 7, 1988;80(19):1553-9.

(Continued)

*Primary Examiner* — Michail Belyavskyi
(74) *Attorney, Agent, or Firm* — Casimir Jones S.C.; David Casimir; Thomas Isenbarger

(57) ABSTRACT

Provided herein are methods, compositions, and uses relating to inhibitors of stem cell factor. For example, provided herein are antibodies targeting stem cell factor and methods for treating fibrotic and tissue remodeling diseases.

11 Claims, 7 Drawing Sheets

(56) References Cited

OTHER PUBLICATIONS

Sohail et al., "Antisense oligonucleotides selected by hybridisation to scanning arrays are effective reagents in vivo." Nucleic Acids Res. May 15, 2001;29(10):2041-51.

Stumpp & Amstutz, "DARPins: a true alternative to antibodies." Curr Opin Drug Discov Devel. Mar. 2007;10 (2):153-9.

Sun et al., "Chimeric antibody with human constant regions and mouse variable regions directed against carcinoma-associated antigen 17-1A." Proc Natl Acad Sci U S A. Jan. 1987;84(1):214-8.

Suresh et al., "Bispecific monoclonal antibodies from hybrid hybridomas." Methods Enzymol. 1986;121:210-28.

Traunecker et al., "Bispecific single chain molecules (Janusins) target cytotoxic lymphocytes on HIV infected cells." EMBO J. Dec. 1991;10(12):3655-9.

Tuschl & Borkhardt, "Small interfering RNAs: a revolutionary tool for the analysis of gene function and gene therapy." Mol Interv. Jun. 2002;2(3):158-67.

Tuschl et al., "Targeted mRNA degradation by double-stranded RNA in vitro." Genes Dev. Dec. 15, 1999;13 (24):3191-7.

Verhoeyen et al., "Reshaping human antibodies: grafting an antilysozyme activity" Science Mar. 25, 1988: 1534-1536.

Vittal et al., "Effects of the protein kinase inhibitor, imatinib mesylate, on epithelial/mesenchymal phenotypes: implications for treatment of fibrotic diseases." J Pharmacol Exp Ther. Apr. 2007; 321(1):35-44.

Vuorinen et al., "Imatinib mesylate inhibits fibrogenesis in asbestos-induced interstitial pneumonia." Exp Lung Res. Sep. 2007;33(7):357-73.

Williams et al., "Identification of a ligand for the c-kit proto-oncogene." Cell. Oct. 5, 1990; 63(1):167-74.

Wood et al., "The synthesis and in vivo assembly of functional antibodies in yeast." Nature. Apr. 4-10, 1985;314 (6010):446-9.

Zapata et al., "Engineering linear F(ab')2 fragments for efficient production in Escherichia coli and enhanced antiproliferative activity." Protein Eng. Oct. 1995;8(10):1057-62.

Zsebo et al., "Identification, purification, and biological characterization of hematopoietic stem cell factor from buffalo rat liver—conditioned medium." Cell. Oct. 5, 1990; 63(1):195-201.

Andre et al., "c-kit mRNA expression in human and murine hematopoietic cell lines." Oncogene. Aug. 1989; 4 (8):1047-9.

Aono et al., "Imatinib as a novel antifibrotic agent in bleomycin-induced pulmonary fibrosis in mice." Am J Respir Crit Care Med. Jun. 1, 2005; 171(11):1279-85.

Beidler et al., "Cloning and high level expression of a chimeric antibody with specificity for human carcinoembryonic antigen." J Immunol. Dec. 1, 1988; 141(11):4053-60.

Berlin et al., "Inhibition of SCF attenuates peribronchial remodeling in chronic cockroach allergen-induced asthma." Lab Invest. Jun. 2006;86(6):557-65.

Better et al., "Escherichia coli secretion of an active chimeric antibody fragment." nce. May 20, 1988; 240 (4855):1041-3.

Bohula et al., "The efficacy of small interfering RNAs targeted to the type 1 insulin-like growth factor receptor (IGF1R) is influenced by secondary structure in the IGF1R transcript." J Biol Chem. May 2, 2003;278(18):15991-7.

Brennan et al., "Preparation of bispecific antibodies by chemical recombination of monoclonal immunoglobulin G1 fragments." Science. Jul. 5, 1985;229(4708):81-3.

Brummelkamp et al., "A system for stable expression of short interfering RNAs in mammalian cells." Science. Apr. 19, 2002;296(5567):550-3.

Caplen et al., "Specific inhibition of gene expression by small double-stranded RNAs in invertebrate and vertebrate systems." Proc Natl Acad Sci U S A. Aug. 14, 2001;98(17):9742-7.

Clackson et al., "Making antibody fragments using phage display libraries." Nature. Aug. 15, 1991; 352 (6336):624-8.

Coloma et al., "Primer design for the cloning of immunoglobulin heavy-chain leader-variable regions from mouse hybridoma cells using the PCR." Biotechniques. Aug. 1991;11(2):152-4, 156.

Distler et al., "Imatinib mesylate reduces production of extracellular matrix and prevents development of experimental dermal fibrosis." Arthritis Rheum. Jan. 2007; 56(1):311-22.

Dolgachev et al., "Role of Stem Cell factor and bone marrow-derived fibroblasts in airway remodeling." Am. J. Pathol 2009, 174(2):390-400.

El Kossi et al., "Stem cell factor and crescentic glomerulonephritis." Am J Kidney Dis. Apr. 2003; 41(4):785-95.

Elbashir et al., "Duplexes of 21-nucleotide RNAs mediate RNA interference in cultured mammalian cells." Nature. May 24, 2001;411(6836):494-8.

Elbashir et al., "Functional anatomy of siRNAs for mediating efficient RNAi in Drosophila melanogaster embryo lysate." Embo J. Dec. 3, 2001;20(23):6877-88.

Elbashir et al., "RNA interference is mediated by 21- and 22-nucleotide RNAs." Genes Dev. Jan. 15, 2001;15 (2):188-200.

El-Koraie et al., "Role of stem cell factor and mast cells in the progression of chronic glomerulonephritides." Kidney Int. Jul. 2001; 60(1):167-72.

GenBank Accession No. NG_012098, Homo sapiens KIT ligand (KITLG), RefSeqGene on chromosome 12.

GenBank Accession No. NM_000899, Homo sapiens KIT ligand (KITLG), transcript variant b, Mrna.

GenBank Accession No. NM_003994, Homo sapiens KIT ligand (KITLG), transcript variant a, Mrna.

GenBank Accession No. NP_000890, kit ligand isoform b precursor [Homo sapiens].

GenBank Accession No. NP_003985, kit ligand isoform a precursor [Homo sapiens].

GenBank Direct Submission. B61190 titled "mast cell growth factor, short form precursor-human" (PRI Jul. 21, 2000) <http://www.ncbi.nlm.nih.gov/protein/B61190?report=genpept./.

Goding, Monoclonal Antibodies: Principles and Practice, Academic Press, 1986.

Gruber et al., "Efficient tumor cell lysis mediated by a bispecific single chain antibody expressed in Escherichia coli." J Immunol. Jun. 1, 1994;152(11):5368-74.

Harlow & Lane, "Antibodies: A Laboratory Manual" Copld Spring Harbor Laboratory Press, Cold Spring Harbor, NY, 1988.

Holen et al., "Positional effects of short interfering RNAs targeting the human coagulation trigger Tissue Factor." Nucleic Acids Res. Apr. 15, 2002;30(8):1757-66.

Huang et al., "The hematopoietic growth factor KL is encoded by the Sl locus and is the ligand of the c-kit receptor, the gene product of the W locus." Cell. Oct. 5, 1990;63(1):225-33.

Huse et al., "Generation of a large combinatorial library of the immunoglobulin repertoire in phage lambda." Science. Dec. 8, 1989;246(4935):1275-81.

Jones et al., "Replacing the complementarity-determining regions in a human antibody with those from a mouse." Nature. May 29-Jun. 4, 1986; 321(6069):522-5.

Kohler et al., "Continuous cultures of fused cells secreting antibody of predefined specificity." Nature. Aug. 7, 1975;256(5517):495-7.

Kostelny et al., "Formation of a bispecific antibody by the use of leucine zippers." J Immunol. Mar. 1, 1992;148 (5):1547-53.

Kozbor et al., "The Production of Monoclonal Antibodies from Human lymphocytes." Immunology Today. 1983, 4:72-79.

Kretschmer-Kazemi & Sczakiel, "The activity of siRNA in mammalian cells is related to structural target accessibility: a comparison with antisense oligonucleotides." Nucleic Acids Res. Aug. 1, 2003;31(15):4417-24.

Larrick et al., :PCR Amplification of Antibody Genes. Methods: Companion to Methods in Enzymology 1991, 2:106.

Liu et al., "Chimeric mouse-human IgG1 antibody that can mediate lysis of cancer cells." Proc Natl Acad Sci U S A. May 1987;84(10):3439-43.

Liu et al., "Production of a mouse-human chimeric monoclonal antibody to CD20 with potent Fc-dependent biologic activity." J Immunol. Nov. 15, 1987;139(10):3521-6.

Marks et al., "By-passing immunization. Human antibodies from V-gene libraries displayed on phage." J Mol Biol. Dec. 5, 1991;222(3):581-97.

(56) References Cited

OTHER PUBLICATIONS

Martin et al., "Primary structure and functional expression of rat and human stem cell factor DNAs." Cell. Oct. 5, 1990; 63(1):203-11.

McCafferty et al., "Phage antibodies: filamentous phage displaying antibody variable domains." Nature. Dec. 6, 1990; 348(6301):552-4.

Milstein et al., "Hybrid hybridomas and their use in immunohistochemistry." Nature. Oct. 6-12, 1983;305 (5934):537-40.

Morimoto et al., "Single-step purification of F(ab')2 fragments of mouse monoclonal antibodies (immunoglobulins G1) by hydrophobic interaction high performance liquid chromatography using TSKgel Phenyl-5PW." vol. 24, Issues 1-2, 1992, pp. 107-117.

Morrison, "Transfectomas provide novel chimeric antibodies." Science. Sep. 20, 1985;229(4719):1202-7.

Nishimura et al., "Recombinant human-mouse chimeric monoclonal antibody specific for common acute lymphocytic leukemia antigen." Cancer Res. Feb. 15, 1987;47(4):999-1005.

Oi et al., "Chimeric Antibodies." BioTechniques 1986, 4:214.

Orlandi et al., "Cloning immunoglobulin variable domains for expression by the polymerase chain reaction." Proc Natl Acad Sci U S A. May 1989;86(10):3833-7.

Orr-Urtreger et al., "Developmental expression of c-kit, a proto-oncogene encoded by the W locus." Development. Aug. 1990; 109(4):911-23.

Overhoff et al., "Local RNA target structure influences siRNA efficacy: a systematic global analysis." J Mol Biol. May 13, 2005;348(4):871-81.

Pluckthun, "Antibodies from *Escherichia coli*." in The Phamacology of Monoclonal Antibodies, M. Rosenberg and G.P. Moore Eds., (Springer Verlag, Berlin 1994), 113:269-315.

GenBank Accession No. CAH18078, published Oct. 7, 2008, Retrived Oct. 21, 2015, 2 page.

GenBank Accession No. AF400436_1, published Aug. 21, 2001, Retrived Oct. 21, 2015, 1 page.

International Preliminary Report on Patentability, PCT/US2012/020782, Mailed Jul. 6, 2012, 12 pages.

International Preliminary Report on Patentability, PCT/US2014/046138, Mailed Dec. 15, 2014, 18 pages.

Gagari et al., "Expression of stem cell factor and its receptor, c-kit, in human oral mesenchymal cells." Eur J Oral Sci. Oct. 2006;114(5):409-15.

* cited by examiner

The amino acid sequence of an immunogenic peptide used to produce antibodies specific for SCF (SEQ ID NO: 1)

Ser Ser Ser Asn Arg Lys Ala Lys Asn Pro Pro Gly Asp Ser Cys

The nucleotide sequence corresponding to the amino acid sequence of SEQ ID NO: 1 (SEQ ID NO: 2)

TCG TCG TCG AAC CGC AAA GCG AAA AAC CCG CCG GGC GAT TCG TGC
Ser Ser Ser Asn Arg Lys Ala Lys Asn Pro Pro Gly Asp Ser Cys

STEM CELL FACTOR INHIBITOR

This application is a divisional of U.S. patent application Ser. No. 13/347,459, filed on Jan. 10, 2012, which claims priority to U.S. Patent Application Ser. No. 61/431,246 filed on Jan. 10, 2011, which is incorporated herein by reference in its entirety for all purposes.

STATEMENT REGARDING FEDERALLY SPONSORED RESEARCH OR DEVELOPMENT

This invention was made with government support under HL059178 awarded by the National Institutes of Health. The government has certain rights in the invention.

FIELD OF INVENTION

Provided herein are methods, compositions, and uses relating to inhibitors of stem cell factor. For example, provided herein are antibodies targeting stem cell factor and methods for treating fibrotic and tissue remodeling diseases.

BACKGROUND

Diseases involving tissue remodeling and fibrosis are a leading cause of death worldwide. Nearly 45 percent of all natural deaths in the western world are attributable to some type of chronic fibroproliferative disease and the associated health care costs are in the billions of dollars. Tissue remodeling is the reorganization or renovation of existing tissues, which can either change the characteristics of a tissue (e.g., blood vessel remodeling) or participate in establishing the dynamic equilibrium of a tissue (e.g., bone remodeling). Fibrosis is the formation or development of excess fibrous connective tissue in an organ or tissue as a reparative or reactive process, as opposed to formation of fibrous tissue as a normal constituent of an organ or tissue. Fibrosis affects nearly all tissues and organ systems, and fibrotic tissue remodeling can influence cancer metastasis and accelerate chronic graft rejection in transplant recipients. Diseases in which fibrosis is a major cause of morbidity and mortality include the interstitial lung diseases, liver cirrhosis, kidney disease, heart disease, and systemic sclerosis, among others.

Stem cell factor (SCF) and its receptor c-Kit have been implicated in fibrotic and tissue remodeling diseases (El-Koraie, et al., Kidney Int. 60: 167 (2001); Powell, et al., Am. J. Physiol. 289: G2 (2005); El Kossi, et al., Am. J. Kidney Dis. 41: 785 (2003); Powell, et al., Am. J. Physiol. 277: C183 (1999)). c-Kit is a type III receptor-tyrosine kinase that is present in many cell types (Orr-Urtreger et al., Development 109: 911 (1990)). It is also expressed in the early stages of differentiation (Andre et al., Oncogene 4: 1047 (1989)) and certain tumors exhibit elevated expression of c-kit. SCF is a ligand specific for the c-Kit receptor kinase. Binding causes dimerization of c-Kit and activation of its kinase activity. SCF was first isolated from the supernatant of murine fibroblasts. At the time, SCF was called mast cell growth factor (MGF) (Williams et al., Cell 63: 167 (1990)) or hematopoietic growth factor KL (Kit ligand) (Huang et al., Cell 63: 225 (1990)). A homologue was subsequently isolated from rat liver cells and designated stem cell factor (SCF) (Zsebo et al., Cell 63: 195 (1990)). The corresponding human protein is designated variously as SCF, MGF, or Steel Factor (SF) (Cell 63: 203 (1990)).

Previous studies have suggested that an inhibitor of c-Kit receptor tyrosine kinase can significantly inhibit aberrant tissue fibrosis (see, e.g., Aono, Am. J. Respir. Crit. Care Med. 171: 1279 (2005); Vuorinen, et al., Exp. Lung Res. 33: 357 (2007); Vittal, et al., J. Pharmacol. Exp. Ther. 321:35 (2007); Distler, et al., Arthritis Rheum 56: 311 (2007)). However, this inhibitor has several disadvantages. It needs to be given systemically by oral administration, it has some toxicity associated with its use, and the compound must be delivered intracellularly for efficacy. Consequently, alternative therapies are needed.

SUMMARY

Provided herein are methods, compositions, and uses relating to inhibitors of stem cell factor. For example, provided herein are antibodies targeting stem cell factor and methods for treating fibrotic and tissue remodeling diseases as well as for research and diagnostic uses.

In some embodiments, the compositions, methods, and uses herein provide therapies relating to inhibiting stem cell factor (SCF). Some embodiments provide an isolated antibody that targets SCF. In some embodiments, inhibiting SCF affects the activity of c-Kit. The compositions, methods, and uses provided herein find use in treating fibrotic diseases and maladies associated with tissue remodeling. Unlike some other therapies that produce undesirable side effects due to interfering with general intracellular signaling pathways, the embodiments provided herein eliminate or minimize such side effects by modulating the activity of SCF. Consequently, toxicity is minimized. Moreover, targeting an extracellular ligand removes the need to deliver a composition into a cell to interact with an intracellular target. In some embodiments, the compositions are delivered into the airway, thus providing an advantage over previous technologies that require oral administration and, as such, resulting in systemic bioavailability.

Provided herein are embodiments of methods for treating a fibrotic or tissue remodeling disease comprising administering a therapeutically effective amount of a stem cell factor inhibitor to a subject with or at risk for a fibrotic or tissue remodeling disease. For example, in some embodiments, provided herein are methods comprising providing an inhibitor of stem cell factor and administering a therapeutically effective amount of the inhibitor to a subject. In some embodiments the inhibitor is an isolated antibody (e.g., a monoclonal or polyclonal antibody) or an antigen-binding fragment thereof (e.g., Fab, Fab', F(ab')$_2$, and Fv fragments, etc.). In some embodiments the inhibitor is a small interfering RNA. In more specific embodiments, the antibody is a monoclonal antibody or a polyclonal antibody. Some embodiments provide that the antibody or antigen-binding fragment thereof specifically binds to stem cell factor. Some embodiments provide that the antibody or antigen-binding fragment thereof specifically binds to a peptide comprising amino acid sequence SEQ ID NO: 1 or SEQ ID NO: 8.

In some embodiments of the methods provided herein, the subject has a disease. Accordingly, some embodiments provide that administering the inhibitor prevents or reduces the severity of at least one sign or symptom of the disease. In some embodiments, the subject has an abnormal activity of stem cell factor or the subject has abnormal collagen production. In some embodiments, the subject has a disease including, but not limited to, fibrosis or a remodeling disease. In additional embodiments, the disease is a pulmonary disease. Some embodiments provide that a subject has a pulmonary disease including, but not limited to, idiopathic pulmonary fibrosis, chronic obstructive pulmonary disease, acute respiratory distress syndrome, cystic fibrosis, peribronchial fibrosis, hypersensitivity pneumonitis, or asthma. In addition, some embodiments provide that a subject has a disease including, but not limited to, sclerodoma, inflammation, liver cirrhosis, renal fibrosis, parenchymal fibrosis, endomyocardial fibrosis, mediatinal fibrosis, nodular subepidermal fibrosis, fibrous histiocytoma, fibrothorax, hepatic fibrosis, fibromyalgia, gingival fibrosis, or radiation-induced fibrosis.

While not limited in the mode of administration, in some embodiments of the method, the antibody is delivered into an airway of the subject, e.g., by intranasal administration.

In some embodiments, administering the inhibitor reduces the activity of a receptor. Some embodiments provide that administering the inhibitor reduces an interaction of stem cell factor with a receptor. In more specific embodiments, the receptor is a receptor tyrosine kinase, and in yet more specific embodiments, the receptor is c-Kit. Importantly, the methods are not limited in the location of the targeted receptor or the origin of stem cell factor. For example, in some embodiments the receptor is found on a hematopoietic progenitor cell, a melanocyte, a germ cell, an eosinophil, a lymphocyte, a fibroblast, a myofibroblast, or a mast cell. Additionally, in some embodiments, stem cell factor originates from a bone marrow cell, a liver cell, an epithelial cell, a smooth muscle cell, or a fibroblast. In some embodiments, administering the inhibitor to a subject results in a direct inhibition of fibroblast activation.

Some embodiments provide a composition comprising an isolated antibody (e.g., a monoclonal or a polyclonal antibody) or antigen-binding fragment thereof that specifically binds to stem cell factor (e.g., a protein or a peptide fragment thereof (e.g., an epitope)). For example, some embodiments provide a composition comprising an isolated antibody or antigen-binding fragment thereof that specifically binds to a peptide of amino acid sequence SEQ ID NO: 1 or SEQ ID NO: 8. Additional embodiments provide an antibody or antigen-binding fragment than binds to the SCF isoform b precursor (e.g., a protein or peptide fragment of the sequence available at GenBank accession number NP_000890 (SEQ ID NO: 4)), or a variant or modified form thereof, or to the SCF isoform a precursor (e.g., a protein or peptide fragment of the sequence available at GenBank accession number NP_003985 (SEQ ID NO: 6)), or a variant or modified form thereof. Some embodiments provide an antibody or antigen-binding fragment that binds to a protein or peptide, or variants or modified forms thereof, that is a translation product of the NCBI Reference Gene Sequence for SCF (e.g., accession number NG_012098 (SEQ ID NO: 7)) or variants or fragments thereof. Some embodiments provide an antibody or antigen-binding fragment that binds to a peptide comprising the first 11 amino acids of the mature form of SCF (e.g., EGICRNRVTNN (SEQ ID NO: 8)).

Some embodiments provide an antibody or antigen-binding fragment than binds to the translation product (e.g., a protein or peptide), or a variant or modified form thereof, of a nucleic acid encoding SCF, or a variant or a modified form thereof. For example, embodiments provide an antibody or antigen-binding fragment than binds to the translation product (e.g., a protein or peptide), or a variant or modified form thereof, of the nucleic acids having sequences comprising a sequence as defined by GenBank accession numbers NM_000899 (SEQ ID NO: 3), NM_003994 (SEQ ID NO: 5), and NG_012098 (SEQ ID NO: 7), or fragments or variants thereof (e.g., mutants, cDNAs, expression-optimized variants, operably linked to a regulatory element (e.g., promoter, enhancer, polymerase binding site, etc.), etc.). In some embodiments, the antibody or antigen-binding fragment binds to a protein or peptide, or a variant or modified form thereof, that is the translation product of a nucleotide sequence that encodes the peptide sequence EGICRNRVTNN (SEQ ID NO: 8). The peptides and proteins (and fragments and variants thereof) and the nucleic acids (and fragments and variants thereof) that encode the peptides and proteins (and fragments and variants thereof) are used in some embodiments to raise antibodies. Also contemplated are vectors, plasmids, expression constructs, cells, cell lines, hybridomas, and organisms used to produce the antibodies as provided herein.

Some embodiments provide a monoclonal antibody and some embodiments provide a humanized antibody. In some embodiments, the composition is used for a medicament or is used for the manufacture of a medicament. In some embodiments, the medicament is used to treat disease. Use of the composition as a medicament is not limited in the disease that can be treated. For example, in some embodiments, the disease is idiopathic pulmonary fibrosis, chronic obstructive pulmonary disease, acute respiratory distress syndrome, cystic fibrosis, peribronchial fibrosis, hypersensitivity pneumonitis, asthma, sclerodoma, inflammation, liver cirrhosis, renal fibrosis, parenchymal fibrosis, endomyocardial fibrosis, mediatinal fibrosis, nodular subepidermal fibrosis, fibrous histiocytoma, fibrothorax, hepatic fibrosis, fibromyalgia, gingival fibrosis, or radiation-induced fibrosis. In some embodiments, the composition is used to study disease in vitro or in a model system (e.g., in vivo).

Embodiments provide herein a method of preparing an antibody (e.g., a monoclonal antibody) targeting stem cell factor comprising the steps of providing a peptide comprising or consisting of an immunogenic portion of SCF (e.g., as provided by SEQ ID NO: 1 or 8), immunizing a host with the peptide, isolating an immune cell from the host, preparing a hybridoma using the immune cell, and isolating the antibody or antigen-binding fragment thereof. Some embodiments provide a method of preparing an antibody (e.g., a monoclonal antibody) targeting stem cell factor, wherein the antibody or antigen-binding fragment thereof specifically binds to stem cell factor (e.g., a protein or a peptide fragment thereof (e.g., an epitope)). For example, some embodiments provide a method of preparing an isolated antibody or antigen-binding fragment thereof that specifically binds to a peptide of amino acid sequence SEQ ID NO: 1. Additional embodiments provide a method of preparing an antibody or antigen-binding fragment than binds to the SCF isoform b precursor (e.g., a protein or peptide fragment of the sequence available at GenBank accession number NP_000890 (SEQ ID NO: 4)), or a variant or modified form thereof, or to the SCF isoform a precursor (e.g., a protein or peptide fragment of the sequence available at GenBank accession number NP_003985 (SEQ ID NO: 6)), or a variant or modified form thereof. Some embodiments provide a method of preparing an antibody or antigen-binding fragment that binds to a protein or peptide, or variants or modified forms thereof, that is a translation product of the NCBI Reference Gene Sequence for SCF (e.g., accession number NG_012098 (SEQ ID NO: 7)) or variants or fragments thereof. Some embodiments provide a method of preparing an antibody or antigen-binding fragment that binds to a peptide comprising the first 11 amino acids of the mature form of SCF (e.g., EGICRNRVTNN (SEQ ID NO: 8)).

Some embodiments provide a method of preparing an antibody or antigen-binding fragment than binds to the translation product (e.g., a protein or peptide), or a variant or modified form thereof, of a nucleic acid encoding SCF, or a variant or a modified form thereof. For example, embodiments provide a method of preparing an antibody or antigen-binding fragment than binds to the translation product (e.g., a protein or peptide), or a variant or modified form thereof, of the nucleic acids having sequences comprising a sequence as defined by GenBank accession numbers NM_000899 (SEQ ID NO: 3), NM_003994 (SEQ ID NO: 5), and NG_012098 (SEQ ID NO: 7), or fragments or variants thereof (e.g., mutants, cDNAs, expression-optimized variants, operably linked to a regulatory element (e.g., promoter, enhancer, polymerase binding site, etc.), etc.). In some embodiments, the antibody or antigen-binding fragment binds to a protein or peptide, or a variant or modified form thereof, that is the translation product of a nucleotide sequence that encodes the peptide sequence EGICRNRVTNN (SEQ ID NO: 8). The peptides, proteins, and fragments and variants thereof and nucleic acids, and fragments and variants thereof, that encode the peptides, proteins, and fragments and variants thereof, find use in some embodiments in a method of preparing antibodies as provided by the technology provided. Also contemplated are methods of producing vectors, plasmids, expression constructs, cells, cell lines, hybridomas, and organisms that find use in producing the antibodies as provided herein.

Some embodiments provide a method comprising the steps of providing an inhibitor of stem cell factor and administering the inhibitor to a cell or tissue.

In addition, some embodiments provide a kit comprising a composition comprising an isolated antibody or antigen-binding fragment thereof that specifically binds to stem cell factor, a means for administering the composition to a subject, and/or instructions for use.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 1A shows a plot demonstrating that an anti-SCF antibody reduces the amount of hydroxyproline in bleomycin treated lung; FIG. 1B shows a plot demonstrating that an anti-SCF antibody reduces the amount of IL-25 mRNA; FIG. 1C shows a plot demonstrating that an anti-SCF antibody reduces the amount of IL-13 mRNA; FIG. 1D shows a plot demonstrating that an anti-SCF antibody reduces the amount of soluble SCF present in plasma. FIG. 1E shows a plot demonstrating that an anti-SCF antibody reduces the amount of IL-25 receptor.

FIG. 3 shows an amino acid sequence and the corresponding nucleotide sequence of an immunogenic peptide used to produce antibodies specific for SCF.

DETAILED DESCRIPTION

Figure 1:
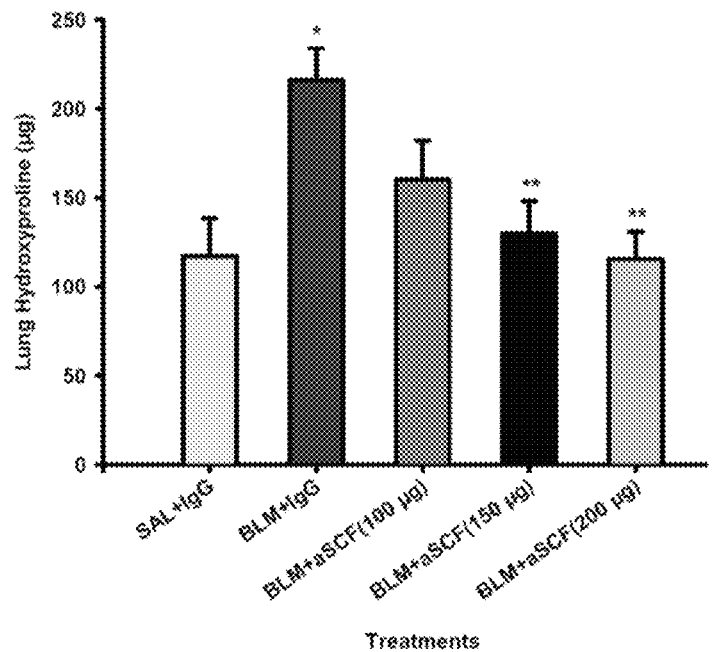
FIG. 1 shows a series of plots demonstrating that inhibiting SCF with an antibody reduces the expression of tissue remodeling mediators.
Figure 1:
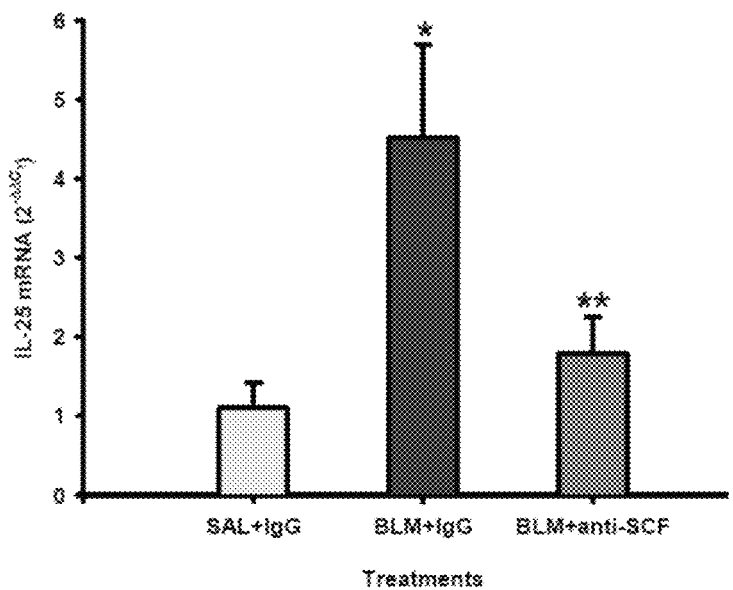
Figure 1:
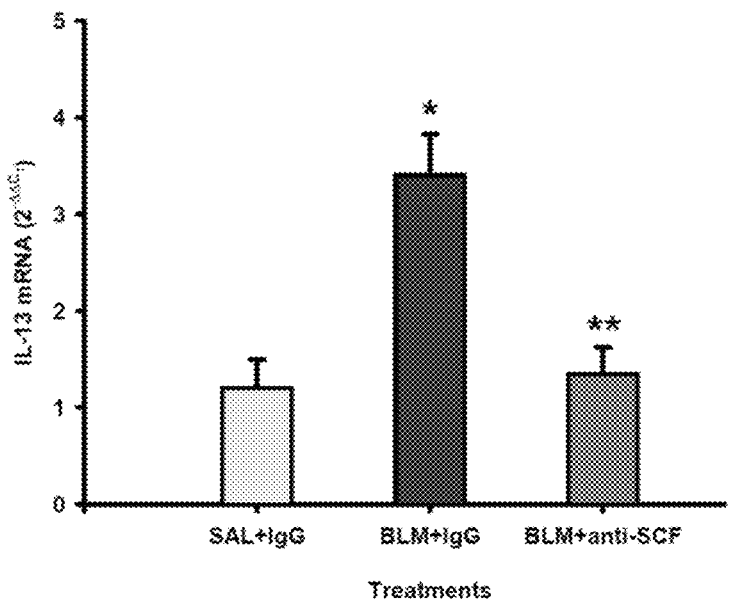
Figure 1:
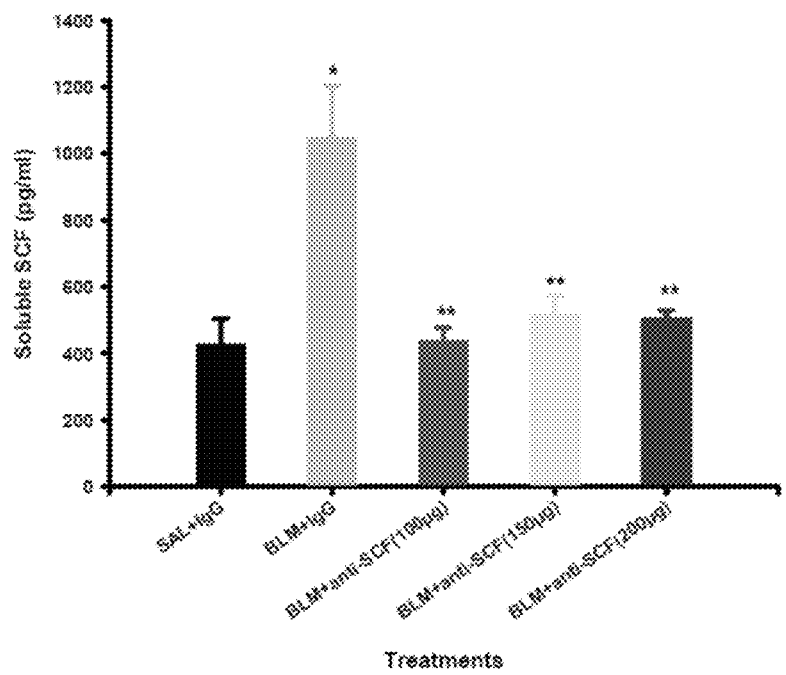
Figure 1:
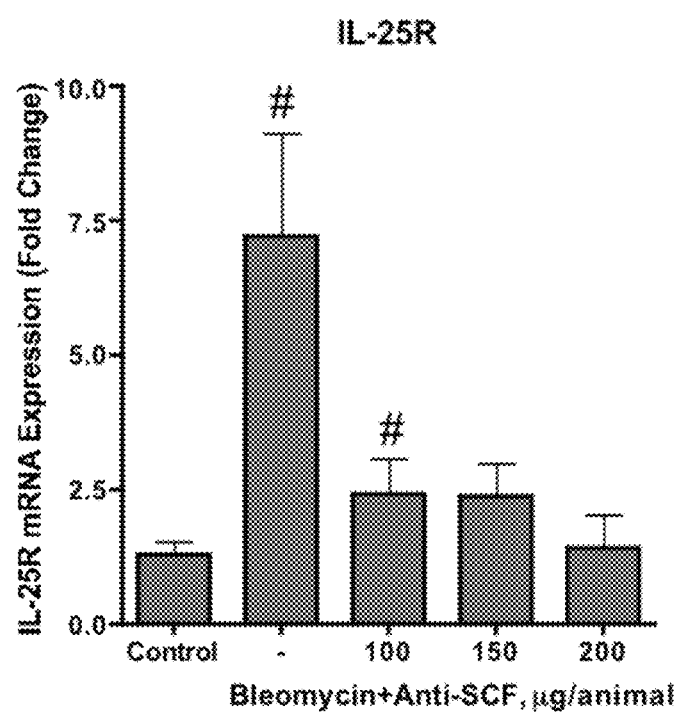

Provided herein are methods, compositions, and uses relating to inhibitors of stem cell factor. For example, provided herein are antibodies targeting stem cell factor, methods of producing antibodies targeting stem cell factor, and methods for treating fibrotic and tissue remodeling diseases as well as for research and diagnostic uses. In some embodiments, the compositions, methods, and uses herein provide therapies relating to inhibiting stem cell factor (SCF). Some embodiments provide an isolated antibody that targets SCF. In some embodiments, inhibiting SCF affects the activity of c-Kit. The compositions, methods, and uses provided herein find use in treating fibrotic diseases and maladies associated with tissue remodeling.

Definitions

To facilitate an understanding of embodiments of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein.

The term "nascent" when used in reference to a protein refers to a newly synthesized protein, which has not been subject to post-translational modifications, which includes but is not limited to glycosylation and polypeptide shortening. The term "mature" when used in reference to a protein refers to a protein which has been subject to post-translational processing and/or which is in a cellular location (such as within a membrane or a multi-molecular complex) from which it can perform a particular function which it could not if it were not in the location.

The term "portion" when used in reference to a protein (as in "a portion of a given protein") refers to fragments of that protein. The fragments may range in size from four amino acid residues to the entire amino sequence minus one amino acid (for example, the range in size includes 4, 5, 6, 7, 8, 9, 10, or 11 . . . amino acids up to the entire amino acid sequence minus one amino acid).

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "domain" when used in reference to a polypeptide refers to a subsection of the polypeptide which possesses a unique structural and/or functional characteristic; typically, this characteristic is similar across diverse polypeptides. The subsection typically comprises contiguous amino acids, although it may also comprise amino acids which act in concert or which are in close proximity due to folding or other configurations. Examples of a protein domain include the transmembrane domains, and the glycosylation sites.

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

The terms "oligonucleotide" or "polynucleotide" or "nucleotide" or "nucleic acid" refer to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The terms "an oligonucleotide having a nucleotide sequence encoding a gene" or "a nucleic acid sequence encoding" a specified polypeptide refer to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (i.e., a sequence of nucleotides) related by the base-pairing rules. For example, for the sequence "5'-A-G-T-3'," is complementary to the sequence "3'-T-C-A-5'."

Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is frequently that gene which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "allele" refers to different variations in a gene; the variations include but are not limited to variants and mutants, polymorphic loci and single nucleotide polymorphic loci, frameshift and splice mutations. An allele may occur naturally in a population, or it might arise during the lifetime of any particular individual of the population.

Thus, the terms "variant" and "mutant" when used in reference to a nucleotide sequence refer to an nucleic acid sequence that differs by one or more nucleotides from another, usually related nucleotide acid sequence. A "variation" is a difference between two different nucleotide sequences; typically, one sequence is a reference sequence.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (e.g., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

The term "purified" refers to molecules, either nucleic or amino acid sequences, that are removed from their natural environment, isolated or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "composition comprising" a given polynucleotide sequence or polypeptide refers broadly to any composition containing the given polynucleotide sequence or polypeptide. The composition may comprise an aqueous solution. Compositions comprising polynucleotide sequences or fragments thereof may be employed as hybridization probes. In some embodiments, polynucleotide sequences are employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

As used herein, the term "antibody" is used in its broadest sense to refer to whole antibodies, monoclonal antibodies (including human, humanized, or chimeric antibodies), polyclonal antibodies, and antibody fragments that can bind antigen (e.g., Fab', F'(ab)$_2$, Fv, single chain antibodies), comprising complementarity determining regions (CDRs) of the foregoing as long as they exhibit the desired biological activity.

As used herein, "antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); single-chain antibody molecules; and multispecific antibodies formed from antibody fragments.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

As used herein, "active" or "activity" refers to native or naturally occurring biological and/or immunological activity.

As used herein the term, "in vitro" refers to an artificial environment and to processes or reactions that occur within an artificial environment. In vitro environments may include, but are not limited to, test tubes and cell cultures. The term "in vivo" refers to the natural environment (e.g., an animal or a cell) and to processes or reactions that occur within a natural environment.

As used herein, "inhibitor" refers to a molecule which eliminates, minimizes, or decreases the activity, e.g., the biological, enzymatic, chemical, or immunological activity, of a target.

As used herein the term "disease" refers to a deviation from the condition regarded as normal or average for members of a species, and which is detrimental to an affected individual under conditions that are not inimical to the majority of individuals of that species (e.g., diarrhea, nausea, fever, pain, inflammation, etc.).

As used herein, the term "administration" refers to the act of giving a drug, prodrug, antibody, or other agent, or therapeutic treatment to a physiological system (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like. "Coadministration" refers to administration of more than one chemical agent or therapeutic treatment (e.g., radiation therapy) to a physiological system (e.g., a subject or in vivo, in vitro, or ex vivo cells, tissues, and organs). As used herein, administration "in combination with" one or more further therapeutic agents includes simultaneous (concurrent) and consecutive administration in any order. "Coadministration" of therapeutic treatments may be concurrent, or in any temporal order or physical combination.

As used herein, the term "treating" includes reducing or alleviating at least one adverse effect or symptom of a disease or disorder through introducing in any way a therapeutic composition of the present technology into or onto the body of a subject. "Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

As used herein, "therapeutically effective dose" refers to an amount of a therapeutic agent sufficient to bring about a beneficial or desired clinical effect. Said dose can be administered in one or more administrations. However, the precise determination of what would be considered an effective dose may be based on factors individual to each patient, including, but not limited to, the patient's age, size, type or extent of disease, stage of the disease, route of administration, the type or extent of supplemental therapy used, ongoing disease process, and type of treatment desired (e.g., aggressive vs. conventional treatment).

As used herein, the term "effective amount" refers to the amount of a composition sufficient to effect beneficial or desired results. An effective amount can be administered in one or more administrations, applications, or dosages and is not intended to be limited to a particular formulation or administration route.

As used herein, the term "pharmaceutical composition" refers to the combination of an active agent with, as desired, a carrier, inert or active, making the composition especially suitable for diagnostic or therapeutic use in vitro, in vivo, or ex vivo.

As used herein, the terms "pharmaceutically acceptable" or "pharmacologically acceptable" refer to compositions that do not substantially produce adverse reactions, e.g., toxic, allergic, or immunological reactions, when administered to a subject.

As used herein, "carriers" include pharmaceutically acceptable carriers, excipients, or stabilizers which are nontoxic to the cell or mammal being exposed thereto at the dosages and concentrations employed. Often the physiologically acceptable carrier is an aqueous pH-buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants.

As used herein, the terms "patient" or "subject" refer to organisms to be treated by the compositions of the present technology or to be subject to various tests provided by the technology. The term "subject" includes animals, preferably mammals, including humans. In a preferred embodiment, the subject is a primate. In an even more preferred embodiment, the subject is a human.

As used herein, the term "sample" is used in its broadest sense. In one sense it can refer to animal cells or tissues. In another sense, it is meant to include a specimen or culture obtained from any source, such as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present technology.

Embodiments of the Technology

Although the disclosure herein refers to certain illustrated embodiments, it is to be understood that these embodiments are presented by way of example and not by way of limitation.

1. Inhibitors of SCF

Stem cell factor (SCF) is a ligand that is specific for the c-Kit receptor kinase. Binding of SCF to c-Kit causes dimerization of c-Kit and activation of its kinase activity, which is important for hemopoiesis, melanogenesis, and fertility. Through c-Kit, SCF acts to promote cell survival, proliferation, differentiation, adhesion, and functional activation. Aberrant activation of c-Kit can result in disease, including fibrosis and tissue remodeling defects. In particular, there are multiple pulmonary diseases with known remodeling defects as well as other chronic tissue remodeling diseases affecting other organs and tissues. Specific examples of diseases involving fibrosis or tissue remodeling defects are idiopathic pulmonary fibrosis, chronic obstructive pulmonary disease, acute respiratory distress syndrome, cystic fibrosis, peribronchial fibrosis, hypersensitivity pneumonitis, asthma, scleroderma, inflammation, liver cirrhosis, renal fibrosis, parenchymal fibrosis, endomyocardial fibrosis, mediatinal fibrosis, nodular subepidermal fibrosis, fibrous histiocytoma, fibrothorax, hepatic fibrosis, fibromyalgia, gingival fibrosis, and radiation-induced fibrosis.

Accordingly, interfering with the interaction between SCF and c-Kit can be used to treat or study diseases involving aberrant activation of c-Kit that causes fibrosis and tissue remodeling defects. The c-Kit receptor is found on hematopoietic progenitor cells, melanocytes, germ cells, eosinophils, lymphocytes, and mast cells. Thus, preventing SCF interaction with c-Kit can alter the activation of several disease-associated cell populations that have been implicated in fibrosis and tissue remodeling disease phenotypes.

Additionally, SCF induces key mediators in the fibrotic response, IL-25 and IL-13. Data suggest that IL-25 can drive IL-13 expression in a T-cell and antigen-independent manner. Therefore, these processes can progress without an antigen-specific response and consequently chronically perpetuate remodeling and fibrotic disease. It is contemplated that a complex cascade is established in which SCF induces IL-25, which in turn induces production of IL-13, myofibroblast differentiation, and collagen production. IL-4 has also been identified as a fibrosis-associated cytokine.

2. Antibodies

In some embodiments, inhibiting the ability of SCF to interact with c-Kit is accomplished by means of an antibody that recognizes SCF. The antibody can be a monoclonal antibody or a polyclonal antibody, and may be, for example, a human, humanized, or chimeric antibody. Monoclonal antibodies against target antigens are produced by a variety of techniques including conventional monoclonal antibody methodologies such as the somatic cell hybridization techniques of Köhler and Milstein (Nature, 256:495 (1975)). Although in some embodiments, somatic cell hybridization procedures are preferred, other techniques for producing monoclonal antibodies are contemplated as well (e.g., viral or oncogenic transformation of B lymphocytes).

It is contemplated that antibodies against SCF find use in the experimental, diagnostic, and therapeutic methods described herein. In certain embodiments, the antibodies provided herein are used to detect the expression of SCF in biological samples. For example, a sample comprising a tissue biopsy can be sectioned and protein detected using, for example, immunofluorescence or immunohistochemistry. Alternatively, individual cells from a sample can be isolated, and protein expression detected on fixed or live cells by FACS analysis. Furthermore, the antibodies can be used on protein arrays to detect expression of SCF. In other embodiments, the antibodies provided herein are used to decrease the activity of cells expressing c-Kit by inhibiting SCF either in an in vitro cell-based assay or in an in vivo animal model. In some embodiments, antibodies are used to treat a human patient by administering a therapeutically effective amount of an antibody against SCF.

For the production of antibodies, various host animals can be immunized by injection with the peptide corresponding to the desired epitope (e.g., a fragment of SCF, e.g., a fragment comprising the sequence provided by SEQ ID NO: 1 or 8 or immunogenic portions thereof) including, but not limited to, rabbits, mice, rats, sheep, goats, etc. Antibodies to SCF can be raised by immunizing (e.g., by injection) with an antigen comprising a peptide, a portion, or the full protein of the SCF isoform b precursor (e.g., a protein or peptide fragment of the sequence available at GenBank accession number NP_000890 (SEQ ID NO: 4)), or a variant or modified version thereof, or a peptide, a portion, or the full protein of the SCF isoform a precursor (e.g., a protein or peptide fragment of the sequence available at GenBank accession number NP_003985 (SEQ ID NO: 6)), or a variant or modified version thereof. Antibodies can also be raised by immunization with a translation product of the NCBI Reference Gene Sequence for SCF (e.g., accession number NG_012098 (SEQ ID NO: 7)) or variants or fragments thereof.

In some embodiments, the peptide is conjugated to an immunogenic carrier (e.g., diphtheria toxoid, bovine serum albumin (BSA), or keyhole limpet hemocyanin (KLH)). Various adjuvants are used to increase the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

Polyclonal antibodies can be prepared by any known method. Polyclonal antibodies can be raised by immunizing an animal (e.g., a rabbit, rat, mouse, donkey, etc) by multiple subcutaneous or intraperitoneal injections of the relevant antigen (a purified peptide fragment, full-length recombinant protein, fusion protein, etc.) optionally conjugated to KLH, serum albumin, etc., diluted in sterile saline, and combined with an adjuvant to form a stable emulsion. The polyclonal antibody is then recovered from blood, ascites, and the like, of an animal so immunized Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

For preparation of monoclonal antibodies, any technique that provides for the production of antibody molecules by continuous cell lines in culture may be used (see e.g., Harlow and Lane, Antibodies: A Laboratory Manual, Cold Spring Harbor Laboratory Press, Cold Spring Harbor, N.Y.). These include, but are not limited to, the hybridoma technique originally developed by Köhler and Milstein and the trioma technique, the human B-cell hybridoma technique (See, e.g., Kozbor et al., Immunol. Today, 4:72 (1983)), and the EBV-hybridoma technique to produce human monoclonal antibodies (Cole et al., in Monoclonal Antibodies and Cancer Therapy, Alan R. Liss, Inc., pp. 77-96 (1985)).

In some embodiments provided herein, the antibodies are prepared from a hybridoma. Using the hybridoma method, a mouse, hamster, or other appropriate host animal, is immunized as described above to elicit the production by lymphocytes of antibodies that will specifically bind to an immunizing antigen. Alternatively, lymphocytes can be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay such as radioimmunoassay (RIA) or enzyme-linked immunosorbent assay (ELISA) can then be propagated in vitro (e.g., in culture) using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

The preferred animal system for preparing hybridomas is the murine system. Hybridoma production in the mouse is a well-established procedure. Immunization protocols and techniques for isolation of immunized splenocytes for fusion are known in the art. Fusion partners (e.g., murine myeloma cells) and fusion procedures are also known. Embodiments of the technology herein provide antibodies (e.g., monoclonal antibodies) produced from a hybridoma prepared by immunizing mice with a peptide that is a portion or fragment of the SCF protein. For example, some embodiments provide an antibody or antigen-binding fragment than binds to SCF by immunizing with, e.g., a protein or peptide fragment of the sequence available at GenBank accession number NP_000890 (SEQ ID NO: 4)), or a variant or modified version thereof, or by immunizing with, e.g., a protein or peptide fragment of the sequence available at GenBank accession number NP_003985 (SEQ ID NO: 6)), or a variant or modified version thereof. Some embodiments provide an antibody or antigen-binding fragment that binds to a protein or peptide, or variants or modified versions thereof, that is a translation product of the NCBI Reference Gene Sequence for SCF (e.g., accession number NG_012098 (SEQ ID NO: 7)) or variants or fragments thereof.

For example, embodiments of the technology herein provide monoclonal antibodies produced from a hybridoma prepared by immunizing mice with a peptide of amino acid sequence SEQ ID NO: 1 or 8. Also contemplated are methods and compositions related to antibodies prepared using a variant of SEQ ID NO: 1 or 8 comprising one or more substitutions, deletions, insertions, or other changes, as long as said variant produces an antibody specific for SCF. Producing polypeptides of SEQ ID NO: 1 or 8 and similar sequences thereto can be accomplished according to various techniques well known in the art. For example, a polypeptide of SEQ ID NO: 1 or 8 or a variant thereof can be produced using a bacterial expression system and a nucleic acid encoding a polypeptide of SEQ ID NO: 1 or 8 or a variant thereof. As an example, a polypeptide according to SEQ ID NO: 1 can be produced using the nucleotide sequence according to SEQ ID NO: 2.

Moreover, human monoclonal antibodies directed against human proteins can be generated using transgenic mice carrying the complete human immune system rather than the mouse system. Splenocytes from the transgenic mice are immunized with the antigen of interest, which are used to produce hybridomas that secrete human monoclonal antibodies with specific affinities for epitopes from a human protein.

Monoclonal antibodies can also be generated by other methods known to those skilled in the art of recombinant DNA technology. For instance, combinatorial antibody display has can be utilized to produce monoclonal antibodies (see, e.g., Sastry et al., Proc. Nat. Acad. Sci. USA, 86: 5728 (1989); Huse et al., Science, 246: 1275 (1989); Orlandi et al., Proc. Nat. Acad. Sci. USA, 86:3833 (1989)). After immunizing an animal with an immunogen as described above, the antibody repertoire of the resulting B-cell pool is cloned. Methods are generally known for obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primers to a conserved 3' region can be used to amplify and isolate the heavy and light chain variable regions from a number of murine antibodies (see. e.g., Larrick et al., Biotechniques, 11: 152 (1991)). A similar strategy can also been used to amplify human heavy and light chain variable regions from human antibodies (see, e.g., Larrick et al., Methods: Companion to Methods in Enzymology, 2: 106 (1991)).

Alternatively, monoclonal antibodies can also be made using recombinant DNA methods as described in U.S. Pat. No. 4,816,567. The polynucleotides encoding a monoclonal antibody are isolated (e.g., from mature B-cells or hybridoma cells), by, e.g., RT-PCR using oligonucleotide primers that specifically amplify the genes encoding the heavy and light chains of the antibody, and their sequences are determined using conventional procedures. The isolated polynucleotides encoding the heavy and light chains are then cloned into suitable expression vectors, which, when transfected into host cells such as E. coli cells, simian COS cells, Chinese hamster ovary (CHO) cells, or myeloma cells that do not otherwise produce immunoglobulin protein, cause monoclonal antibodies to be generated by the host cells. Also, recombinant monoclonal antibodies or fragments thereof of the desired species can be isolated from phage display libraries as described (McCafferty et al., 1990, Nature, 348:552-

554; Clackson et al., 1991, Nature, 352:624-628; and Marks et al., 1991, J. Mol. Biol., 222:581-597).

The polynucleotide encoding a monoclonal antibody can further be modified in a number of different manners using recombinant DNA technology to generate alternative antibodies. In one embodiment, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity, affinity, etc. of a monoclonal antibody.

For example, also contemplated are chimeric mouse-human monoclonal antibodies, which can be produced by recombinant DNA techniques known in the art. For example, a gene encoding the constant region of a murine (or other species) monoclonal antibody molecule is digested with restriction enzymes to remove the region encoding the murine constant region, and the equivalent portion of a gene encoding a human constant region is substituted (see, e.g., Robinson et al., PCT/US86/02269; European Patent Application 184,187; European Patent Application 171,496; European Patent Application 173,494; WO 86/01533; U.S. Pat. No. 4,816,567; European Patent Application 125,023 (each of which is herein incorporated by reference in its entirety); Better et al., Science, 240:1041-1043 (1988); Liu et al., Proc. Nat. Acad. Sci. USA, 84:3439-3443 (1987); Liu et al., J. Immunol., 139:3521-3526 (1987); Sun et al., Proc. Nat. Acad. Sci. USA, 84:214-218 (1987); Nishimura et al., Canc. Res., 47:999-1005 (1987); Wood et al., Nature, 314:446-449 (1985); and Shaw et al., J. Natl. Cancer Inst., 80:1553-1559 (1988)).

The chimeric antibody can be further humanized by replacing sequences of the variable region that are not directly involved in antigen binding with equivalent sequences from human variable regions. General reviews of humanized chimeric antibodies are provided by S. L. Morrison, Science, 229:1202-1207 (1985) and by Oi et al., Bio Techniques, 4:214 (1986). Those methods include isolating, manipulating, and expressing the nucleic acid sequences that encode all or part of immunoglobulin variable regions from at least one of a heavy or light chain. Sources of such nucleic acid are well known to those skilled in the art. The recombinant DNA encoding the chimeric antibody, or fragment thereof, can then be cloned into an appropriate expression vector.

Suitable humanized antibodies can alternatively be produced by CDR substitution (see, e.g., U.S. Pat. No. 5,225,539; Jones et al., Nature, 321:552-525 (1986); Verhoeyan et al., Science, 239:1534 (1988); and Beidler et al., J. Immunol., 141:4053 (1988)). All of the CDRs of a particular human antibody may be replaced with at least a portion of a non-human CDR or only some of the CDRs may be replaced with non-human CDRs. It is only necessary to replace the number of CDRs important for binding of the humanized antibody to the Fc receptor.

An antibody can be humanized by any method that is capable of replacing at least a portion of a CDR of a human antibody with a CDR derived from a non-human antibody. The human CDRs may be replaced with non-human CDRs using oligonucleotide site-directed mutagenesis.

Also contemplated are chimeric and humanized antibodies in which specific amino acids have been substituted, deleted, or added. In particular, preferred humanized antibodies have amino acid substitutions in the framework region, such as to improve binding to the antigen. For example, in a humanized antibody having mouse CDRs, amino acids located in the human framework region can be replaced with the amino acids located at the corresponding positions in the mouse antibody. Such substitutions are known to improve binding of humanized antibodies to the antigen in some instances.

In certain embodiments provided herein, it is desirable to use an antibody fragment. Various techniques are known for the production of antibody fragments. Traditionally, these fragments are derived via proteolytic digestion of intact antibodies (for example Morimoto et al., 1993, Journal of Biochemical and Biophysical Methods 24:107-117 and Brennan et al., 1985, Science, 229:81). For example, papain digestion of antibodies produces two identical antigen-binding fragments, called Fab fragments, each with a single antigen-binding site, and a residual Fc fragment. Pepsin treatment yields an F(ab')$_2$ fragment that has two antigen-combining sites and is still capable of cross-linking antigen.

However, these fragments are now typically produced directly by recombinant host cells as described above. Thus Fab, Fv, and scFv antibody fragments can all be expressed in and secreted from E. coli or other host cells, thus allowing the production of large amounts of these fragments. Alternatively, such antibody fragments can be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

Fv is the minimum antibody fragment which contains a complete antigen-recognition and antigen-binding site. This region consists of a dimer of one heavy-chain and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. F(ab')$_2$ antibody fragments originally were produced as pairs of Fab' fragments which have hinge cysteines between them. Other chemical couplings of antibody fragments are also known to the skilled artisan.

The technology herein provided also contemplates modifying an antibody to increase its serum half-life. This can be achieved, for example, by incorporating a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

The technology embraces variants and equivalents which are substantially homologous to the chimeric, humanized, and human antibodies, or antibody fragments thereof, provided herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid, or one neutral amino acid by another neutral amino acid. What is intended by a conservative amino acid substitution is well known in the art.

An additional embodiment utilizes the techniques known in the art for the construction of Fab expression libraries (Huse et al., Science, 246:1275-1281 (1989)) to allow rapid and easy identification of monoclonal Fab fragments with the desired specificity.

Also, this technology encompasses bispecific antibodies that specifically recognize SCF. Bispecific antibodies are antibodies that are capable of specifically recognizing and binding at least two different epitopes. Bispecific antibodies can be intact antibodies or antibody fragments. Techniques for making bispecific antibodies are common in the art (Millstein et al., 1983, Nature 305:537-539; Brennan et al., 1985, Science 229:81; Suresh et al, 1986, Methods in Enzymol. 121:120; Traunecker et al., 1991, EMBO J. 10:3655-3659; Shalaby et al., 1992, J. Exp. Med. 175:217-225; Kostelny et al., 1992, J. Immunol. 148:1547-1553; Gruber et al., 1994, J. Immunol. 152:5368; and U.S. Pat. No. 5,731,168).

Techniques described for the production of single chain antibodies (U.S. Pat. No. 4,946,778; herein incorporated by reference) can be adapted to produce specific single chain antibodies as desired. Single-chain Fv antibody fragments comprise the $V_H$ and $V_L$ domains of an antibody, wherein these domains are present in a single polypeptide chain. Preferably, the Fv polypeptide further comprises a polypeptide linker between the $V_H$ and $V_L$ domains that enables the single-chain Fv antibody fragments to form the desired structure for antigen binding. For a review of single-chain Fv antibody fragments, see Pluckthun in The Pharmacology of Monoclonal Antibodies, vol. 113, Rosenburg and Moore eds., Springer-Verlag, New York, pp. 269-315 (1994).

3. Other SCF Inhibitors

It is also contemplated that inhibiting SCF can be accomplished by a variety of other types of inhibitors. For example, in some embodiments a small interfering RNA (siRNA) can be designed to target and degrade SCF mRNA. siRNAs are double-stranded RNA molecules of 20-25 nucleotides in length. While not limited in their features, typically an siRNA is 21 nucleotides long and has 2-nt 3' overhangs on both ends. Each strand has a 5' phosphate group and a 3' hydroxyl group. In vivo, this structure is the result of processing by dicer, an enzyme that converts either long dsRNAs or small hairpin RNAs into siRNAs. However, siRNAs can also be synthesized and exogenously introduced into cells to bring about the specific knockdown of a gene of interest. Essentially any gene of which the sequence is known can be targeted based on sequence complementarity with an appropriately tailored siRNA. For example, those of ordinary skill in the art can synthesize an siRNA (see, e.g., Elbashir, et al., Nature 411: 494 (2001); Elbashir, et al. Genes Dev 15:188 (2001); Tuschl T, et al., Genes Dev 13:3191 (1999)).

In some embodiments, RNAi is utilized to inhibit SCF. RNAi represents an evolutionarily conserved cellular defense for controlling the expression of foreign genes in most eukaryotes, including humans. RNAi is typically triggered by double-stranded RNA (dsRNA) and causes sequence-specific degradation of single-stranded target RNAs (e.g., an mRNA). The mediators of mRNA degradation are small interfering RNAs (siRNAs), which are normally produced from long dsRNA by enzymatic cleavage in the cell. siRNAs are generally approximately twenty-one nucleotides in length (e.g. 21-23 nucleotides in length) and have a base-paired structure characterized by two nucleotide 3' overhangs. Following the introduction of a small RNA, or RNAi, into the cell, it is believed the sequence is delivered to an enzyme complex called RISC(RNA-induced silencing complex). RISC recognizes the target and cleaves it with an endonuclease. It is noted that if larger RNA sequences are delivered to a cell, an RNase III enzyme (e.g., Dicer) converts the longer dsRNA into 21-23 nt double-stranded siRNA fragments. In some embodiments, RNAi oligonucleotides are designed to target the junction region of fusion proteins. Chemically synthesized siRNAs have become powerful reagents for genome-wide analysis of mammalian gene function in cultured somatic cells. Beyond their value for validation of gene function, siRNAs also hold great potential as gene-specific therapeutic agents (see, e.g., Tuschl and Borkhardt, *Molecular Intervent.* 2002; 2(3): 158-67, herein incorporated by reference).

The transfection of siRNAs into animal cells results in the potent, long-lasting posttranscriptional silencing of specific genes (Caplen et al, *Proc Natl Acad Sci U.S.A.* 2001; 98: 9742-47; Elbashir et al., *Nature.* 2001; 411:4 94-98; Elbashir et al., *Genes Dev.* 2001; 15: 188-200; and Elbashir et al., *EMBO J.* 2001; 20: 6877-88, all of which are herein incorporated by reference). Methods and compositions for performing RNAi with siRNAs are described, for example, in U.S. Pat. No. 6,506,559, herein incorporated by reference.

siRNAs are extraordinarily effective at lowering the amounts of targeted RNA and their protein products, frequently to undetectable levels. The silencing effect can last several months, and is extraordinarily specific—a one-nucleotide mismatch between the target RNA and the central region of the siRNA is frequently sufficient to prevent silencing (Brummelkamp et al, *Science* 2002; 296: 550-53; and Holen et al, *Nucleic Acids Res.* 2002; 30: 1757-66, both of which are herein incorporated by reference).

An important factor in the design of siRNAs is the presence of accessible sites for siRNA binding. Bahoia et al., (*J. Biol. Chem.,* 2003; 278: 15991-97; herein incorporated by reference) describe the use of a type of DNA array called a scanning array to find accessible sites in mRNAs for designing effective siRNAs. These arrays comprise oligonucleotides ranging in size from monomers to a certain maximum, usually Co-mers, synthesized using a physical barrier (mask) by stepwise addition of each base in the sequence. Thus the arrays represent a full oligonucleotide complement of a region of the target gene. Hybridization of the target mRNA to these arrays provides an exhaustive accessibility profile of this region of the target mRNA. Such data are useful in the design of antisense oligonucleotides (ranging from 7mers to 25mers), where it is important to achieve a compromise between oligonucleotide length and binding affinity, e.g., to retain efficacy and target specificity (Sohail et al, *Nucleic Acids Res.,* 2001; 29(10): 2041-45). Additional methods and concerns for selecting siRNAs are described, for example, in WO 05054270, WO05038054A1, WO03070966A2, J Mol Biol. 2005 May 13; 348(4):883-93, J Mol Biol. 2005 May 13; 348(4):871-81, and Nucleic Acids Res. 2003 Aug. 1; 31(15): 4417-24, each of which is herein incorporated by reference in its entirety. In addition, software (e.g., the MWG online siMAX siRNA design tool) is commercially or publicly available for use in the selection and design of siRNAs and RNAi reagents.

In some embodiments, the present invention utilizes siRNA including blunt ends (See e.g., US20080200420, herein incorporated by reference in its entirety), overhangs (See e.g., US20080269147A1, herein incorporated by reference in its entirety), locked nucleic acids (See e.g., WO2008/006369, WO2008/043753, and WO2008/051306, each of which is herein incorporated by reference in its entirety). In some embodiments, siRNAs are delivered via gene expression or using bacteria (See e.g., Xiang et al., Nature 24: 6 (2006) and WO06066048, each of which is herein incorporated by reference in its entirety).

In other embodiments, shRNA techniques (See e.g., 20080025958, herein incorporated by reference in its enterety) are utilized. A small hairpin RNA or short hairpin RNA (shRNA) is a sequence of RNA that makes a tight hairpin turn that can be used to silence gene expression via RNA interference. shRNA uses a vector introduced into cells and utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs which match the siRNA that is bound to it. shRNA is transcribed by RNA polymerase III.

The present invention also includes pharmaceutical compositions and formulations that include the RNAi compounds of the present invention as described below.

SCF exists in both transmembrane and soluble forms. Upon cleavage of the SCF soluble domain from the transmembrane form, SCF is released from the cell surface to function as the ligand of c-Kit. Thus, it is contemplated that SCF activity can be altered by inhibiting the release of soluble SCF from the membrane-bound form, for example, by inhibiting or otherwise reducing the activity of a protease that cleaves the soluble domain from the membrane-bound form.

In addition, it is contemplated that SCF can be inhibited by chemicals (e.g., a small molecule, e.g., a pharmacological agent) or other biological agents that bind or modify SCF. For example, one of ordinary skill in the art can design and produce RNA aptamers or other nucleic acids that specifically recognize and bind to SCF, for instance by using SELEX or other in vitro evolution methods known in the art. Furthermore, SCF activity can be inhibited by specifically degrading SCF or inducing an altered conformation of SCF such that it is less effective in interacting with c-Kit. In some embodiments, the SCF inhibitor is a "designed ankyrin repeat protein" (DARPin) (see, e.g., Stumpp M T & Amstutz P, "DARPins: a true alternative to antibodies", *Curr Opin Drug Discov Devel* 2007, 10(2): 153-59, incorporated herein in its entirety for all purposes). In some embodiments, SCF is inhibited by a small molecule, e.g., a small molecule that binds to SCF and blocks its function (e.g., inhibits its binding and/or other interaction (e.g., an activating interaction) with the c-Kit receptor).

It is contemplated that altering SCF activity can be effected by inhibiting the expression of SCF, for instance, by inhibiting the transcription of SCF, by inhibiting the translation of SCF, by inhibiting the processing of the SCF mRNA, by inhibiting the processing of the SCF polypeptide, by inhibiting the folding of the SCF polypeptide, by inhibiting trafficking of SCF within a cell, or by inhibiting the insertion of SCF into the plasma membrane. SCF activity can be altered by changes in chromatin structure or other means of epigenetic regulation of SCF (e.g., changes in DNA methylation). Also, SCF activity may be altered by specifically sequestering SCF in a vesicle or other cellular compartment that hinders its action upon c-Kit.

4. Therapies Using Inhibitors of SCF

Inhibiting SCF finds use in therapies to treat disease. Accordingly, provided herein are therapies comprising inhibiting SCF to benefit individuals suffering from disease. In particular, as shown herein, disease states involving fibrosis and tissue remodeling demonstrate aberrant SCF activity. For example, fibroblasts isolated from diseased individuals with fibrotic or tissue remodeling phenotypes directly respond to SCF, which results in the generation of a more severe phenotype that includes increased collagen production. As such, as shown herein, inhibiting SCF can significantly affect the generation of severe disease consequences including inflammation and remodeling of target tissue. Also contemplated are therapies targeting SCF during the generation of fibrosis associated with acute and chronic disorders that have either a dynamic disease course or a more predictable disease course. Indications that can benefit from therapy inhibiting SCF include, but are not limited to, idiopathic pulmonary fibrosis, chronic obstructive pulmonary disease, acute respiratory distress syndrome, cystic fibrosis, peribronchial fibrosis, hypersensitivity pneumonitis, asthma, sclerodoma, inflammation, liver cirrhosis, renal fibrosis, parenchymal fibrosis, endomyocardial fibrosis, mediatinal fibrosis, nodular subepidermal fibrosis, fibrous histiocytoma, fibrothorax, hepatic fibrosis, fibromyalgia, gingival fibrosis, and radiation-induced fibrosis.

Importantly, therapies targeting SCF reduce or eliminate toxic effects associated with other similar therapies, for example those targeting c-Kit. These undesirable toxic effects are associated with targeting an intracellular, rather than extracellular, target, and the more widespread and general changes in cell signaling that result. While the therapies are not limited in their route of administration, embodiments of the technology provided herein deliver the SCF inhibitor via the airway by intranasal administration. Such administration allows direct delivery of the therapeutic agent to target tissues in pulmonary diseases involving fibrosis and tissue remodeling, rather than relying on systemic delivery via an orally administered composition.

In certain embodiments, a physiologically appropriate solution containing an effective concentration of an antibody specific for SCF can be administered topically, intraocularly, parenterally, orally, intranasally, intravenously, intramuscularly, subcutaneously, or by any other effective means. In particular, the antibody may delivered into an airway of a subject by intranasal administration. Alternatively, a tissue can receive a physiologically appropriate composition (e.g., a solution such as a saline or phosphate buffer, a suspension, or an emulsion, which is sterile) containing an effective concentration of an antibody specific for SCF via direct injection with a needle or via a catheter or other delivery tube. Any effective imaging device such as X-ray, sonogram, or fiber-optic visualization system may be used to locate the target tissue and guide the administration. In another alternative, a physiologically appropriate solution containing an effective concentration of an antibody specific for SCF can be administered systemically into the blood circulation to treat tissue that cannot be directly reached or anatomically isolated. Such manipulations have in common the goal of placing an effective concentration of an antibody specific for SCF in sufficient contact with the target tissue to permit the antibody specific for SCF to contact the tissue.

With respect to administration of a SCF inhibitor (e.g., an antibody specific for SCF) to a subject, it is contemplated that the SCF inhibitor be administered in a pharmaceutically effective amount. One of ordinary skill recognizes that a pharmaceutically effective amount varies depending on the therapeutic agent used, the subject's age, condition, and sex, and on the extent of the disease in the subject. Generally, the dosage should not be so large as to cause adverse side effects, such as hyperviscosity syndromes, pulmonary edema, congestive heart failure, and the like. The dosage can also be adjusted by the individual physician or veterinarian to achieve the desired therapeutic goal.

As used herein, the actual amount encompassed by the term "pharmaceutically effective amount" will depend on the route of administration, the type of subject being treated, and the physical characteristics of the specific subject under consideration. These factors and their relationship to determining this amount are well known to skilled practitioners in the medical, veterinary, and other related arts. This amount and the method of administration can be tailored to achieve optimal efficacy but will depend on such factors as weight, diet, concurrent medication, and other factors that those skilled in the art will recognize.

In some embodiments, a SCF inhibitor (e.g., an antibody specific for SCF) according to the technology provided herein is administered in a pharmaceutically effective amount. In some embodiments, a SCF inhibitor (e.g., an antibody specific for SCF) is administered in a therapeutically effective dose. The dosage amount and frequency are selected to create an effective level of the SCF inhibitor without substantially harmful effects. When administered, the dosage of a SCF inhibitor (e.g., an antibody specific for SCF) will generally range from 0.001 to 10,000 mg/kg/day or dose (e.g., 0.01 to 1000 mg/kg/day or dose; 0.1 to 100 mg/kg/day or dose).

Pharmaceutical compositions preferably comprise one or more compounds of the present invention associated with one or more pharmaceutically acceptable carriers, diluents, or excipients. Pharmaceutically acceptable carriers are known in the art such as those described in, for example, *Remingtons Pharmaceutical Sciences*, Mack Publishing Co. (A. R. Gennaro ed., 1985).

In some embodiments, a single dose of a SCF inhibitor (e.g., an antibody specific for SCF) according to the technology provided herein is administered to a subject. In other embodiments, multiple doses are administered over two or more time points, separated by hours, days, weeks, etc. In some embodiments, compounds are administered over a long period of time (e.g., chronically), for example, for a period of months or years (e.g., 1, 2, 3, 4, 5, 6, 7, 8, 9, 10, 11, 12, or more months or years; e.g., for the lifetime of the subject). In such embodiments, compounds may be taken on a regular scheduled basis (e.g., daily, weekly, etc.) for the duration of the extended period.

In some embodiments, a SCF inhibitor (e.g., an antibody specific for SCF) according to the technology provided herein is co-administered with another compound or more than one other compound (e.g., 2 or 3 or more other compounds).

5. Kits

Some embodiments provide herein kits for the treatment of a subject. In some embodiments, the kits include an inhibitor of SCF and appropriate solutions and buffers. Embodiments include all controls and instructions for use.

EXAMPLES

Materials and Methods
SCF Nucleotide Sequences and Proteins

The human gene encoding Stem Cell Factor (SCF) is also known as kit ligand and has the official symbol KITLG and HGNC number HGNC:6343. SCF is also known as SF; MGF; SCF; FPH2; KL-1; Kitl; SHEP7; and kit-ligand. Two transcript variants encoding different isoforms have been found for this gene. The SCF (kit ligand) isoform b precursor is available at GenBank accession numbers NM_000899 (mRNA transcript; SEQ ID NO: 3) and NP_000890 (protein sequence; SEQ ID NO: 4). The SCF (kit ligand) isoform a precursor is available at GenBank accession numbers NM_003994 (mRNA transcript; SEQ ID NO: 5) and NP_003985 (protein sequence; SEQ ID NO: 6). The NCBI Reference Gene Sequence has accession number NG_012098 (SEQ ID NO: 7). For both isoforms, the first 25 amino acids comprise the signal peptide and the mature form begins at amino acid 26. The first 11 amino acids of the mature form are EGICRNRVTNN (SEQ ID NO: 8).

Bleomycin Model

Interstitial pulmonary fibrosis was induced in specific pathogen-free (SPF) female, CBA/J mice (6-8 weeks old; The Jackson Laboratory, Bar Harbor, Me.) by the i.t. injection of 0.003 U of bleomycin (Blenoxane, sterile bleomycin sulfate; Bristol-Meyers Pharmaceuticals, Evansville, Ind.; 0.15 U/Kg of mouse body weight) dissolved in 60 μl of phosphate-buffered saline (PBS). Controls received 60 μl of PBS by the same route. All procedures were conducted in a sterile environment and were approved by the institutional animal care and use committee.

Whole Lung Histology

Following anesthesia-induced euthanasia, whole lungs from bleomycin-challenged mice were fully inflated with 10% formalin, dissected, and placed in fresh formalin for 24 hours. Routine histological techniques were used to embed the entire lung in paraffin, and 5-μm sections of whole lung were stained with hematoxylin and eosin.

Production and Administration of Anti-SCF Polyclonal Antibodies

Anti-SCF antibodies were generated by immunizing rabbits with recombinant (whole protein) SCF and generating polyclonal SCF-specific antibodies. Polyclonal antibodies were isolated from the serum using a protein G column. The isolated IgG portion was quantified and used at the specified concentrations suspended in saline. IgG from pre-immune serum was isolated in a similar fashion for use as a control. Briefly, 100, 150 or 200 μg of control or anti-SCF was given to mice by intranasal administration 7 days after treatment with bleomycin. This treatment was repeated on a daily basis until 12 days after bleomycin administration. Thus, the treatment protocol is considered therapeutic.

Generation of Mouse Anti-Human Monoclonal Antibodies

After identifying an immunogenic human peptide (e.g., SEQ ID NO: 1 or 8), mice were immunized with a standard protocol. The determination of high titer serum antibodies indicated the appropriate immunization and fusion hybridomas were made. Culture supernatants were analyzed from individual clones for SCF-specific antibody and chosen based upon specificity. Five hybridomas producing specific monoclonal antibodies against the peptide were propagated and the monoclonal with the highest titer was subsequently tested in biologically relevant cultures. In some embodiments, a peptide having the sequence EGICRNRVTNN (SEQ ID NO: 8) was used to generate an antibody (e.g., a monoclonal antibody). In some embodiments, any peptide fragment (e.g., an antigenic fragment) of the SCF protein sequence (e.g., as provided by SEQ ID NO: 4 and/or SEQ ID NO: 6) is used to generate antibodies. In some embodiments, mutant or variant forms (e.g., comprising one or more amino acid substitutions with respect to the sequences provided by SEQ ID NO: 4 and SEQ ID NO: 6) of SCF are used to provide a peptide for generating antibodies. It is to be understood that these embodiments comprise additions, deletions, substitutions, post-translational modifications (e.g., glycosylation, cyclization, N- and C-terminal modification, etc.) and other variations of proteins and peptides that are known in the art of molecular biology as applied to provide a peptide for antibody generation.

Testing Mouse Anti-Human Monoclonal Antibodies

To demonstrate that monoclonal antibodies inhibit SCF, mast cell lines that are sensitive to SCF were tested. The HMC-1 cell line, a mastocytoma cell line that expresses c-Kit and responds to SCF was first used. In brief, HMC-1 cells were cultured in specific growth media and plated in 24-well tissue culture plates at a concentration of $1\times10^6$ cells/ml. Recombinant human SCF (1-100 ng/ml) was mixed with monoclonal anti-SCF antibody (12 µg/ml) and incubated at 37° C. for 30 minutes. After incubation, the antibody/SCF or SCF alone was added to the HMC-1 cells. After 1 hour or 24 hours, the cultured HMC-1 cells were harvested and mRNA and protein levels were measured as an indication of SCF inhibition by the monoclonal antibodies.

Analysis of mRNA Expression by Quantitative PCR

Cells or tissue to be tested were dispersed in 1 ml of Trizol reagent (Invitrogen). RNA was isolated as described (Invitrogen), and 5 µg of mRNA was reverse-transcribed to assess gene expression. Detection of cytokine mRNA was determined using previously available primer/probe sets (PE Biosystems, Foster City, Calif.) and analyzed using an ABI Prism 7500 Sequence Detection System (Applied Biosystems, Foster City, Calif.). GAPDH mRNA was measured as a control for normalizing mRNA expression. Changes in gene expression were calculated relative to gene expression in unchallenged mice.

Determination of Cytokine Production

Protein levels of cytokines were quantified using a Bio-Plex bead-based cytokine assay purchased from Bio-Rad Laboratories (Hercules, Calif.). Using standard protocols, the level of cytokines can be quickly and consistently assessed with this methodology.

Statistical Analysis

Data were analyzed using Prism GraphPad software. Unless otherwise specified, data shown are representative of two or more experiments. Statistical significance in all experiments was determined by one-way ANOVA, followed by a Newman-Keuls post test. Significant differences were regarded as $p<0.05$.

Isolation and Propagation of Pulmonary Fibroblasts from Patient Populations

The Institutional Review Board at the University of Michigan Medical School approved this study. All patients underwent clinical evaluation, including chest radiography, lung function measurements, and thin-section computed tomography before fiber optic bronchoscopy. In these patients, interstitial pneumonia was determined from a compilation of symptoms, physiological symptoms, and radiographical findings. Surgical lung biopsies were obtained via the Clinical Core at the University of Michigan Medical School from patients suspected of having interstitial pneumonia between May 2000 and May 2002. Histologically normal lung was obtained from resected specimens in patients undergoing thoracic resection. Each biopsy was processed separately using sterile technique in a laminar flow hood and processed for culturing primary fibroblast lines. Two pathologists who were unaware of any other clinical findings independently reviewed each biopsy and histological classification was based on previously published criteria for idiopathic interstitial pneumonia.

Interstitial pneumonia and normal biopsies were finely minced and the dispersed tissue pieces were placed into 150-cm$^2$ cell culture flasks (Corning Inc., Corning, N.Y.) containing Dulbecco's modified Eagle's medium (DMEM, BioWhittaker, Walkersville, Md.) supplemented with 15% fetal bovine serum (DMEM-15, BioWhittaker), 1 mmol/L glutamine (BioWhittaker), 100 U/ml penicillin (BioWhittaker), 100 µg/ml streptomycin (BioWhittaker), and 0.25 µg amphotericin B (Fungizone; BioWhittaker). All primary lung cell lines were maintained in DMEM-15 at 37° C. in a 5% $CO_2$ incubator and were serially passaged a total of five times to yield pure populations of lung fibroblasts. All primary fibroblast cell lines were used at passages 6 to 10 in the experiments outlined below and all of the experiments were performed under comparable conditions.

1. Anti-SCF Antibody Reduces Fibrosis and Inflammation

Experiments conducted while developing embodiments of the technology demonstrated that anti-SCF antibody reduced fibrosis and inflammation. Pulmonary fibrosis was induced in mice as described. On day 7 following bleomycin injury, mice were subjected to treatment with anti-SCF antibodies delivered into the airway by intranasal administration. Treatment continued until day 12 following bleomycin exposure. Lungs were harvested on day 16 and examined by microscopy and a series of micrographs were taken. Lung histology demonstrated that anti-SCF antibodies reduced overall inflammation. In addition, Masson's trichrome staining, which designates collagen deposition, was reduced.

2. Anti-SCF Antibody Reduces Levels of SCF, Hydroxyproline, IL-25, and IL-13

Levels of hydroxyproline and particular cytokines were monitored while developing embodiments of the technology. Lung tissue sections from the above experiment were examined for the presence of hydroxyproline, a collagen precursor. The data demonstrated that the anti-SCF antibody reduced the production of hydroxyproline and plasma levels of SCF in a dose-dependent manner (FIGS. 1A and D). Also, IL-25 and IL-13 expression, measured as a function of mRNA levels, were reduced, as was expression of IL-25 receptor (FIGS. 1B, C, and E).

In particular, the experiments tested the effect of anti-SCF antibody treatment in the BLM model (FIG. 1). Mice were treated with saline (FIG. 1, "SAL") or BLM (FIG. 1, "BLM") on day 0. On days 8 and 12, different groups were also treated intratracheally with non-immune (FIG. 1, "IgG") or anti-SCF antibodies (FIG. 1, "aSCF") at the indicated doses. H&E stained lung tissue sections from each treatment group were acquired and examined Fibrosis was quantified biochemically as lung hydroxyproline content (FIG. 1A). Lungs were then analyzed for IL-13 mRNAs by real time PCR (FIG. 1C). Plasma and lung tissue collected from SAL- or BLM-treated mice were then analyzed for soluble SCF by ELISA (FIG. 1D) or IL-25 mRNA by real time PCR (FIG. 1B). Values represent the means+/− the standard error with an n=7. A single asterisk (*) indicates statistical significance (P<0.05) when compared to the saline control group, while double asterisks (**) indicate significance with respect to the BLM+IgG control group.

3. IL-4 Stimulates c-Kit Expression in Human Fibroblasts

Figure 2:
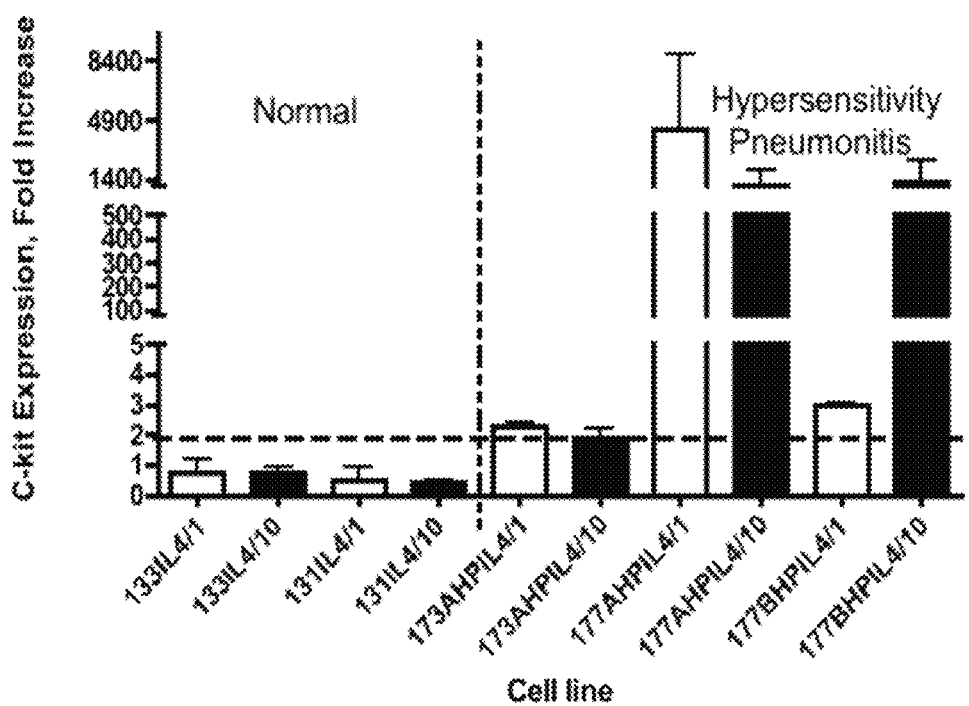
FIG. 2 shows a plot demonstrating that IL-4 stimulates c-kit expression in human fibroblasts.

Experiments conducted while developing embodiments of the technology demonstrated that IL-4 stimulated c-kit expression in human fibroblasts. In addition to the mouse model of pulmonary inflammation, SCF receptor is expressed in fibroblast populations from patients diagnosed with hypersensitivity pneumonitis and who thus have a pro-fibrotic environment. Pulmonary fibroblasts were grown from normal areas of lungs from patients (normal) and those diagnosed with hypersensitivity pneumonitis. Expression of c-kit was measured after stimulation with IL-4 at 1 or 10 ng/ml. Individual cell lines (133, 131, 173, 177A, 177B) were assessed using real-time PCR. Compared to lung fibroblasts grown from patients with non-fibrotic disease, fibroblasts from the hypersensitivity pneumonitis patients displayed significant upregulation of c-kit when stimulated with IL-4, a fibrosis-associated cytokine. The data demonstrated that SCF activated fibroblasts from inflammatory lesions, but not those from normal tissue, and promoted the expression of fibrosis-associated genes including collagen (FIG. 2).

4. A Mouse Anti-Human Monoclonal Antibody Blocks SCF-Induced HMC Mast Cell Activation.

Figure 4:
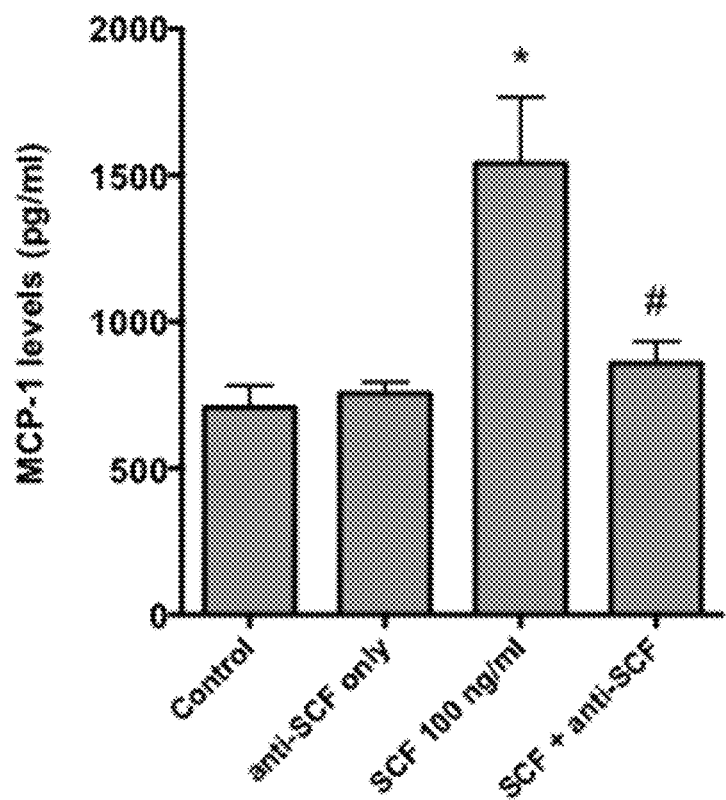
FIG. 4 shows a plot demonstrating that a monoclonal antibody specific for SCF inhibits the activation of HMC-1 cells for MCP-1 production.

Experiments conducted while developing embodiments of the technology demonstrated that the monoclonal antibody specific for SCF inhibited the activation of HMC-1 cells for MCP-1 production. The activation of mast cells is a classic SCF-induced response that can be used to monitor antibody neutralization of SCF-mediated cytokine responses. Previous studies have demonstrated that monocyte chemotactic protein (MCP)-1 is strongly upregulated by SCF in mast cells. A monoclonal antibody was produced against SEQ ID NO: 1 (FIG. 3). The efficacy of this antibody was tested using a human mast cell line, HMC-1, stimulated with 100 ng/ml of SCF. The monoclonal antibody (6 μg/ml) was preincubated with the recombinant SCF for 5 minutes prior to placing the SCF or the SCF plus anti-SCF onto the cultured HMC-1 cells ($1\times10^6$ cells/ml). The cells were subsequently incubated for 12 hours, after which the cell-free supernatant was collected and MCP-1 was analyzed by Bio-Plex. The data illustrate that the monoclonal antibody specific for SCF inhibited the activation of HMC-1 cells for MCP-1 production (FIG. 4).

5. SCF-Deficient Mice Subjected to BLM-Induced Injury have Reduced Fibrosis.

Figure 5:
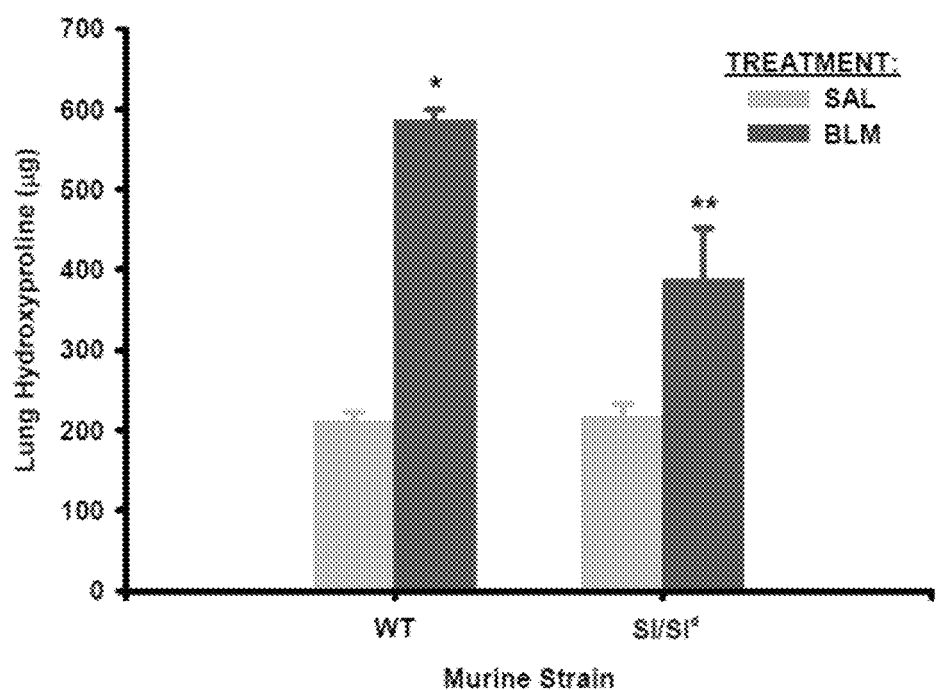
FIG. 5 shows a plot demonstrating that a lower amount of hydroxyproline is detected in a mouse deficient in SCF production after bleomycin injury.

During the development of embodiments of the technology provided herein, the effects of SCF deficiency in $Kitl^{S1}$/$Kitl^{S1-d}$ mutant mice were examined (FIG. 5). These mice have a complete deletion of the SCF gene in one allele (S1) and a deletion of the membrane-bound ligand in the other ($S1^d$), which significantly decreases the expression of soluble SCF. When these mice and their wild type controls (WT) were subjected to BLM-induced lung injury, there was a significantly reduced fibrosis in the mutant mice compared to wild type mice, both morphologically (Masson trichrome stain) and biochemically by hydroxyproline analysis (FIG. 5).

Wild-type and SCF deficient mice were treated with saline ("SAL") or BLM ("BLM") on day 0 and lungs were harvested 21 days later. Fibrosis was quantified biochemically as lung hydroxyproline content. Values represent the mean+/− standard deviation with an n=3. A single asterisk (*) indicates statistical significance (P<0.05) when compared to the WT saline-treated control mean, while double asterisks (**) indicate significance when compared to the WT BLM-treated group.

Similar suppression of cytokine expression and telomerase induction was also noted in S1/S1d mice. These data taken together indicated an essential role for the SCF/c-Kit signaling induced pulmonary fibrosis.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

We claim:

1. An anti-stem cell factor antibody that specifically binds to stem cell factor isoform b relative to stem cell factor isoform a or an antigen-binding antibody fragment that specifically binds to stem cell factor isoform b relative to stem cell factor isoform a.

2. The anti-stem cell factor antibody or the antigen-binding antibody fragment of claim 1 wherein the antibody or the antigen-binding antibody fragment specifically binds to a protein comprising an amino acid sequence provided by SEQ ID NO: 4 or antibody-binding fragment thereof.

3. The anti-stem cell factor antibody or the antigen-binding antibody fragment of claim 1 wherein the antibody is a monoclonal antibody or the antigen-binding antibody fragment is a fragment of a monoclonal antibody.

4. The anti-stem cell factor antibody or the antigen-binding antibody fragment of claim 1 wherein the antibody is a polyclonal antibody.

5. The anti-stem cell factor antibody or the antigen-binding antibody fragment of claim 1 wherein the antibody is a humanized antibody or the antigen-binding antibody fragment is a fragment of a humanized antibody.

6. The anti-stem cell factor antibody or the antigen-binding antibody fragment of claim 1 wherein the antibody or antigen-binding antibody fragment is a Fab, a Fab', a F(ab'), a Fv fragment, a scFv fragment, or a linear antibody.

7. A composition comprising the anti-stem cell factor antibody or the antigen-binding antibody fragment of claim 1.

8. The composition of claim 7 further comprising a stem cell factor isoform b polypeptide.

9. The composition of claim 8 wherein the antibody or antigen-binding antibody fragment is bound to the stem cell factor isoform b polypeptide.

10. The composition of claim 7 comprising a physiologically appropriate solution for administration to a subject.

11. The composition of claim 10 formulated for administration into an airway of a subject.

* * * * *

SEQUENCE LISTING

```
<160> NUMBER OF SEQ ID NOS: 8

<210> SEQ ID NO 1
<211> LENGTH: 15
<212> TYPE: PRT
<213> ORGANISM: Homo sapiens

<400> SEQUENCE: 1

Ser Ser Ser Asn Arg Lys Ala Lys Asn Pro Pro Gly Asp Ser Cys
1               5                   10                  15

<210> SEQ ID NO 2
<211> LENGTH: 45
<212> TYPE: DNA
<213> ORGANISM: Homo sapiens

<400> SEQUENCE: 2
tcgtcgtcga accgcaaagc gaaaaacccg ccgggcgatt cgtgc              45

<210> SEQ ID NO 3
<211> LENGTH: 5460
<212> TYPE: DNA
<213> ORGANISM: Homo sapiens

<400> SEQUENCE: 3
gggcttcgct cgccgcctcg cgccgagact agaagcgctg cgggaagcag ggacagtgga    60
gagggcgctg cgctcgggct acccaatgcg tggactatct gccgccgctg ttcgtgcaat   120
atgctggagc tccagaacag ctaaacggag tcgccacacc actgtttgtg ctggatcgca   180
gcgctgcctt tccttatgaa gaagacacaa acttggattc tcacttgcat ttatcttcag   240
```

```
ctgctcctat ttaatcctct cgtcaaaact gaagggatct gcaggaatcg tgtgactaat    300
aatgtaaaag acgtcactaa attggtggca aatcttccaa aagactacat gataaccctc    360
aaatatgtcc ccgggatgga tgttttgcca agtcattgtt ggataagcga gatggtagta    420
caattgtcag acagcttgac tgatcttctg gacaagtttt caaatatttc tgaaggcttg    480
agtaattatt ccatcataga caaacttgtg aatatagtgg atgaccttgt ggagtgcgtg    540
aaagaaaact catctaagga tctaaaaaaa tcattcaaga gcccagaacc caggctcttt    600
actcctgaag aattctttag aatttttaat agatccattg atgccttcaa ggactttgta    660
gtggcatctg aaactagtga ttgtgtggtt tcttcaacat taagtcctga gaaagattcc    720
agagtcagtg tcacaaaacc atttatgtta cccctgttg cagccagctc ccttaggaat     780
gacagcagta gcagtaatag gaaggccaaa atcccctg gagactccag cctacactgg      840
gcagccatgg cattgccagc attgtttct cttataattg gctttgcttt tggagcctta     900
tactggaaga gagacagcc aagtcttaca agggcagttg aaaatataca aattaatgaa      960
gaggataatg agataagtat gttgcaagag aaagagagag agtttcaaga agtgtaattg    1020
tggcttgtat caacactgtt actttcgtac attggctggt aacagttcat gtttgcttca    1080
taaatgaagc agctttaaac aaattcatat tctgtctgga gtgacagacc acatctttat    1140
ctgttcttgc tacccatgac tttatatgga tgattcagaa attggaacag aatgttttac    1200
tgtgaaactg gcactgaatt aatcatctat aaagaagaac ttgcatggag caggactcta    1260
ttttaaggac tgcgggactt gggtctcatt tagaacttgc agctgatgtt ggaagagaaa    1320
gcacgtgtct cagactgcat gtaccatttg catggctcca gaaatgtcta aatgctgaaa    1380
aaacacctag ctttattctt cagatacaaa ctgcagcctg tagttatcct ggtctctgca    1440
agtagatttc agcttggata gtgagggtaa caatttttct caagggatc tggaaaaaat    1500 gtttaaaact cagtagtgtc agccactgta cagtgtagaa agcagtggga actgtgattg    1560
gatttggcaa catgtcagct ttatagttgc cgattagtga tatgggtctg atttcgatct    1620
cttcctgatg taaccatgc tcacccatat cccactatac aaatgcaaat ggttgcctgg     1680
ttccatttat gcaagggagc cagtactgaa ttatgccttg gcagagggga gactccaaaa    1740
gagtcatcgc aggaagaagt taagaacact gaacatcaga acagtctgcc aagaaggaca    1800
ttggcatcct gggaaagtcc gccttttccc ttgaccacta tagggtgtat aaatcgtgtt    1860
tgcaaaatgt gttatgatgt gtttatattc taaaactatt acagagctat gtaaagggac    1920
ttaggagaaa atgctgaatg taagatggtc ccatttcaat ttccaccatg ggagagccta    1980
aaaataaatt atgacattta gtatctaagg ttagaaaacc acgcccacat gctaatatgg    2040
gtgttgaaaa ctaggttact tataatgcaa ggaatcagga aactttagtt atttatagta    2100
taatcaccat tatctgttta aaggatccat ttagttaaaa tcgggcactc tatattcatt    2160
aaggtttatg aattaaaaag aaagctttat gtagttatgc atgtcagttt gctatttaaa    2220
atgtgtgaca gtgtttgtca tattaagagt gaatttggca ggaattccca agatggacat    2280
tgtgctttta aactagaact tgtaagacat tatgtgaata tcccttgcca atttttttta    2340
taataagaaa acatctgact aaagtcaaag aatgatttct tatggtttat tttgatgaaa    2400
gttcttttaa catgtcttga atgtacacat aaaggaatcc aaagctttcc attctaactt    2460
aatctttgtg ataacattat tgccatgttc tacaaccgta agatgacagt tttcaatgta    2520
gtgacacaaa agggcatgaa aaactaactg ctagctttcc tttcatttca aaagtccaag    2580
```

```
aatttctagt atatttggat tttagcttct gttcaaagca atccagatg caactccagt   2640 aagtggcctt tgctctttttt tgtaccaaag agcccagatg attcctacag tccctttctt   2700
ctctaacatg ctgtggttcc ttaaatatga gtaatttctc taagatataa cccaggtgct   2760
ttgagaagct gcattaaggt gttcaggccc tcagatatca catggtacac ttgattagta   2820
ataaaaccag agatcaattt aaattgctga taggtcctgt ctcagtgtgt ggcattgact   2880
gttttcagga aaatagatac agattaatat gagttatgcg tgtaggttgt gtatagattg   2940
agaagataga tacttctcaa tctagtagtt tgatttattt aaccaatggt ttcagtttgc   3000
ttgagcatat gaaaatcctg cttaatgtgc ttaagagtat aataaatgtg tacttttgtc   3060
ctcaaaccta gtagctgggt tttaacactc atggacatgg tcttaatcaa tggagttaaa   3120
taaacaaatt cagcaagtta ttaaatctga catggtagga gaggggagat gtgtcctgct   3180
tattaaatgt gttggtccat tgaaagttac atggattgcc aatttttaaa acactaaagt   3240
tgaataaaat gcatgaacaa tagaaaaatg ctgaacatta ttttggatgc tagctgcttg   3300
gacattaact gtgttatttc tgctttgaga tgaaaatata tatttatctt tgcttatttt   3360
atcccagatg tgttctgaat atccttcttc ataaatcatg gaaaactcac tgctgagata   3420
gtaaaccatg aaatcgcctt tcagttggt gccatgtatc tgacagttcc atcttggaag   3480
gtttcaaaat tacctttaa aatgatctca gaagtctgta gattctcaat gatactgaaa   3540
gctttgcacc tctttggtag aaaccaggtc tatttagaaa atggctttat gataaatgtt   3600
gcctcctgag tgataatgaa gtgttcctgg atattgtatt gtaatttaat gtgcttacca   3660
cactgccaca ttttaatgag tcagagaaaa attaattttt cttcaataca ataatagaac   3720
aagtagccta ttctcttaaa aagtatgtga aaagaaaatt atgaaaaaat atgcatacct   3780
aatgaagtat tggttttagt aagaattaaa tacatttcat tgagctttaa agtactttgg   3840
agaaactttg gggcacgttt tcctactcta attcaactaa agttataaat aaagagaaaa   3900
actcattcag aaatcatgga ttttaaaaat attttactgc agccaagttt tcatttcaaa   3960
atgtaatttc agtttggagc ttttaggcat tatgtatatt taaaaaatat attcttcaaa   4020
aatgcatttt ggcatggtgg gatggatgtt gcaaaagata tccggagcct ccagtctgtc   4080
attaactgat atggtaaatc acctctcttc tttgggtctc aatttttat ttatctatat   4140 ggtaaactca gagatcactc cttaggggtg agtcctattg caatatgacc gacaaagaag   4200
acaaaatagc attgaaacta acccatacaa aatatccaac tctggattct gtgaataagt   4260
atcttgacca taaaaagtca ttgctgttct tgtttctaat gtaaatagtg tccattagta   4320
aaagtgaaat tcagtcttaa gtagggtgaa ttggatcacc atttacacaa gagatggctt   4380
tttcctttgc ttgaataaac attttggatc acctccaaag aatgaaaacc agtagtacgt   4440
tttagtcata ttagtcagga tgagaaacta taagatgtgt gtaacatttg gaaatgcacc   4500
aaagtgagcg tttaaatctt ctcattttat tgaaaactaa gagcagaaaa tgtaaaatgc   4560
tcatgaaggt tttgaatgcc aaaagatatt ttagaatcaa tttataaagg ggtaattcat   4620
taattacact ttaaaattgg aaagtgggat aagaaatcta agtaaaccca gcttatcttt   4680
gaaacaatat tattttgaaa ttggcttaaa ataaaaccca ttcagattga aattctaatt   4740
agctcatttg tggagtttga tcacacaatt cataatgttg ctgctttcca ttaactagtc   4800
ttgaaatgcc tttgttttgta aaataaaat aatggtactt tcattttata acaaggtgtt   4860
tttttcaaga aataatccat gctaaaatgg atatttgtga tcctgaaatg tttactaagc   4920
attgtaaatt tatttataac tgccatctcc aactacatcc ttatgatgtt tttaacaata   4980
```

-continued

```
aaattaaaac aactgttaaa ctaaaaacca caccgttttc cagtacttga tctctgagct   5040
acaatactca ctaaatataa ttttccaatc aaaatattct attctatatt ctaagggtta   5100
atatgtgatt atagtgtcca cttgccacca ttttttttaaa tcaatggact tgaaaagtat   5160
taatttagat ggatgcgcag atataccctc agttcagtca tagattggag tttgcatata   5220
ataatgtaaa tgtatgtcga cactattcta aatagttcta ttatgactga aatttaatta   5280
aataaaaaag gttgtaaaat gtgatgtgta tgtgtatata ctgtatgtgt acttttttaaa  5340 ataggtgtat gtcccaaccc tttttttatac aggtttgaat ttaaaattac atgatatata  5400
catatacttt attgttctaa ataaagaatt ttatgcactc tcaaaaaaaa aaaaaaaaaa   5460
```

<210> SEQ ID NO 4
<211> LENGTH: 273
<212> TYPE: PRT
<213> ORGANISM: Homo sapiens

<400> SEQUENCE: 4

```
Met Lys Lys Thr Gln Thr Trp Ile Leu Thr Cys Ile Tyr Leu Gln Leu
1               5                   10                  15

Leu Leu Phe Asn Pro Leu Val Lys Thr Glu Gly Ile Cys Arg Asn Arg
            20                  25                  30

Val Thr Asn Asn Val Lys Asp Val Thr Lys Leu Val Ala Asn Leu Pro
        35                  40                  45

Lys Asp Tyr Met Ile Thr Leu Lys Tyr Val Pro Gly Met Asp Val Leu
    50                  55                  60

Pro Ser His Cys Trp Ile Ser Glu Met Val Val Gln Leu Ser Asp Ser
65                  70                  75                  80

Leu Thr Asp Leu Leu Asp Lys Phe Ser Asn Ile Ser Glu Gly Leu Ser
                85                  90                  95

Asn Tyr Ser Ile Ile Asp Lys Leu Val Asn Ile Val Asp Asp Leu Val
            100                 105                 110

Glu Cys Val Lys Glu Asn Ser Ser Lys Asp Leu Lys Lys Ser Phe Lys
        115                 120                 125

Ser Pro Glu Pro Arg Leu Phe Thr Pro Glu Glu Phe Phe Arg Ile Phe
    130                 135                 140

Asn Arg Ser Ile Asp Ala Phe Lys Asp Phe Val Val Ala Ser Glu Thr
145                 150                 155                 160

Ser Asp Cys Val Val Ser Ser Thr Leu Ser Pro Glu Lys Asp Ser Arg
                165                 170                 175

Val Ser Val Thr Lys Pro Phe Met Leu Pro Pro Val Ala Ala Ser Ser
            180                 185                 190

Leu Arg Asn Asp Ser Ser Ser Asn Arg Lys Ala Lys Asn Pro Pro
        195                 200                 205

Gly Asp Ser Ser Leu His Trp Ala Ala Met Ala Leu Pro Ala Leu Phe
    210                 215                 220

Ser Leu Ile Ile Gly Phe Ala Phe Gly Ala Leu Tyr Trp Lys Lys Arg
225                 230                 235                 240

Gln Pro Ser Leu Thr Arg Ala Val Glu Asn Ile Gln Ile Asn Glu Glu
                245                 250                 255

Asp Asn Glu Ile Ser Met Leu Gln Glu Lys Glu Arg Glu Phe Gln Glu
            260                 265                 270

Val
```

```
<210> SEQ ID NO 5
<211> LENGTH: 5376
<212> TYPE: DNA
<213> ORGANISM: Homo sapiens

<400> SEQUENCE: 5
gggcttcgct cgccgcctcg cgccgagact agaagcgctg cgggaagcag ggacagtgga      60
gagggcgctg cgctcgggct acccaatgcg tggactatct gccgccgctg ttcgtgcaat     120
atgctggagc tccagaacag ctaaacggag tcgccacacc actgtttgtg ctggatcgca     180
gcgctgcctt tccttatgaa aagacacaa acttggattc tcacttgcat ttatcttcag     240
ctgctcctat ttaatcctct cgtcaaaact aagggatct gcaggaatcg tgtgactaat     300
aatgtaaaag acgtcactaa attggtggca atcttccaa aagactacat gataaccctc     360
aaatatgtcc ccgggatgga tgttttgcca agtcattgtt ggataagcga gatggtagta     420
caattgtcag acagcttgac tgatcttctg acaagtttt caaatatttc tgaaggcttg      480
agtaattatt ccatcataga caaacttgtg aatatagtgg atgaccttgt ggagtgcgtg     540
aaagaaaact catctaagga tctaaaaaaa tcattcaaga gcccagaacc caggctcttt     600
actcctgaag aattctttag aatttttaat agatccattg atgccttcaa ggactttgta     660
gtggcatctg aaactagtga ttgtgtggtt tcttcaacat taagtcctga aaagggaag     720 gccaaaaatc cccctggaga ctccagccta cactgggcag ccatggcatt gccagcattg     780
ttttctctta taattggctt tgcttttgga gccttatact ggaagaagag acagccaagt     840
cttacaaggg cagttgaaaa tatacaaatt aatgaagagg ataatgagat aagtatgttg     900
caagagaaag agagagagtt tcaagaagtg taattgtggc ttgtatcaac actgttactt     960
tcgtacattg gctggtaaca gttcatgttt gcttcataaa tgaagcagct ttaaacaaat    1020
tcatattctg tctggagtga cagaccacat ctttatctgt tcttgctacc catgacttta    1080
tatggatgat tcagaaattg gaacagaatg ttttactgtg aaactggcac tgaattaatc    1140
atctataaag aagaacttgc atggagcagg actctatttt aaggactgcg ggacttgggt    1200
ctcatttaga acttgcagct gatgttggaa gagaaagcac gtgtctcaga ctgcatgtac    1260
catttgcatg gctccagaaa tgtctaaatg ctgaaaaaac acctagcttt attcttcaga    1320
tacaaactgc agcctgtagt tatcctggtc tctgcaagta gatttcagct tggatagtga    1380
gggtaacaat ttttctcaaa gggatctgga aaaaatgttt aaaactcagt agtgtcagcc    1440
actgtacagt gtagaaagca gtgggaactg tgattggatt tggcaacatg tcagctttat    1500
agttgccgat tagtgatatg ggtctgattt cgatctcttc ctgatgtaaa ccatgctcac    1560
ccatatccca ctatacaaat gcaaatggtt gcctggttcc atttatgcaa gggagccagt    1620
actgaattat gccttggcag aggggagact ccaaagagt catcgcagga agaagttaag    1680
aacactgaac atcagaacag tctgccaaga aggacattgg catcctggga aagtccgcct    1740
tttcccttga ccactatagg gtgtataaat cgtgtttgca aaatgtgtta tgatgtgttt    1800
atattctaaa actattacag agctatgtaa agggacttag gagaaaatgc tgaatgtaag    1860
atggtcccat ttcaatttcc accatgggag agcctaaaaa taattatga catttagtat    1920 ctaaggttag aaaccacgc ccacatgcta atatgggtgt tgaaaactag gttacttata     1980
atgcaaggaa tcaggaaact ttagttattt atagtataat caccattatc tgtttaaagg    2040
atccatttag ttaaaatcgg gcactctata ttcattaagg tttatgaatt aaaaagaaag    2100
ctttatgtag ttatgcatgt cagtttgcta tttaaaatgt gtgacagtgt ttgtcatatt    2160
```

```
aagagtgaat ttggcaggaa ttcccaagat ggacattgtg cttttaaact agaacttgta    2220
agacattatg tgaatatccc ttgccaattt tttttataat aagaaaacat ctgactaaag    2280
tcaaagaatg atttcttatg gtttattttg atgaaagttc ttttaacatg tcttgaatgt    2340
acacataaag gaatccaaag cttttccattc taacttaatc tttgtgataa cattattgcc    2400
atgttctaca accgtaagat gacagttttc aatgtagtga cacaaaggg catgaaaaac     2460
taactgctag cttccttttc atttcaaaag tccaagaatt tctagtatat ttggatttta    2520
gcttctgttc aaagcaaatc cagatgcaac tccagtaagt ggcctttgct cttttttgta    2580
ccaaagagcc cagatgattc ctacagtccc tttcttctct aacatgctgt ggttccttaa    2640
atatgagtaa tttctctaag ataaaccca ggtgctttga gaagctgcat taaggtgttc     2700
aggccctcag atatcacatg gtacacttga ttagtaataa aaccagagat caatttaaat    2760
tgctgatagg tcctgtctca gtgtgtggca ttgactgttt tcaggaaaat agatacagat    2820
taatatgagt tatgcgtgta ggttgtgtat agattgagaa gatagatact tctcaatcta    2880
gtagtttgat ttatttaacc aatggtttca gtttgcttga gcatatgaaa atcctgctta    2940
atgtgcttaa gagtataata aatgtgtact tttgtcctca aacctagtag ctgggtttta    3000
acactcatgg acatggtctt aatcaatgga gttaaataaa caaattcagc aagttattaa    3060
atctgacatg gtaggagagg ggagatgtgt cctgcttatt aaatgtgttg gtccattgaa    3120
agttacatgg attgccaatt tttaaaacac taaagttgaa taaaatgcat gaacaataga    3180
aaaatgctga acattatttt ggatgctagc tgcttggaca ttaactgtgt tatttctgct    3240
ttgagatgaa aatatatatt tatctttgct tattttatcc cagatgtgtt ctgaatatcc    3300
ttcttcataa atcatggaaa actcactgct gagatagtaa accatgaaat cgccttttca    3360
gttggtgcca tgtatctgac agttccatct tggaaggttt caaaattacc ttttaaaatg    3420
atctcagaag tctgtagatt ctcaatgata ctgaaagctt tgcacctctt tggtagaaac    3480
caggtctatt tagaaaatgg ctttatgata aatgttgcct cctgagtgat aatgaagtgt    3540
tcctggatat tgtattgtaa tttaatgtgc ttaccacact gccacatttt aatgagtcag    3600
agaaaaatta attttctcc aatacaataa tagaacaagt agcctattct cttaaaaagt     3660
atgtgaaaag aaaattatga aaaaatatgc atacctaatg aagtattggt tttagtaaga    3720
attaaataca tttcattgag ctttaaagta ctttggagaa actttggggc acgttttcct    3780
actctaattc aactaaagtt ataaataaag agaaaaactc attcagaaat catggatttt    3840
aaaaatattt tactgcagcc aagttttcat ttcaaaatgt aatttcagtt tggagctttt    3900
aggcattatg tatatttaaa aaatatattc ttcaaaaatg cattttggca tggtgggatg    3960
gatgttgcaa aagatatccg gagcctccag tctgtcatta actgatatgg taaatcacct    4020
ctcttctttg ggtctcaatt ttttatttat ctatatggta aactcagaga tcactcctta    4080
ggggtgagtc ctattgcaat atgaccgaca aagaagacaa aatagcattg aaactaaccc    4140
atacaaaata tccaactctg gattctgtga ataagtatct tgaccataaa aagtcattgc    4200
tgttcttgtt tctaatgtaa atagtgtcca ttagtaaaag tgaaattcag tcttaagtag    4260
ggtgaattgg atcaccattt acacaagaga tggcttttc ctttgcttga ataaacattt     4320
tggatcacct ccaaagaatg aaaaccagta gtacgtttta gtcatattag tcaggatgag    4380
aaactataag atgtgtgtaa catttggaaa tgcaccaaag tgagcgttta atcttctca     4440
ttttattgaa aactaagagc agaaaatgta aaatgctcat gaaggttttg aatgccaaaa    4500
gatatttag aatcaattta taaggggta attcattaat tacactttaa aattggaaag      4560
```

```
tgggataaga aatctaaagt aaaccagctt atctttgaaa caatattatt ttgaaattgg   4620
ctttaaaata aaaccattca gattgaaatt ctaattagct catttgtgga gtttgatcac   4680
acaattcata atgttgctgc tttccattaa ctagtcttga aatgcctttg tttgtaaaaa   4740
taaaataatg gtactttcat tttataacaa ggtgttttt tcaagaaata atccatgcta    4800
aaatggatat ttgtgatcct gaaatgttta ctaagcattg taaatttatt tataactgcc   4860
atctccaact acatccttat gatgttttta acaataaaat taaaacaact gttaaactaa   4920
aaaccacacc gttttccagt acttgatctc tgagctacaa tactcactaa atataatttt   4980
ccaatcaaaa tattctattc tatattctaa gggttaatat gtgattatag tgtccacttg   5040
ccaccatttt tttaaatcaa tggacttgaa aagtattaat ttagatggat gcgcagatat   5100
accctcagtt cagtcataga ttggagtttg catataataa tgtaaatgta tgtcgacact   5160
attctaaata gttctattat gactgaaatt taattaaata aaaaggttg taaaatgtga     5220 tgtgtatgtg tatatactgt atgtgtactt tttaaaatag gtgtatgtcc caacccttt      5280 ttatacaggt ttgaatttaa aattacatga tatatacata tactttattg ttctaaataa    5340
agaattttat gcactctcaa aaaaaaaaaa aaaaaa                             5376
```

<210> SEQ ID NO 6
<211> LENGTH: 245
<212> TYPE: PRT
<213> ORGANISM: Homo sapiens

<400> SEQUENCE: 6

```
Met Lys Lys Thr Gln Thr Trp Ile Leu Thr Cys Ile Tyr Leu Gln Leu
  1               5                  10                  15

Leu Leu Phe Asn Pro Leu Val Lys Thr Glu Gly Ile Cys Arg Asn Arg
             20                  25                  30

Val Thr Asn Asn Val Lys Asp Val Thr Lys Leu Val Ala Asn Leu Pro
         35                  40                  45

Lys Asp Tyr Met Ile Thr Leu Lys Tyr Val Pro Gly Met Asp Val Leu
     50                  55                  60

Pro Ser His Cys Trp Ile Ser Glu Met Val Val Gln Leu Ser Asp Ser
 65                  70                  75                  80

Leu Thr Asp Leu Leu Asp Lys Phe Ser Asn Ile Ser Glu Gly Leu Ser
                 85                  90                  95

Asn Tyr Ser Ile Ile Asp Lys Leu Val Asn Ile Val Asp Asp Leu Val
            100                 105                 110

Glu Cys Val Lys Glu Asn Ser Ser Lys Asp Leu Lys Lys Ser Phe Lys
        115                 120                 125

Ser Pro Glu Pro Arg Leu Phe Thr Pro Glu Gly Phe Phe Arg Ile Phe
    130                 135                 140

Asn Arg Ser Ile Asp Ala Phe Lys Asp Phe Val Val Ala Ser Glu Thr
145                 150                 155                 160

Ser Asp Cys Val Val Ser Ser Thr Leu Ser Pro Glu Lys Gly Lys Ala
                165                 170                 175

Lys Asn Pro Pro Gly Asp Ser Ser Leu His Trp Ala Ala Met Ala Leu
            180                 185                 190

Pro Ala Leu Phe Ser Leu Ile Ile Gly Phe Ala Phe Gly Ala Leu Tyr
        195                 200                 205

Trp Lys Lys Arg Gln Pro Ser Leu Thr Arg Ala Val Glu Asn Ile Gln
    210                 215                 220
```

```
Ile Asn Glu Glu Asp Asn Glu Ile Ser Met Leu Gln Glu Lys Glu Arg
225                 230                 235                 240

Glu Phe Gln Glu Val
            245
```

<210> SEQ ID NO 7
<211> LENGTH: 94673
<212> TYPE: DNA
<213> ORGANISM: Homo sapiens

<400> SEQUENCE: 7

| | | | | | |
|---|---|---|---|---|---|
| agaatactct | gtgaacttat | tatgtatttc | atcattttca | aggctggtaa | aatcacacgc | 60 |
| cttcacatag | gcaaagagaa | cttcacattc | ttgtagtttg | gaaactccat | aggaaggaga | 120 |
| tactgttccc | cattagctca | agcacaaaag | tcccacagtg | gattctgatt | ggcccatctc | 180 |
| atgtgatgta | cccattcctc | caccaatcag | gactggacag | atcagggtac | taagcctatc | 240 |
| tccgatagtg | gaaggaggtg | ggaaaacaga | accatgtgaa | tgacagtctc | tcttgaaaga | 300 |
| taaggaatag | tctgaattct | ctaagtgaaa | gtgagtgcta | ataatggaag | aagagtgaca | 360 |
| ggaaagtgtg | ctaagcaaat | aaaaaaaaaa | aaaatctaag | ccgggcatgg | tggctcacgc | 420 |
| atgtaattcc | agcactttgg | gaggccaagg | cgggcagatc | acctgaggtc | agcagttcga | 480 |
| gaccagcctg | agcaacatgg | agaaacccccg | tctctactga | aaatacaaaa | cttagtcagg | 540 |
| catggtggtg | catgtctgta | atcccagcta | ctcaggaggc | tgaggcagga | gaatcgcttg | 600 |
| aacctgggag | gcagaggttg | cgtgagccaa | gatcatgcca | ttgcactcca | gattgggcaa | 660 |
| caagagtgaa | gctctgtccc | cccccgacaa | aaaaaaattc | ctaaccacag | tccatatgtc | 720 |
| taggttagat | catggttttc | ccatttatca | attgagggat | cttgagcaaa | tcaccatact | 780 |
| tctttgatcc | tcagtttcct | tatttatcaa | gtagaaaagt | taaaaattac | ctctcttaca | 840 |
| tgattgtcat | aagaagttat | tgacagaata | taaactaagg | gcttagacca | attcctggct | 900 |
| tatatgggca | acagcaacct | aattgaccaa | tatttaaggg | attcgctctg | ttcttttccc | 960 |
| tgtgacagat | attgacaata | aaataatgag | caagggcagt | cataattact | ttaaccaaat | 1020 |
| agtcaaacaa | acaaatacaa | aactgcagtt | gttttataaa | aaataggtaa | ttcatgctcg | 1080 |
| actttatagt | aagaggagaa | ttgaacaaag | caaagagatc | agggaaaacc | tccctgagga | 1140 |
| agaaaatata | gggaatactg | agttgagatc | tacatgataa | atgcatactt | actgggcaca | 1200 |
| atgatagggt | gaaacaaagt | ggtccaaaca | gaggcagaaa | ggagggtatt | tgcaaatggc | 1260 |
| ctgaggtgag | aattatgagg | acagaagggc | cttggccctg | gaaaaaaggg | agcacataat | 1320 |
| gaattgacct | tggagaagga | gggagaggcg | agatcctgga | ggccttgaag | gctttgctaa | 1380 |
| ggtgctaatt | tctttattcc | aagagcaatg | gcaagccacc | aaagagcttt | cagcagagga | 1440 |
| aatttcatga | tcaaagaggc | attcttctcc | ttttccccct | cctctagtca | ctcaaagaca | 1500 |
| gatatagaca | gtctgtctcc | ggtctggctt | ggtcaggcaa | taagtttcag | tttgtgagag | 1560 |
| acattttta | aagaaaaat | attgaaaaca | atatgtgtgt | ctaaagaag | atatccacaa | 1620 |
| aatagtgaat | gaacaagaga | tatttcacat | gcacaaagca | agataagact | tatttggtaa | 1680 |
| attacacctg | cctcttaaca | acaaaaacga | taaagctcag | gaaaaaagct | tttcaaaatt | 1740 |
| ggattaatca | ataatagcat | gagtgacgaa | tagtattgaa | agtattcaag | taaaaattag | 1800 |
| ataatcatga | aataacttc | tacccagtgt | gttaaatgtt | gaattccctg | agttgtataa | 1860 |
| tggtagccct | ctatttccat | aagaaaacat | ccccatccc | tcctgtccac | ctgggacata | 1920 |
| gccctgcctc | ttgttcagtt | taaaggaact | ccttggtttt | tcttctgcga | atcaactgaa | 1980 |

```
tgctggcctg catcccctat caaaagccag tcttaaggag agatctcagt cattctgacc   2040
catttgtgac ttccatataa gcctacccaa aatctttcat ttgcatatta gctctttcta   2100
atcccttgga tatttgcttc gacattctct tgattcaagt aacattatta cacaacaaaa   2160
ctgtaatgca gcagtatgag ggaaacaaaa gatacagtta cgtatgagaa agtcagtgat   2220
attaagaaag ctagaaccag ggaatggtgg aggtgggagg aggagacaga actgagaggg   2280
aaaaaaaatg gaaagaggga gaaagagaga ggagaatgag aatgcattgt aggagatgaa   2340
cgtagcatgt attattgagt tgaatgaaaa gaaattgaac tgaatttctg ttaggaacac   2400
tgccttgttt ctttaaacct ggtacaacaa attaggccat tcctttctat tggtctcata   2460
aaatccgtat ggttagattt atgattccca ggcttcagta actctcatac cattttgatt   2520
atttttgtcg tatctgtcct cctttagtac tacttgttat ttacttaatg ttatacatga   2580
aagtgagttt atattgacac taaatatttc ttttcttggg gggaaatgg tggtaaaggg    2640 gtacaaagtt ttagttagac aggatgaata agttctggag atttattgta cagcatgata   2700
actacagtta atgtactgta tacagttaac ccttgaacaa cacaggtttg aactgtatgg   2760
gtctacttat atgcaatttt tttttcaaac tcagatggaa aatacagtgt tctagagatg   2820
taaaacccat gtataagcag ggctgacttt tgtgtctgca cgttctgcag ggttgactgt   2880
gggacttgaa tatatgtaga ttttggtata cctgaaaggt ctaggaatca atcccctgaa   2940
tatactgagg tactccaaaa ctacaaagag tagatgttaa atactctcag ctcccaaaaa   3000
tgatgagtat gtgaggtgat ggatatacta tttagcctga tttaataatt tcacaatgta   3060
tacataagca gaacatcaca ttgtacgtgg taaatagata ctattttgt caaatataac    3120 ttaataaagc tggagaaaaa aaataaaatt ctccacttca aaaagccttt aaaggggccg   3180
ggtgcagtgg ctcacgcctg taatcccagc actttggaag gctgaggcag gcggatcacc   3240
tgaggtcagg agttcgagac cagcctggcc aaaatggtga acccgtctct ctactaaaaac   3300 aacaacaaca acaacaaaaa tacctgggcg tggtggtggg cacctgtaat cccagctact   3360
tgtgagactg aggcgggata tcgcttaaaa cctgggaggc ggaggctgca ttgagccgag   3420
attgcgtcat tgcacttcag cctgggagac agagcgagat tccatctaaa aaataaaaaa   3480
taaaaataaa tcttgaagaa aaaaaaaaca atcatttgct atgcctccag tatccaaatt   3540
aagctcattt tgatatttga tgttcgatat atttgtacta agagtaccta atgtataaaa   3600
atctttctaa gcaactatca acttggaatc atgattgatg tgctgtctat acatatttt    3660 tctaacatga gaaagtgaga acgcagtccc ccactaaatt atgcagtcga gtttcccaca   3720
tttggggaaa tcacagaagt cagcacatct ggagtgaaat aaacaagctt cgccctgatt   3780
acaggtttgg catattcatg tttaacaaac gcaccggaac taattaaagc aaatttggac   3840
tcctactcta ttattaaaat aactaattcc taaactcata cattattctt tcttttaaag   3900
atcactgatg ttaatgttca gctaatattt tcttttaaaa aattaatgaa atgctttgga   3960
atgttctcca gttatacaaa caaaaacaga cacattctgg agaatcaata aaatatttga   4020 agtattttt aagactgtac agctggagct ccaggtttaa attagagctc tgccatttac    4080
tagatatggt tggtcaagaa aattaacctt gtatttcatc gtccataaaa tgggaataaa   4140
ataataagat ctacactaat agatttgatg aaagaattta atgagataat ctatgcgaag   4200
ttcttagtct ggcaccctgg c acatgaataa gtgcatcaca taatgatgtt agctattatt   4260
attgtggttg cattatcttt ccgttcaaaa aagtacaact ttcaaagcct tgctgtgttg   4320
```

```
gcgacctgta gtttaataat ctatcgcttc tctttcaatc ttaatttcta aagacacagt    4380
aacaaaccat tccaaatgaa gcgtctcccc ttgcaatact taaccttgag tcaacaattc    4440
ttgtaattat taaatattca ttcactaaag taattgtttt ttttaaaaaa tagaggtgat    4500
aggacaatgg cctaactaca gatcgcaatt aaactttatt tctctaaggc aggcagggtg    4560
aattctttgc tccgaacctc ccggactcct ctccctctcc gactttgtat aacagaggga    4620
gctccgagcc ctctctggcg cgcgaggtat tcgtctgtc cccggggtg ccaggtgagc      4680 cccagcggat ccgggagggt aagctgggac tcctcgcgag cagtagctgc agggtaccaa    4740
gcttcgccct ctgcgtcccc gcgccttcgc ggtctcccgc cagtgcaggt ccggggcccc    4800
caggcgagcg gacaaggttg gcctaatctg ccaaacttct ggggcattta ccgtgctctg    4860
gccgccctcc cgattcttcc ctccgcgccc ttgcctgctt ctcgcctacc ccgggctccg    4920
gaagggaagg aggcgtgtcc ggagcaggcg ggcgggaact gtataaaagc gccggcggct    4980
cagcagccgg gcttcgctcg ccgctcgcg ccgagactag aagcgctgcg ggaagcaggg     5040
acagtggaga gggcgctgcg ctcgggctac ccaatgcgtg gactatctgc cgccgctgtt    5100
cgtgcaatat gctggagctc cagaacagct aaacggagtc gccacaccac tgtttgtgct    5160
ggatcgcagc gctgcctttc cttatgaaga agacacaagt gagtagggcg cgcccgggag    5220
ctcccaggct ctccaggaaa atcgcgccc ggtgccccgg ggaagccggc gctccctggg     5280
acttgcagct ggggcgtgca gggctgtgcc tgccgggtga gacaagagga tgcggggag     5340 gccggcgtgg tgtgtgatcc cgagccgagc cgggtgagcc agggagaaaa ggagtgggag    5400
tgctgagagg gagccagtgt caagtttgga gcctcagcag ttaagttttg agctgtcagt    5460
cggaaaccgt aattcccgtc tggtggaaag attggctttt gggccatgga atgttaagtt    5520
atcacgggaa ggcatgtctt tgcataggag acggttttcc cgtggattcc aggagattat    5580
gaaacagcac cccacgcgcc accctcacta gctctctcac tcagatttat ttgtgtagcc    5640
ccgaggtggg cgccgggcac caggagcggc gcgaacgcgg gtgcagccgc gggagcgaag    5700
ccaacgcgga actcctaagc ggcagctctc ggcggggcgg gaacctgccc gcctgcccgg    5760
gaaacttggc tctcggcggt gtctgcctag tttgcagctc tgtgtgggct ctaaagagct    5820
ctagtacctc cacaatgcac gcacctttt ccatttcaaa agggataaag gcttttata     5880 aaataggcac ctctgaatga tagtgattga gataattccc agtgctgcta aattctgcat    5940
tatacataaa gcactgtggg taaagcgctg cctgggggga caattagatt tttttttccc    6000
ttgaagaaaa tacctggttc ttcgtttaga aagggccgcc acggtgcccc tatccacagt    6060
tctcttcacc attgttgatt gttacctcct ctcactttcc cccttagaaa ttgttatgtg    6120
ttatctgccg cggttggcta agggttgccc tttcaccccc cagagggtct gttggagatt    6180
gcagttcctg aaatgtgtgg aagggggtgga agtggtgggg aaaaaggaaa ccggggtgtt    6240
tgtacacatc gttggtgtag aatgaaggca tcaatgtgct caaaatgctt tatcaaatga    6300
cctgcttagc atcatatttt aaacagatat ctaggcctgc aaaaagttgc aagactctag    6360
ccccttgtac cggtgtggta aaaggcaggg gaaagggaca ttgcctggct aaaagaggct    6420
tgcatagtct ctagagcact ctctaagaga aagacgcga tgtgcctctc ccctctctta     6480
caagcaggtt agctttcagg caaggcattg agcaccgcac ctggaatcac cacagcgtgc    6540
tgtcgaaatg caaatgttaa agattcttgc aacaaaagaa aagttttatt gtaatctctt    6600
gatttagaca agctttctgc gaaattataa gaagggtaga gacctattcc ttcttatagt    6660
agcatctgct cccatggatg gtggtgagat ctggggaag aagctgctac cttctagttc     6720
```

```
aggaaaagag cctaaacctt cctatttaaa caagaacaca ggagacagat aaggttaatg    6780
tccaacactc caaagccagg ggatgtacta tcaagtcact ttgagaggca gtaggattga    6840
ttatccttgc acccttgctt tgcaaaacaa atgtgagctc tgtaatctcc tttctcgctt    6900
tgattaaatg gctgtgtaaa tcggattaca tggaataatt ccattgaaaa ctagaaagag    6960
gtcaatctag tctgaaacat tgtgactgtg cattagtga ctcagtgctg ccgaccagag     7020
aaatttgaga aagctaagta ttttagatat gtgacctgtt cggtcacaca tcacacaagt    7080
taaagtgcag gcccctttggg ggaacttgct gatgttaaac ggcttgtagg caaggaggg    7140 cagtacccctt gttgaatgaa ggcattcatt gcctaggatc taatgacctt caaggttttt    7200
tttaagaata cttctagcga ttccacagtc actgaaaaag gggacactgg aaatagccca    7260
aaatcaataa aataatctgc agaaatggag gaggggatta gatctttcat attgttaaat    7320
tttctaatcc aaaaattaca aagacatttt ctgtgcaatg ctgcatggat ggaaggtagc    7380
ctatgtaaat tggacattaa gaaataggat cgattgttct gattctaatg ttatcctcac    7440
cagggaagaa tatctattaa tatttagtag tttaaatagt catttataaa catggcatca    7500
ataccatggt tctattataa agcaacttgt tctgtactct cctactaccc cacatataaa    7560
aaaaatttat agtaatattt taaaatgggg tttgatttga attacacagc tctccaagaa    7620
tcatggggac tccaggtatt ctggcctttc cgtcaagcta agtaagtgtg aaaattccat    7680
caacaaccac ttggggtttg atgaatgatt cattcattta gcatgttggt acacttcagt    7740
atttccaata taatgacaca ggcaataaat ttaagcacag ttctacagaa atgaatgtct    7800
tttgaatttt tcagatttct gtttgatttt attttattca gattgtgtgg ttttacagtt    7860
ttctagaggt gtttgtggct tgggcttaga aaaaacatct ctttcaatgt gtaactattt    7920
tttaaacata atattctgat acaccatatt ggataacaat caaggcacca tattttgcaa    7980
cactgattaa gatttggtta aaagtgccat tagcttaatg tgcctggtgt tacatttatc    8040
aatgttgtgc ttcatttta gtttggggat ggtttgtgag aagtgtcata actcctgtca     8100
atttcagaaa tactgagata agaaagattg atcttgcaaa caatgtaaaa aaggccattt    8160
taggcatact aactctcaga gaataagcaa atagaatgct aattttcact actccaaaga    8220
aaatatctct tttatgtctg tatgaagttt gtcatgtggg tgatgatgca agtttacttt    8280
gtagaagaaa attaacatac ttatgaaaag agcatttttt tagtcttgtc cttaagatca    8340
ctcaatttgg aatgtatgct ttgaataatt ccaatttatg tagctttta ttgatacatt     8400 ctgccaagac tttaaaaccc aagtgctaag ttgattacat ttaacataaa acaaggaaaa    8460
taaccatatg gaaatctgaa agtctgggcc aaaccaatta aaattgctaa attttattta    8520
cgtctaactc tgatttgaa gatagcaaat tctgggtcac attttttttt taataatagg     8580
tgactgaaat gtttccatca ccataaatca cataaaaatt tctcactcaa atagcaagtg    8640
tgggtattgg aggtttttta catggattgg caaattccac tacatgtggc cttcgcttta    8700
tatctgagaa taaaccatat ctgagcatat atgagaaaca cctaaaatat ggttggtaga    8760
aggattctag gttctagctt ctgaagactt agattctaat tcctgtttta ctactcatga    8820
gacaaatgac cttaggcaaa tatttgttaa acttttggg attttctgttt tttgtaatct    8880 gtatgatgat tataaaagtt ataaagattt ttctcgcatg gtggttttaa ggactaaatg    8940 aaatttttata tgtgtcttta taccagcata gtagcttact atatgtacag tttgaattta    9000
ttgttcctga gaagagagtg cctgctggcc tacttttaca agccagagaa aaactgactt    9060
```

```
attgcaggta aattatgcct aatgaaccaa gcacagagac caagttttcc taaatctacg    9120
tctgtcgatt tggtgactcc catgataggc taatatctgt ttatagacta taattaagac    9180
acatcaatcc aggaatatgt gaagacaaag gtgatatgtg ggcttaagag gtgctacgtt    9240
tttgaaggtt tttcttttaa agtacaaatg aatgagataa ttagaataga aaatagaaat    9300
ggaaaatgga aatattatct ttatcgctga ctcagtttca tatttctaca ctcttgctaa    9360
gttctccttg tatgattcta aggaattatt tcattttatt ttattttatt ttggactaaa    9420
gagacttggt tagtttccca tccctaatgt tctcgcactt gcttttctga gtgaggccat    9480
gcattcattt ctgtggggtg tctttgttgt ctttaccagg caacgtgcag tgacattttt    9540
ttttcattat gctagtttga gacttttatt tttcttttct ggattatctt aatgttccct    9600
tttgtaaatt attttttattc cctttttgtaa atttttattcc cttttgtaaa ttagggcaag    9660
gcatttggat ataaatctct gaagagtgat cttttatctt tctttctagc acataaatca    9720
tgagcagctg caagaaactg ttcttggtct tacacactgt tcttggtctt agtcacgtgt    9780
gtagacagaa caatttacaa aacaagttga gggaacacca agatatttttt ataatatatg    9840
ctgctttcag ggttgttttg tataggctct gtttcataga aacaattgac tgcagccttt    9900
ctgatttata gatgcagcaa gatgtgtttg ccttttcact taattatggg tatactaaaa    9960
actgtttaca ggggctggga gtttaagaga attgtcatga tctcatctct acctatttct   10020
ttctctatag aaaaaagagg tgggggagtg attttctcat agttggggct catggttctt   10080
tcttttaaaat cataatgtgt gtcatctaaa ggaagactgt tctttatgta cctgtctttg   10140
tcctttggct acatttttact attttttgtag gctgccactt tggcttggat attaggaggc   10200
tgatttcttt tattaacctg gataataagt agtagtaatt tgggaaatta tttgaactcc   10260
agatcttagt ttgctcaact gtaaaatgag taagtgagac taggtgattt ctaagtgcct   10320
tctggttcta aaattctcta tttctaaagt actagtaaaa tagatatttg aaccagatgg   10380
tatttaagct tccttcagtt ctcagattta tgcagccatt gcttcagtgt gaatgcacat   10440
tataaccatt gttttatgat tatgaataag ccaatgggga gaaatgaagg agatttaaat   10500
ttagactgtt ctacttttat gcatttcacc tactgcttga tatttctttg taaaaagaat   10560
ggtatttaca ctttcctgtt ttagcaaaat ccatagttaa agaggatctt tacttttctct   10620
gttctaaatt tttaagttct atgaaaaaga attctaagat aaagtcagct aaccagagga   10680
gataagctta caaaaggtaa tgcttccctg tatttgcctg ttttttttct gtccctttaa   10740
cttccagtac gtgtgtgcat ggagttgaaa tggagaaaga aaaccaagaa gggatctgat   10800
gatgtagtag aaagagcact gaggggagaa tcagaggaac tgatcctacc ctttgctctg   10860
cctcaagatg tgtgaccttg gactagtctc ccagtcttag tatctctgaa tcatgcccaa   10920
gatagttaat cctgagaaga tagtgaagat gagaggctgc agctggagac acggaggtgg   10980
aaagaggagg gagcctcagg gaaaggcagt tcctgcagat gatactatgc caaatctctc   11040
cttggctggc ttttgtctgg gtccagtacc atccttggaa cagtgcttgc ttacctcctt   11100
tccttagctg agagctggag caaacccagc agctagccgt agcccttttc tttttttctt   11160
tttttttttt tcttttagca gtcagaagct atggcagtct tttcttgttg acatgagaat   11220
attccaagat cagctggacc ctcctcaagc taggagaaca cacatttctc agaaaacagg   11280
gccacaacca tgaagataat gttcttctct aatcactggc attgcccact gagctatcca   11340
ctaaaacaaa gtttagaatt gaggcaatag tctagaaaat ttaaaaaaaa aaaaaagtag   11400
caatggctat tattgggata tttggatgca gaaattcagc acttgacttt gtgcctgtag   11460
```

```
ctgttgccct ggggctcttg aatgctgctg attagaacat gggtaaattg ggagggagcg    11520
gggcaataag gtagccttt  ctgtgttcca ggtacacaga cagcagctca aactttgtct    11580
gttgctcaca aagaatgcct ttgctcttta gggtgaccat gtaaaaggac atgaaaggac    11640
caccgcaaac tcatcggtgc tcacttgaaa aagcaagcct tgttcacctt tgcagaaagg    11700
gcatccccac tgcataattg catccctgtg caaacctggg aagaaagagc acaggttgga    11760 gggggcgtt  gtgtttgtct tgtatgccca tactgtgttg cctttcagg  agcagaagtt    11820 catctgctga acataagccc tgtgagtgct tagaactttt ccctcttttt caccttgaca    11880
taaaatccct aaagctgagg acctttccct ttcaatgtct tcactctgct ccagggctga    11940
attgcatctc attattggct tgtttcacct aaatgtgagt atttgagtgg cagtgaacca    12000
ggttgcctct aaggaataca actgaataat ggtggtctat tgtgaaggaa cctcttaggg    12060
ccctacagtg ctgagttttc tactgtttac ttggagttcc tttctcagtg ccttcccaaa    12120
caactgcctt ggaaaacac  acagattctt tggcttccaa gaagagtgtg acagagaaag    12180
tgtgctttgt tataaaggcc ttgtcaccct cctggatgtg ttatccatat cgatgtactg    12240
gctgttaaaa ttcatgttca ctgcagaact ctagatggag gagtggtaag aagggagggt    12300
agagatgttt tcatataaaa ttgtttctaa tgtgatctag aaaacccaag gattgcaaca    12360
cagacctcag cagtcataca tcattattta tggttctgtg taaatgtaca atttaacgct    12420
tctgaaatag taaacacatt agggatttcc tttttgatg  aacaaccaaa agctctgtga    12480
ttgctttagt ttggatttct cgcaactta  gaaaactgct gtattccgtg ggccctactc    12540
ataaatcttt gatgtgctct gttagtcaga ggactgacct tagcacattt gtcattctgc    12600
tgtttgaaag atacattatc acagtatagg agaatggctg gtgctttcta cttccaggtg    12660
gtccaaagtg ggaactaaac aaaatgaggg gataataaag ggattaggca acattcatga    12720
aaaattcaga ggaaattatt agcataatgt ttttactatt tggatgacat taattgtatg    12780
tagaaaagca ctgaactaca aaatagggct tacataattc ttccaatatc tttgtaacaa    12840
attatatata tatatatata tatataataa tgtatataat atatatataa tgtacatatt    12900
tatatttatt cttagccct  gcccagaaaa gtgttttaa  aactttactt cctgtttgta    12960
atgtactgaa gccacagtac tctatgcttt aataatactt taaaaataat gtaccttttt    13020
ttaaaatatg aaactagggt ctttaagaaa aaaatgtatt taggcattta ttaggcttgc    13080
ttgatttatt tcatatatag atacacatat gactgtagct aattttaatt taaaattata    13140
agtagcttct aataatacta gcaaatcctt atataatgct cacaatgtca ggacctgttc    13200
taagccgttt gcatttattt atttatattt ttcaataatg agacttttaa atccaagact    13260
gatttgacca tttattgttt gcacttctgt acaaatgtca cacataatga ttcaacttga    13320
agagatgaaa tttactgtac tatgtgtcaa gtgtttggca tttaaatgtg tagccatttt    13380
aaatagcttc tatcattata ttataaaatc aaaccatcct gataatagat catgccaaaa    13440
tggcacttag tagaaaacag ttccaagatt aattaattca cagcactttt ccgctgagag    13500
gtagttatta tttttttaaa ccccatttca cagataggaa aactaagaca aggtctttct    13560
cctgccaatc ccaggtgttt attgcaaaag agactcagct ggcattaacc acagcgcatt    13620
agtgtggctt attaatacc  tcaaagatat gcattctgtt tacatgaaca ttgaatcaaa    13680
aacaaatgca actcagatgt tcaaaaaagc tgccagtaat agaatttgga caacaaaaat    13740
ttcatgattg cagttgcctc aaagagtggc tcctgccaac tgctcagtaa atacacttgg    13800
```

```
aatgttgtga aatgaatgga gacctaattc aggttgttag atactgatac attttttata    13860
agcctttttt ctaatggcaa aatttttaaca attgtgctag gtctgttata cacacaaatg    13920
tgtttggtgc atgactggca aggctacttt gtttactatt ttacagcatt aattttcagt    13980
gaatgcataa catcatttac ttagtgaaac tggagacaat gtgagagaat agcaaaggtt    14040
tgaatggata tagatcaaat gtagtattgg ttctgccact taccaacccc agtaagtttt    14100
tctctttgaa cttcactttc tcaatattta aaatgggcac agaagtaacc acctagtagt    14160
agtattgatg tgataattaa aagagataga ctgtctaaca tcacagcaac tggcacttac    14220
ttaatagagc attgtttcct tctctaaaag aatagtaaat cacacagaac attatacaaa    14280
tctgtatgct gtaagaaata acttcagtgt tagtaattcc tggctttggc tatagggctt    14340
tcataaataa aaaaattaaa accaatcctt agagactaat agcttaactc tcttatttat    14400
acgttatcta tcttatttga cactcataaa caccccttagc aaattttag aaaattttcc     14460 caattttatc ttctttactt ttctcccctt tctgttgaaa agaaataaca aagtaggcca    14520
aagacaagct gtttaagaag taagagcagc ttactgaata aggaaatata agacaaatta    14580
ataagttaat aactgtgaat tactccccat gggtgaaaca ccatgccaca aactgcacaa    14640
gtgtatctca ttcgattgta gcaaaatgtt gtaaaataca tattattatt tggcatcatt    14700 tttttaaca aagaaaaata aaaaccctga agttcagaga gattaagaaa acttgcccaa      14760
aatgagaatt taaaaagtgc aagtggaaga gtttgtattt gaagccaagc ctatttaaat    14820
ctaaaggcca gattccttct aatcactaca atataatgca ccaatataga cacgcatgca    14880
tacacataca aactgaaagg gttgaacttc tttgttttt ttttgttgtt gttgttgttt      14940
tttctaattt atttgtggag aagaagatgc aatttaactt tacaccagaa agactgagag    15000
caggcaaagc tgagtcctct ggttgagtga tgagttgctc ctgaccccac actcctcagt    15060
acttaccaga agtgtaaatg gctgtatgtg agcaacactc ccacaggtca gggagcctgg    15120
gtttcctcat caggctttcc cacccatctc cccagcagtc aaatggaaac cccttgcctg    15180
actcatctga ctgttgtgag ggaatctcat tgtaaactct aaagatgtcg tcttacttta    15240
tggaatcagg aattacttca ttgccaaaaa gctttctgtc tttcaaataa agtggtactt    15300
tgttggcaga gggcagattt taaaatattt taaagttatg tttcaaaata acttcttgga    15360
aatagaaaga tacttcagaa agtacttta tcaatttgct ctgatcctct ttacatgatg      15420
ttttggaaga tggttttaaa tgtctgtgat catattagga aattatttga taataatgtc    15480
gtttatgtct ggcttttaaa gctaccagcc atttatattg tggcctttgt tttgttcatt    15540
tcttatcaat ccaactgcat taatattaaa aaaatattt tctgcattaa tatcgcaaga     15600
ttttaaatgg gtgattgtca gcacaacctt atcagcagca tcaccttgta acatactcaa    15660
tagcagttta gtacaaatga aaatgttggc taaaaagtcc tggcatcatc tcaacacagg    15720
taaaggagac aacagaacag agatgtgctt aaccaaactc tgcagtcaga tggtctgctt    15780
tggttgccta agaacgaaaa cctcttagcc tcaatttccc catctgccaa acagaatgag    15840
caatggtaca tttatcatag gtagttataa ggataaaatg aaataatcca caaaaaagca    15900
cttagtccag tgctggacac caagaaaata ctaaataaac atttactctt gctattacca    15960
ttaaacaaat ggtaatgtaa tgcttatcaa tagtgatggc tcctttctta aagaaagtga    16020
ctttaactgc aaaatctcca ctaccagagt gaaagggaaa gttgaagcaa tttatccaag    16080
taactccagc ctcaaattca cttttgtcct gagtaatgta gttgtttta ttctttttt      16140 aaaacaaaaa ctgaaaaaga aaaatgtgta taattagaat cacaaaagag tttacctaga    16200
```

```
gcaaagttac ttctttctat catgtgccca agatcgcggc accaatatgt ggtggctggc   16260
ttatgaaaca gattcggatt cagagctcgc attcccaagc tctttgcttt acctggaatt   16320 aggggacag aacatgagtc attcccattt tgaatcagtg agtgattgcc tacttttccc    16380
tatatgagtg aagtcatttt cagcatccat agaaatatag ccacttgtca aaagaaaatg   16440
gaaagaacat ggcttttgtg tcaaaagcat atagatttta cctctggctc ttgactctag   16500
cttgacatgg gaccttaggc aatttattta tctttcctta accttctctt aaacttctgt   16560
aaaatggaag aataatactt tgcagcttcc ttctcttgtt tcctcactct tttttctctc   16620 ccttcttcc ttgttctttc ccttcttttt tttaaaaacc tggaaataat gttatatacc    16680
taatttgtaa tcacgattca caatcactca ataattgta ctattagaaa acaatgtttt    16740
tcagaattaa cacggtttcc tgctctaatt ttaagaagta aattatattt ctcaaagtgt   16800
ttggctcatt ggccttgtgt agactggaag aagcatgggg tttggagtta gacagaatga   16860
gagttaaatc ttagctccac tattatgatt acaacatgat atttatttcc ttcctctagg   16920
ccccaatatc ctcattggtg taatggggtt gtaggggtaa tagtacatag ttggaagaac   16980
acaagaatta aatgagatta tagtctgggc atggtggttt atgtctgcaa tccaaacact   17040
ttggaagaca gaggcaggag gattgcttga gcccaggagt ttgagaacag cctgggcaac   17100
atagtgagac cttgtctcta caaaaatatt ataaataaaa taaataaata aataaataaa   17160
taaataaata aataaataaa tgagataata tgtggaaatt gtctgaccca gaagtgatgc   17220
tcaataaatt gtatctgtaa gctttaggga atggattatg ccagcagaca catcagtatg   17280
tattagactg tctgctctgt gtctgtaagg atgttgacac atgttggcga cctcacaagt   17340
tgtgaaagtc aagagagtta attaactgag cagtgctcta catactatac tgtccattca   17400
gaggcctagt gttgttgtat tgttctcaga cttgagcaat aaaaaatata aattttccaa   17460
gtacatgaaa actttagttt attaatgtct tctaaaatga gcctcaaatt agttttgta    17520 tagtatgatc atgaatagct ttggagactc ataaatctgg aatcatctct tcaaactgta   17580
tgactttgag tcacttgatt cttcggataa cattctgatt ttctcacttg taaaatgagg   17640
tttataatag tgtctaagtc ctaaggtgac tgtgaggatt aaatgagcta atgcataaga   17700
agggcattag acaggtacc agaaaacctc ggtaaatgtt agctcctttc aaataaaatg    17760
cagttttgca ttcaaaggtt gttcgtttgt tgttttattt ttttttgcat gtgttgaatt   17820
taataacttt atagaatcaa cagtttggaa atgtttccat tatgaattca ggttttatt    17880 tcttgtcagt gactctgttt agtttaaggg cttggttgtc cagattcatc tttgagtaag   17940
ttttgtatca atcaagacag atgcaagtta cttttatcag tccattactt caggtaaaca   18000
agcattccat tctttgacag aacattaaac tgttatgttc tttttgatgg agtgctgatt   18060
tgttcaaaac acttgtgaaa gagagaaaac agctcctgtt ttataactct tttgtaatac   18120
aaagtttgtt tccaaaggtt ttctggaagt ttccttgattg aatctttgat tgtggatacc  18180
acagtgatta atttaccaag ccggaaaatg tgggaagtaa ttttgggttc agttcagagt   18240
gggatctaac acaacacttt gaaccaatat taaaatgcag aaatctcttt tagatattga   18300 aaagaaaaa caaatatata tatattaaag tccctgcttt taaggcctaa aggagaatgt    18360
agtagaaaca ctgacatgtg taattttgt gaattgctta ggaacagaat tagatttaaa    18420
aaggaattcc ttttgcactt ttccctgaag atttgtgtcc tagcatttga ggagtaatac   18480
aggaaagtca gaacaagaac ttactgacag cgcaggagat ccatgtccta aattcatgta   18540
```

```
tgtggtactg tattgctatg cagctttcag gatgtccatt ttattgtcca tcaaaatgta    18600
ggggtagatc ctataatttt aaaggttctt tctaatgcac acaatctaga gttattaaca    18660
gaagtctgac tgtgtcatta ccctggctaa aatcctctac cgactttaca ttaccctcag    18720
gataaagtcc aaaccctcag cacactatac aaggtcctct gtggtttggc tgttgcttat    18780
ctccaccact cccgagtggt aagtttcatt ccagcgtcac ctaactatgt acaatgacat    18840
accaatattg ctgcacttgg tttccaaggc cctgagggcc tcgcatttgg gtagctttga    18900
tggtctctac tccaggaagt cctccctgac ttttgtttgc tcttttcct cagcccctct     18960 ccctactatg ttgtttagtg atcttaccct gagctcctgt agcatttaaa aaaacaatca    19020
tatcacttat cacattatat tgaagttatt tttttactta cctagctaag ttgtctaaca    19080
ctggtatccc tagctagtgg cacagtgcca aaatattgat aaaggtttc tgaactaaac     19140 tatgaattta atgccaaatg tctctttgag ggacaacatc cacctgtcag cattctaaga    19200
atggatccag acatttgaca attttgtgcc tgctgacctc agcagacaca tgaaactgca    19260
tgtaacactg tcctgtataa acatacatac attgttcaaa cagaattttc ctcagagaga    19320
gaaatgataa atgagccact ttgggtggta aagagaatg gagacagtaa attaaaaata    19380
aataaataaa taaggagaaa ggtgaggcca ttgcttgcca ttcttaagga aatgacacaa    19440
taggctgaat gacaagggcc agttaaaact cgctaatgcc agatatatga agacttaaga    19500
accagaaagg attttagggc agaatattgt tgatgatgat gaagaggaaa aatgttgatt    19560
tccgatgctt attctctgtg ccaggtcctg agctaaatgt gttacatact ttatgtctcc    19620
tgattctccc cacctgtgag ggtggtggta gtgtgattat tccatttgat acaagaggag    19680
gaatctgagc tcacagaggt tgagcaaatt tctcagcatc ttacaactct cagtcatcaa    19740
acctgatctg tttgttccta atttcttgct tagtattagt actgttgaca ttttattttc    19800
tcacctagag attttgtttg tttgtttctt tgtttgttta aatggagtct cgctctgtca    19860
ccaggctgga gtgcagtggt gcaatctcag ctcactgcaa cttccgcctc ccaggtttaa    19920
gtgattctcc tgcctcagcc tcctgagtag ctgggattac aggcacgtgc caccactccc    19980
ggctaatttt tgtattttta gtagagatgt ggtttcacca tgttggccag gatggtctcg    20040
atctcttgat ctcgtgatct gcctgcctca acctcccaga gtgctgggat tacaggcctg    20100
agccaccgtg cccagccgag atttttttg atacataata attcatgaga ctattacaaa     20160
tatggtaaat ggattcttcc ttcccagctc acccacactc aagatgcttc ctttaaaatt    20220
ctgttaacaa tttgtgctag ttaataggta gctagtgcaa tactcaagta aaggatgttg    20280
tgtagttttg gatactgaga tgtatagtct ttgtctaaaa ggagttgaaa gacagaaata    20340
tgacaatatg agagggttta gatgattcta ttagaatgat atttatgtat ttaaaacaga    20400
tatggttaag gagttcagca aaaataatgt ctcaatacat aagatcagag attaagcgtg    20460
gaggaagaaa gttggagaag gattaacaag aagtgatgtt ttcaaatttc atgtgtggtt    20520
agaagccatc atcttagtga ctcaaggcag taatactact gctttacaat acagtgctct    20580
aaaataatgt tacagatatt gcatgtactt ttaaaaacat atatcatttt ggggatactc    20640
tttgatgcca agtttaaaaa attctgaagt gtttaaaatg atacaaactt agagcatgat    20700
ctgtgttcct ttttttttta atcaggtaag cttcttggtt ttgggtgtag atctgaaaag    20760
ttaacatttc ttgaaccaat aaaatgtttc cagttttata taattatatc acaaagtcta    20820
ccttctgcct tgatttgcaa agaaaagctc caaaaaggac cataaagaag aggagataac    20880
acacaaatgg tgagcaatga agtagatgta caaaatggtt tgtgcagatt tggcacttaa    20940
```

```
aacatacagc agccgaagta catcttaaat ttcatttagt gaatatattg ctcacgagtc   21000
cctctcttca tttcctgagg aagtagatcc ctattctctc ccatatggtg agaaaatctc   21060
tttgctatcc agtttccctg tttacatttg ttcttccatc cccttctgat tcctcagcaa   21120
agcagctgct ttgaaaagaa gctcaaagga ttaccttgaa atggttaccc actctccccc   21180
ttttctgctc caagaagaaa gtttcttttct gtattttccc agcattatta agagtcaaga   21240
cttgaggcct taaggtacat ttcctatatt cttcttttgt tttaaacttg aaagcaaaat   21300
aatcttccca agtctaccat gaggatgaat tcagaatgc acaataactt acatttaccg    21360
agaaaactgt taagtcagaa tcttctaaaa tagagataac aataacaagt gtgatgccag   21420
tactcctatc ctgatacatt gtaaaaaatc atctccttcc ttactgtgtc ctacatcctt   21480 ttttctttc tttttttttg agatggagtt ttgctcttgt tgcccctgct ggagtgcaat    21540
ggtgcaatct tggcttactg taacctctgc ctcccgggtt caagcaattc tcctgcctca   21600
gcctccctag tagctgggat tacaggtgcc caccaccatg cccagctaat ttttttgtatt  21660 tttagtagag gtggggtttc cccatgttgg ccaggctggt ctcgaactcc tgaccttagg   21720
tgatccgccc accttggtct cccaaattgc tgggattaca ggtgtgagcc actgcgcccg   21780
gccacatctt cctttcttaa tgaatttaga gtctcctcct acatcaaaat ggtattagag   21840
agaatgctaa ggataattcc atggatctca cgataaacaa ttggaataaa agagcttgcc   21900
acttagtcat gattattagc atgaaaatgt gatgatgcag cctattttgg gggagggatg   21960
aagtgtcatt gaatcagctc atgagtagtc tggcatgcga cttctgtttt cttgcaaaca   22020
agttgcatga tagggaaaca tcaacactat gccagtgtgt ccctgaagaa aaggtagctg   22080
gttttgtttt ggtcaaagta ggaatgagtc tggaaaggga ttcagtttta tgaacattgt   22140
tttgcctgct ttagaaaaga tgacagatag ataagagtca accaatgctt tgggaagaga   22200
taagattagc atttaaaagc ttaacccatg tcatcacttc tgggtatgtc ttccctgagt   22260
gaaatcttat tctttgcatg cattttgaat gctgaatcac catgaataat ttttatgaat   22320
ggctacttta gaaatgttaa tggattgcaa ctcattgggg aaataaaaaa tttatggttg   22380
cgtattacaa taaattctaa ataaagcagt atatggaatt gttgacttct cagagacttc   22440
cagtgaactt actgcaggac agtgtctaca tttcagctct gtgtgatact ttcagtgttt   22500
tcgctttttt aatatgcccc ttttttgtcaa taaaggaaag aaactccact ttatacttac   22560
gtagtttctt cagaaaggga gctctgggga ttttatagcc aggtcagccc ttcaattttg   22620
ggccacatct accaggagaa gcattttttca atgattgttc attcattaaa attgtctatt  22680
tacgttgtcc ctgcccttct tggagcttgt agtctactca tggttttata gcctagtttt   22740
ccacttacat ggacctaggg aagtattaaa ggtacaaaga aaatggttaa aagttcaaac   22800
tgagaagcat ttagctaatc gtcactattt gaatttagaa gttattgagc ctaagagtga   22860
gaaggatgac aatggtttat acccaactga tgaacaaaac cctcctgttt atccttcact   22920
cattcattct aaatatattt acgagggggct tcttcacacc tgccattgcc ttagtcagtc  22980
tgacaaaaca gggagggact gaaagtccat atggcacctt atggtgctca cagtcaagtg   23040
taagaaacag ataataagca aaactggttg gcgatgttgc aattctattg tgtaaatatg   23100
gaaaccagct gctgaggatt gaattgtaca ttgtccagcc ttcatctctg ccccattata   23160
tgtacctggg tttattctct agtaacacaa tttagatagt gccagtacct tggtctgtac   23220
catataaaag agaatttat tgaaggagaa ctttatgag caattcagta gcagttagca    23280
```

```
atacatacaa tccacaaata tggaggatta tgtactatga gaaaggacca aatcaaggtg    23340
ctagaggtaa gaatgacgga taagaataat ataatcctca ttcttatacc atgtatattc    23400
ttgttgggag gaacagatga taagagtaaa ctaattgggt aatcaaaata atttctgaga    23460
atgaaaagtg cttaagggaa agcaaaactg tgatgtgatg tgatgtgata agaggtgctc    23520
cttaagacag gttacctggg aaggcttctc tgagaaggtg atatttgaac tgagtcctga    23580
atgatgagaa caacttgcca ttggcaaagc ccaaaaagga gaaaactggc agcagcaagt    23640
acaaagggct tgaggcagga attaccttcc aggtatttca ggaacataaa ggaggccagt    23700
gtggctagag catggtggga agataaaggt tactaaggcg taaacatgga gttggacaag    23760
tctgtcttcc gaaggtctct gtaggccttg attaggagtt ggagtcttac tgtaaatgta    23820
atgggaaggc attgggagat tttaagcagg tagtgatcat gttttatata ttcccagaag    23880
aagatactat tgtgagtaat aagtctgaaa gcaaagaagg ctatttagag gatccctgta    23940
atcttccagt aagagtgtgc taagagctta gcacaagcta agttgtaca  agatgaaatg    24000 gagagaaatg agttttgaga tttatttgc tggtagaaaa tatgatcaga tgtggaaata    24060
ggggactggg aagaatcaag gatagtgccc agattttggg cttaaaccac cattcttcaa    24120
gtttgggcat gatgttacta ggaatgcttg ttctagacag caatgacaat agccatagca    24180
aacatttata aaggtgtatt atttgacagg tactatacta aatgcccact tacataacta    24240
tatttaatcc tcagcaaacc tataaagtca gttctgttat tacacccatt tacagatgag    24300
gaaactgagg cccagaatga taaaataact ttccaacggc cataaggatt gtgtcaaagt    24360
agaaattaag atatgggcag tctgattcta aggttgatgt tttccaaccc cctcctctat    24420
accacttctc tgtgcatgag taaacacact gttttctttc tttctttctt tttttttttt    24480
tttttttttt ttttgagaca gagtctcgct ttgttaccca ggcttgagtg cagtggtgcg    24540
atctcggctc accgcaacct ccgcctccca ggttcaagcg attctcctgc ctcagccccc    24600
caggtagctg ggactacagg cgcatgccac catgcccggc taattttttt atttttagta    24660
gagacggggt ttcactgtgt tggccaggct ggtctcgaac tcctgacctt gtgatccgcc    24720
cgcctcagcc tcccaaagtg ctgggattac aggcgtgagc cacagcgccc agccaacaca    24780
ctgttttcta aagctgtttt ggatatatta gtgaagctga agttgacttt tgaaactttg    24840
ctatttaggt taacattcac ctgttgccca aacaattttt gcctcacttt tatactaggt    24900
agaaaagagc ctgcctgctt ggaagagcgg atccaaatcc aagctcaggg ggcagtttca    24960
caacctcttt atttcacttt ccagggctga tctttaatct atggggaggc agaggataaa    25020
tgagattgtt tacaattatt atgtgcaatt aaaaagaaaa cacattttt aaaaaatggg     25080 ttgtattgtg aatgattgta tagtcattta ctgttagcaa agcttttaga atatttaagg    25140
gatcaataaa gataaaatta taactgtagc atcaactgtg gtttaactgt agctaactga    25200
actagctata gttaactatt aactgtaatt aacaaaataa taattagagc attaatagtc    25260
atgtaatgtt ctcatagatc tgccaattgg cttgtgagtg ctttacataa cattgtctta    25320
tgtaatcttt tcaaaactgc aaaaacatgt tatcatcaca agaaaactga gtctcagaga    25380
ggttacataa tttgctctgg attacaacac gtgacagcac caggatttga atccatatct    25440
tactttgata acgttctctg ttttaaatgt catcatcttc ataaacagtg agcctgcaat    25500
tgacatatat tgttatcaga agaacaagtc ctgggcatgt cattgaacct gcagttgtag    25560
agtattgtta ccagagaaat gtgtctcagg catgtcaatg aatctgcaat tgaagttat     25620 tgttaccaga ggaacttgtc ccaggcatgc caactgtaaa tgctttgctg tgtttcagct    25680
```

```
ggtagaattg tattaaactc tcatggattg cctataaaaa attggtcttt tttaaaattt   25740
aaaataatcc ttatttttca acttgaattg tgaaacacta atgggaaatt tctaaggaaa   25800
attttgacca cccttaggag aaataaatgc ttaattactg gcttttcc ccttgttttg    25860 cttaggattt aattttggac aatatagtct actctgcctg attgaaacct gggatatact   25920
tcaaagagta tattgaagtg catttgatgg cctgtggaat ttttggaagg gccgtaggag   25980
cagactgcaa gctgagcttc agaacactc ccagcactca gaacttaagt ccactacagt    26040
ctgtaaatat gttgcggcca gtcagaaag ctgttactgc tgctgactgg agggtcttgc    26100
tgcccgcagt accaactaag ccaataaaat gcatgcccac agccagcctg tcttctcgag   26160
tatttccttc ccatatcaga tcttgcagtc acgcctaatt ggcagaaccg aagtcccatc   26220
tacaaccctg gataacttaa agggcgtctg ataaatggag ttttagctt ccagccatg     26280 atagtttaga gggatatgct aggagaatat tggaatggca attgaaagag acaatcaaca   26340
gtattctgtg cactcaatac acttaacttt tcttatcttt tttgttttta atttccatag   26400
gttattgggg aacagggggt gtttggttac atgagtaagt tctttagtgg tgatttgtga   26460
gattttggtg cacccatcac ccaagtagta tacactgtac ccaatttgtc atcttttatc   26520
cctcaccccc ctcaagttac tctaaatcaa gagcacctag tatgtagccc ttcaatcaaa   26580
tacaacgttg tatatctttt aagacatttt tgttttgttt gttttcttta acaatataac   26640
actcatgaac tatctaaaat attatatctc agactttata gagtacctaa taatcacata   26700
gagggcttac taaagatgt gctttcctga gatgcaccct cagaaatttg gattccctct    26760
gacatgcagg aatctgtatt ttaattaaac accccagatg attacacttt catctaaaca   26820
taacacagct gactcccttg gtttcagttg gaacaccttc agtgaaagaa ggaacatttt   26880
aacagtttat tccatcccac taaaaaggca gttggtatgt ctcacacaca ttgcataatt   26940
cgcaaagcca gtttgtgacc tttgccaatc aagcttgtca tctgatgtga cagagaaaac   27000
gatcaagatt gtgaacgttc tttgagctca tgtctctagc tccactcatt ttgatgatat   27060
ttggaagcag ttaaagtaga gtataaagat ttagtttatt ctcatgtagt aaaagatcca   27120
ggttggtggg tggcgggtcg tgaggggtgg ggggaacttt gttgaaaatt ttctgagctg   27180
cttcctcaga ttttttattta tttatttatt tatttaaaag gtcttgtgag actaaacttg   27240
tcagattttc agtagcagat gtgaaaatac atatgagcac attaattaca tccatagtgg   27300
gaaaaaaaca caaaaaggtt ctaggaaatt caggcattca gtctcagatt gggcacttgg   27360
gatcagatgg caactgaagc ctatgctcat ttcacatcac caaatggttt ggagttcaaa   27420
atattttaga gattttaaat aattacataa ttttttgattt acatgagatc tcactttcag   27480
aagcaagtca cgtatttgaa agagtataaa ttatgattta tgtttctgta gctgttttta   27540
gagagctaca gccctcagat tcttgtacat caggggtgatg tacaaccctc agattcttgt   27600
acatcagggt agttcaattt taagagcagc tagttggcat aagagtaaac ggtgcccgtg   27660
tccatggagt gctgaagatg cagatttcag aactttcatg aattttttaaa attatgtttc   27720 catactttgg ccggtgttgg gggaggtctg ctcgtcttat ttctttgaaa atacacactt   27780
attgcagaga gttggcggta gatatataaa cctagctaac ttaaagggca tctgagaaat   27840 ggcgtttta gttttccaga cgtgatagtt gagaattaaa ctagtaccca tcagttttct    27900
agactagctc agtctgttac acatcattat cctcacagaa attagaatta gtcattagct   27960
cgcatctcct taaaattaag tggattatac tgtgtagggg attttttttcc cctctgcttt   28020
```

```
gtataactgc taaagagctt tatgaatagc taatgatcta cttttaaac cattgttact      28080 aattagatag tctatactgc tgtcacaaat gcttactcta ttatgtacat ctttattaaa      28140
attagtaaca gtaaaaacct gaacactcag gccctatatt cttgcctgag gtaccagtct      28200
tttatcaggg attttacac agggtcaaaa cttctgagct cacctggctc tgttaacccc      28260
aggtgagttg ttccctattc ctaggccatt taaaaagag aaatgctgag tttattattt      28320
tagtcccact ctttcagggc tgtgtgttcc cttctaccaa gaccgaagtg aacttttcta      28380 gcccttttcca tgatcactca ctctcttctt tctttttgg caaactgtag taatataccc      28440
ttgaaattcc ctcatactca ttcactcctg tagtccatcc actgtgattg acttttagtt      28500
ccatcaactc aatggcaact gccctcatta aggtcagctc cattaagtac tctttagtaa      28560
acatcatatt gacatctttt agtgcttgtt ttattcattg ccctctccct ttggtatttt      28620
ttttccattg gctgctgtac cccacaatca actgatttcc ctctcatgta tttggcttca      28680
cattctctca tctcctacac agatagttca tgatagaatg gtatctatct atggtatggt      28740
agtattcact aaggttttg gtgataaact cccagactcc tgctgcctct tctcttccta      28800
catatctgga tcagcagata gcaccacttt ttacacagtc acccaaactg gaacctggaa      28860
gtcatttgtg cctcttcccc ttttgaccct accctctttt cattagtcac caagatcttc      28920
cgttctactt ccatatcctg ttgaacgtgt tcatttctct ccattctcac tgccactgcc      28980
ctagttaagg cccttatcat ctcagctttg gattacttca gtgacctcct aatgggcctc      29040
atgcccccag gtttgttgcc ctctctcccc cagtccatcc ttcattctga tgcctgataa      29100 acctttttaac aataaatcag atcttgacac tcccttgctt aaaatcattc caggtctccc      29160 cagtgcttt aaaatgaaat ctaaatcaat tagcaaggag ggcctctgca tatctctcta      29220
gccttgcctt tttttttttt tttgcttatt ctttgaaact tatttccaa tggagtaaaa      29280 aaatcacaga attctaagaa catgccttgt ttccacactt ctgtgggcac ctgctacttc      29340
ctctctcagg ggtcttctcc ctcactaact ttgagttggc tgcccccgat cacctttgga      29400
gaagcttctc ccccagaaa ctatcagccc ctccctcaaa tgcccctgtc ccccaaatgc      29460
ccccctcccc aagtcaggtt tagctgtact tggggcaggg ggcagttgag ggaggggctg      29520
ggccttttct ctctgactcc caccactgtg ctgtgttctc tagtagcttg agcttcctga      29580
ggccagtgat catagtcttt ctgtctttat cttatgtatt tattagatac tccatacatg      29640
tctgttaaat gaagaagtgg cccctgggat aatgttacta gaagtctgaa agcacccaat      29700 tttgtttta taagaagaaa caacttatcg cttatttttt tgggtttctc ccctccctct      29760
agctatgtaa attttttgttt aagctatagc taagtgtaac ttgatttacc tgctcgactc      29820
atttattcaa cctggtaata acttgacatg taatttcaat ttgaaactga ttgagttaaa      29880
gagacctata tgccttctgt aacatgaccc tttaaaataa aatttagtag ttcattaaat      29940
ataaatgaag tcagttttat tatctaactg gcctagtatt tttctttcca gcatagatag      30000
tgtaggtttt ggtttatatc caatccagca atttcctagc aaagtggcca taaggaagtt      30060
acctaatctc tcccgaattg tgttttgctc acctgcagag tagggtaata atatctacct      30120
ggttgatggg aggattacag gaaataatat ctgcaaactg cttgtcctat gcacagcccc      30180
ttagaagtca atatattttg agttatttcc actttaagta gtatttacat gtagaacgag      30240
gactgattat taaagggtga atttcccaa attttctca tgcattgaat accttgaaat      30300
ctttaaattc ccgttacatt aaaattccctt attatattac attgtctgcc ttttcatatt      30360
aagcaacttc tttctagttt tttttgtta taagagcata ttcattacat attttaatga      30420
```

```
tcacccatat ttttaaaacat ttttagctta cttcttcaca aaagggaagt tagaagagta   30480
tctttacaag attttggcac ccaccaattt ggactccaag ttggtctgag tttcaattag   30540
ttactctggt aacatctgtt ttattgatag tagttaagtt tcaaaaacta acaaatctac   30600
taaatgtttc agttgtccct ttaagattac ttaacagtgc ttagagaaga attttagtct   30660
gtgtaagatg attaggtatt ttccttataa tgtttaatgg taaattttta agcaattaaa   30720
aagatctgaa aaaagaagtc atatagaact gaatggttat tcaccaaatg aggatcctgt   30780
tgttggttta catagattat ttttggaaga tatggttcat atgagttaag aagacctgaa   30840
ctcaggacca attaccatac ctgtatcttg gtaacttgct ttcctgtctt tgggtagttg   30900
agccagttgg ctctcttcca aaatacattt gggctacaag ggaactgcct gcttcaatag   30960
ctggtatgca ggattaaaga gaagatgaat gttgttttg gcagcagctg ctgttttgtt   31020
cagggcagct ctaataccat ttcgtaggtc tgtgcataaa gaaaatgagc tacacaaaca   31080
cttaactctc tttttgactt tgtgacgtct gtaatatgga ccctgacaat gcatatttta   31140
aaatcacttc tcatattcat agagaaaaaa aggcttttt tctgtattt attttttgt   31200 ttttccaagt ttagaggatt ggtatcttct ggtttcttga acagcatatg tccccctgat   31260
attcttaggc tgcatgcatt ttaatttcta ctgaaggaaa ggaatctgca gtgtgactta   31320
tgtgttgcaa cacacgttca gattaagtcc atggtttgtt ttgggtgttt gtagctcctt   31380
ttcctggcat gtggcctttt actgtaagga aagctctgtg ttcaggaggg attggttatt   31440
gagtgaatag tccactggag tctgctgatg tttgttctca acaaaaatga aaattaagca   31500
agacctttgc ctttgaggtc ttcaacctca tcttcttgta aatccctccc accccagact   31560
tctttaaagt acttttctag tactgtctgc tactgtctgc tcccagaaaa ggaccagcca   31620
catctgtcac tgatgttaac ataaattta gtcagtatta cttccctcta ccagaactgt   31680
ttctactgca tgccttggtt gtaacagtgc acacagattt ctcattattt tttttcctaa   31740
tcatgtaaat gatttgaagg caacatttag caatgaaagg attattggaa ttttgtgtgt   31800
tgtgggggaa taaacggggg acacttttga tgcatgtttc tgaaaacaaa aatcgagaac   31860
tacccaggac gatatgtgtc tatacaatga aagactatcc agaaatgagg ggttatcaca   31920
caatgagctt gacctagaga gaaaagttgt acaatgataa aacaaagtag ccaaagaaaa   31980
atgtcatata cagctgcaga gaatgttaac agaaaaaaaa aatagatgat tacccaaact   32040
gaaaagatac attttagagc agaagtcaca aacacaggga catttgctt cagtgtatct   32100 ccattagggt gtgtgtgagc gtgtgtgcac acccacatat ttaggcaccc tattccctca   32160
gagtttccag aaattggaag aagaggaaga gaaaacaaag ataaatattt tgttgatata   32220
ttggaacatg tcatttaatt ggaagtcagt tgtctgttaa ctgaagctac tctaaacaca   32280
gttcagaact aagaaataaa tgaaaaaggt gtgtgaactc aaagtcagtg tcaaaatatt   32340
catgtgctaa aggtcatact cttttgtatat gggagatcta ctctataaag tcttttctca   32400
gaaagtttta ctcaaacatt tttgaagtac ttgtcttctg gtttcctagc cgatgcaaag   32460
cccataaacc acacaacaaa taattgcata acacccatag tttgaatagt ttctcatttg   32520
attcttacta ctagttcatg agatgggtaa ggcaaaaatt attttacta tcattttata   32580 ggctgataaa tggatactca gggagattag ctgacttgtt tgaagtcaca tgggaaggga   32640
ctgagaggtt ttctgatcc atgttctgcc catggtttcc aaaagcgttt ttttttttta   32700
atttcttctt gcccttggaa acctttgttt aaacagaatc ttactcagag gcatgaacaa   32760
```

```
ataaaacaac aaaaaaagct gagctgctct gcttaaaata aagggtgcgg gccaataatt    32820
ctggcagagg caattcactt tcctcatttg gaatagcttg accatcacta cactacacct    32880
ttcattcatt cattcattcc aaaagtattt caattgagct gtgttttatt tttctattgc    32940
tgctgtaata aattaccaaa aatttagtga ctggccgggt gcagtggctc atacctgtaa    33000
tctcagcatt tgggaggct gaagtgggtg gattacctga gctcaggagt tcaagaccag    33060
cctggccaac atggtgaaac tctgtctcta ccaaaaatac aaaaaaaaaa agaaaagaaa    33120
aaggccagcc atggtggcag gcacctataa tcccagctac ttgggaggct gaggcaggag    33180
aatcacttga atctggggagg cggaggttgc agtgagccga gattgcacca ctgcatccca    33240
gcctgagcaa cagagagaga ctctgtcaaa aaaaaaaaaa aaaattatc ataattttga    33300 agatcaaatg ttcaaaataa ggctcactta catcaaagta tcagttggac tatgttgctt    33360
tccaaaggct ctaggggaga atctatttct ttctcttttg cagcttctag aagctgccta    33420
catttcttga ctcttggtcc cttctctcta ttttcaatgc cagcaaggac atgttgagtc    33480
cttttcaggt cacatttccc cgaccttct tccatcatcg cacctctctc tgaacagagc    33540
tggaaaatag tctccatttt taaggaccat ggggattaga ttggacccag ggaatctagg    33600
atagtctctt catctctagt tcttaacgta atcatgtctg gaaagtccat tttgccatgt    33660
gtggtgatgt attcacaagt tccaagaatt aggacatgga catctttggg gccattatac    33720
ttcctgctgt aagctcccat atgggacaca tgttgtgttc atcatcaaga gtgcaggaga    33780
ctagaaatag gcatgttagc agtaacaata tgttgcaagt aatgacctga caatctgggg    33840
gaaacaggaa aactaaggaa caaacaaatg aaacctaaaa taaatttta aaagttatac    33900 aaacaagtac agtaatttgg aaccacttgg agaagggaag ctacaactac ataactgaga    33960
tactttgaaa gtcttccttt tatttgatga acctgaaccg tcacagaaaa gcaaagttta    34020
atatttcaat tcactgttta agaaatcaaa gtgtgtgtac aatattagaa agacttctgt    34080
gtagaaaagt taatactgaa aagtttcttt tttatataaa gaagtaagct ctgcatttca    34140
gctctctcct gagtatactg atgaaggagg tgtcattact gcttggcaaa aatctcaata    34200
tttctaactt gattatctcc ctgtcctaat gtttagctat gccagaatga attctttaat    34260
tttatgaaag gtggatattt ttaatggtag caaagtatat gcaaaattaa attacaatat    34320
gaatttattt ataatggctt taaaataaag ggctttaaga aatataggtt tttcagagat    34380
atttgaatgt tcataagcta acatagattt aatttagca ttgacccagt ggattttac    34440 aaaatgaaca aaactgtgtc tttgtaagat atttgaattt aactgatgca aaaaaattt    34500 atgttgccct gatcaaatca ttcttcaatt attatagcag tctgtgttga tatatttaa    34560 ggaactatca aaggacatat attaaaaatt atgatgactt gaataatata gactattcag    34620
ctgtggcatg gaatatggaa cagacttgtc tccatatgct tgatatttgc aaaagtatta    34680 aagtttaga gatctgctat cgcatcacag ttctcacaaa ccatctaaca gatttgcagg    34740
agttctggga cagtgtagag gggctaaaag gacaggagtc agaattggac agacctgggc    34800
ttactgattt caccactcag aagtcaccaa acctccctgt acctcaactc cttcatcttt    34860
aaaattagga tatatgaaag ttattttttt ccttattaga tatccaagat gcttggtgta    34920
tagtaaatgt tcagtaactt ttagctctat tcatggaatt gttcccaaaa cacaaccagc    34980
atctgcattc acattccagc gctctgcctg atagcattga actacctata ctcctattta    35040
aagccacact tcctacttga gaactgaatc tcaccccttc tttcctgctc aaggctgttg    35100
cccaagcagt cccctctctt ctgacctata ttgccaattg cttcctccta ctggatcatt    35160
```

```
cccataggca tacactcatt ctggtatttc aaccttctta caaataaaac tctcttcacc   35220
cccaatttct tgccagctac ttccccatct tggttttatt tatttatgtg tttgtttatc   35280
cagttgctct cctttgaagg aaaactcttc aaaacagctg ttcatactca ctgtttctgg   35340
ttaatctcat ctcctgcttt ctaaaaccca ctgtagactg gcttttcccc ataccacttc   35400
aataaaactg ctcttgttaa tattaccagt gaccttaatg ttgccaaacc agtggtcagt   35460
tatcagtcct tatcttactc ggcctataac tggcatttga catagtttga ccctattttc   35520
cttaaagtac tttttaaag tcttggcttc cttccatgat cttttgctt tgctctcttg   35580 gactcttttg tgggttctca ctcttctgtc agatcccta aggttagaac accatagcat   35640
gcgcagttct ttgttctttt ttatacttt actcactccc ttggtgatct catccactca   35700
tttgcttata tatggaaggt tatcatattt atatctgcac cccaagtttc cctcctaagt   35760
ccagatttaa atatcttgac ctggcattat cactagaata tctcaaagac atcttaaact   35820
taacatactc aaaatttaac tcctgatctg cctcccaaac cttctctacc cccagtcttc   35880
cccatatcag ttgatggcaa caccatcttt ccataccaaa gttcttatag tcatctttga   35940
ctctttctct caaatcgtac tctgtcagga aattctcatg gttcagcctt cagaagatgt   36000
ccagaatcta accactttca gtcaatgtat tactataacc ctttcttgat tggattacag   36060
cagcaacctc ccaacttgtc ggtttcattt tctacctgtt gtcaccctaa agtctatttt   36120
tattatagca atcagactga tcttatttaa ttaatttatt tttattctga agtatatatc   36180
cctcctctgc tcaaaatctt gcaatgaatc ctattttatt caagtaagag tcaatgtctg   36240
ggcaataggc ttcaacgccc tacatgagct gtcctctcca ttgtctctct gacatcatca   36300
tcttctactg ctccctaatt tactcttgct atgtcttaaa taacagatgc cttaaataga   36360
ccttaggacc ttggcaccag cttttctctc tgtatgcagt actcttccca cagatgtctg   36420
cgtggatcac tgccttagct ttgtccaatc tttggtgaaa ttttgtcttc ttaatgagac   36480
acttatcaat attaccctgt taaaaatttc aagctgtttc cacccatact gcaatctctg   36540
gaaagaaaag agtacagtta gttctatggc tcttctcgag actcagagat gcctggtgat   36600
ttgaccctcc ctataagtct tctttcaaca aggactcaag aaacttttag gtgtacatct   36660
atacttcctc caagggaatt cagctgaagt tactaggtag caggcactga tgtgtgcttt   36720
attacaagca tatgtcatgc actgatatgt attaatattt tattgttgag actggtactg   36780 gtggggtag ctgctctaga aaatgaatag aagttcatgc catatcccta aaaagctgct   36840
cagctagcaa ggtataagca gaaggaatga ttctacctac ccaacatcac ctatcattgc   36900
cacacgtatc ttgagtgttc agtgactttc tgatattaga gatggcctgg gagtctgctc   36960
tgcttgtgct gtatgtactc ttttgttatc taacttttt ttttttttggt gatgtagtct   37020 agcttttgtc gccaggctag agtgcagtgg cgcaatcttg gctcactgca acctccgcct   37080
cacgggttca aacgattctc ctgcctcagc ctcccgagta cctgggatta caggcatgca   37140
ctgccacacc cagctaattt ttgtattttt agtagagatg gggattcacc atgttggcca   37200
ggctggtctc gatctcctga cctcgtgatc cgcccacctc ggcctcctaa agtgctggga   37260
ttacaggcat gagccaccac gcccggccaa cctaacctt cttaaaactc agcagtacac   37320
ttggtgctgg gcaaagcctt ggtgctgggc aaagcagtac acatggtgac tcatgactgt   37380
gattgtcact ctgaacccaa gatcaccagt aaggcagagt agacattatg atcccaatcc   37440
cctttacctt gctctaatct tattttttccc atagcttttg acacctttg acatactgta   37500
```

```
taacctagtt acttatgttt gttgattaag ccttatgagg gcaggaattt tgttcattat    37560
ataggcctag cacctaggac aatgcctggt atacaccaga tactcaataa atacttgtta    37620
gatgaatgag aaaacaaacg tttctttagt atttattcaa tgccaggcgt aaaggattgc    37680
gaagaccagt aacagaattt ctgccattac atttctttga gcaaaggata tgattatggt    37740
catttctgag attggtccat tacagagatc cttagagaaa gttcccaaat cacatcagaa    37800
agagggtttt agagaaatat atttccaggg aggttacgtc ttagcaatga caatataaaa    37860
gaaagctgac tttaataaat tatatttaca catgtgaagg aagactgtta ttaagggaca    37920
gtttgtatgt aggggttgtc tgtccaaaaa gaagaatcct caaacagaaa taatttatac    37980
aacttagtct tcactgtggt ccaagaaaga tgatactatg aagagtgtga ccccacaatg    38040
ctagaagtag ccttaaataa aattatgcag gattactgct aaaatagacc atggtggtaa    38100
gggaataaaa ggatttcaat cttgaataca aaccactata tccatgtaat tagcattgta    38160
gttttagaaa ttttagcaaa taataatcat tatttgttct agtataatat ctagttagca    38220
tgcagatatt aattgaaaat aataatccag ttcctttta atatggctag ctatgtaaat    38280
agagaagatt tctagccatg tgcatctgga ctcttgtgta attttaagat tttacagaag    38340
aatggtatct cataaaagaa tgtgcacata ttttaagatg tcttcacatc tgcatggttt    38400
tgtcatgctg tttattttc ctggaacgtt catctttct tgtcagccc ttgcaagtcc    38460 tccttgtcct cctaaatcca gccacagtca catttctt ctggcttttc ttggcactgt    38520
cttcctgcaa ctggttctcc cccttaaggt taattgatta attgcttcct cttctgtgtt    38580
ccgaaagtgt ttatcacaag atgtgagtgt tatttattta cctgcctctg agtttcaagg    38640
gcatcttcaa catctttgtt accctagtga ctggcgttgt tcctgttgca taatatatat    38700
tcaataaatg gttattgaat ttgagcatca ggatatattt ttaccttgac cactgattga    38760
cccagcaaat atttattcag gacttttat atgcaagaca ctgtgttatg tgttgtgaag    38820
atactacaaa gataaatcag ttgcacaagt tcttgaaact ctacagtgta ataaggaaaa    38880
ataagtcatg cataaaagca actataatac ataatagaaa atgttatttt caagccgatg    38940
tgtaggttat gtgtgttcga gagagagaga gagaagacag attactttct gctagggttc    39000
aagaatgcct tcctgttggc taaggaaata ttttccttaa gtggctaaaa agctgtgttt    39060
caaaatattc ttttgatgtc tcacaaattc agtggaattc tcttaggtct aaaaatatac    39120
atctctctca ctttaacttg gtgtgctatt gtagattatt ggattaaagc actgctcagg    39180
gattatgctg cttcttgcca agcagtctac atttaaagta gaaataagat gtttcttttg    39240
gtgccataag gtatacattt tatgcattct ctagttttta gaagatacccc taagggctaa    39300 gtctttaaca tgctgctaca agtttattcc taattgccat tgggaaattg gctgaagaaa    39360 gttttttaaca aaagttaaca atattgtcat tgagagaata attcaaaatg gattttaact    39420
aaaagctttt aaaaactttg gtgagcatag cttgaatgcg taatatttaa ttgcatttaa    39480
gccaataaca tatattagac tggtcttttt gtgcatcaag gcattagatg ttaaaagttt    39540
gaatgattac agatcttaac tgatgatcac caagcaattt ttctgttttc atttagactt    39600
ggattctcac ttgcatttat cttcagctgc tcctatttaa tcctctcgtc aaaactgaag    39660
ggatctgcag gaatcgtgtg actaataatg taaaagacgt cactaaattg gtaagtaagg    39720
aatgctttac cgtgctgtgt aaaaaagagc tgtggctctt tttcctgtgc ttgttgataa    39780
aagatttaga ttttcttgc cccaaagtaa tgttttccta aagtggggaa agtaatcact    39840
gggttacaat aaagggttta tagaaagcag gtagtgagat atttagggtc atggataatt    39900
```

```
tgttggtaaa actggctagt tgcacaccac tgctgtgact gcttctttgc tggtcttctc   39960
cccatccttc ataggcagtg aaggaccttg gagagttcgc tgtgtgctga tgggcttgcc   40020
ccagcttgtt ccccataatc tctccagtgg gtttcccagc atgttctatt cccttcaca    40080 tgtcttccta ctcttcttta aaagtctaa cgaaaggaaa tctgaaatgg ctattctccc    40140
aattcaatca gcaggaagac cctgtcacat gtcagtgggt gtttgctcct tcagggaaca   40200
tagagaggtg attcattgcc cacatgttga agggactcat ctccctggtt tgtcacattg    40260
aactcttccc tcagcgaaag catttgcatt gcttccccaa gtcactgcca gctccatgct    40320
atgcttctcc agatgctttc tctcaagatc aagccacaga gtgggcataa cacatctgga    40380
atgcatcctt cccaaccgtc acgatctagg ggagatctta catgcttttt tgaaccatgt    40440
atgatttcgg gatgaacaaa gcttgagaag caatttttaa attcctagtt atttaaatac    40500
tgactagaga acggaggtga tgcgagaata ggtaagaaat gagggttgtg atatggagaa    40560
aaggatgaaa agtttatttt ttgaggtact gggataagga gtagaagggg ctctatttat    40620
cttccctcct cttgatatat attttctggt gtatatgtct tattttgggt ttataataga    40680
acttcaaaac agaagtttaa ggccactgtt gaagtcttgc tagcttagcc tcaatataga    40740
attagaaaca cacagacaca atttatacaa attccttagg acccagagag ttcaggttta    40800
aaagcattct tccatgcagc agcagcagat gtatcagtat gtcttacttg agggaactgt    40860
gagcaaagcc atgcaagagt tgtctgctat atacccagtt agctattgtg tatagggatg    40920
ggggtgaggg gggagtactt tttttttttt aaaaacatac tgtttaaaaa tagatcatgt    40980 ttttttttcct tgagttgctt gttagtttgt gacccaagaa acaatactaa aaggacagta    41040
tgtgtttaaa atctaacttt tgtgaatgac ctggattcta gtctagactt aacatgtgat    41100
ggctgtgtga ccttagtcaa ggcacttgac cccttctagc ctcagtttct tcatctgtta    41160
aatagagata atatgtcagc gggatctgag gataaattgt aataatgcag cctaagccca    41220
tagtgagcac agtgcctagc acatagtaaa tatttgacac acagcacata gtaaacagtg    41280
ttagacactg ttactatttt atgattatgt gaacttaggg aagaggaacc atactaagtg    41340
cctcagttca gagctgaaat gagtgtcagg tggcattact ggaagtagga tggtagtaag    41400
caccatgaga tcagtcacta tcttagctcc catctgacta cttacgccca tgcctaaatt    41460
catttatcaa taaattgttc tcagattcta aagctattg acaagaccaa gcaggatcat    41520
acagaaaatg ttatagtaaa cttgtgcgag atgacctagt ctagcaaaca tgcacatgat    41580
cttagctttc tataaggaag ataaagtttt tagagacaag atgaaggaaa aaaataagtc    41640
tacaaagcaa gatagaccct tgaagatgta atggtgcaaa actactttt aatgtatgtt      41700 atcttaatac ccaatggtct aagtcagttg ttggctaaat ttttcatctg gaatttttaa    41760
tggtgatatg agaagggcgg ggaaagcaaa gtagatgatg ttcattaaat gtttgctggg    41820
tgagtgaaga agaggaaatg atgtgctttta ctttagtgag catcacaatc acctgtcatg    41880
ctgatgaaaa ttatgggtac ctctattcac aatagcaaag acttggaacc aacccaaatg    41940
tccatcaata atagaagact ggataaagaa aatttcacaa atatacacca tggaatacta    42000
tgcagccata aaaaagatg agttcatgtc ctttgaaggg acatggatga agctggaaac    42060
aattattctc agcaaaatat cacaagaaca gaaaaccaaa caccgcatgt tctcactcat    42120
aagtgggagt tgaacaatga gaacacaagg acacagggag gggaacatta cacactgggg    42180
cctgttgggg ggtggggggcc tggaagaggg atagcgtttg gagaaatacc taatgtaaat    42240
```

```
gacgagctga tgggtgcagc aaagcaacat gatacatgta tacctatgta acaaacctgc    42300
acgttgtgca catgtaccct agaacttaaa gtataataat aataataaaa attacaggtg    42360
cctgggacta caccaagaaa ctactttggt aagtctgaaa aagggatcca aacatctata    42420
tttttaacaa aattctgaaa ggaggcttaa gagcaattgc tctagatggt ctcttctgtc    42480
attgtttaga aaccaaaatg tcttgactct tatttaatct caattcctat tatgactagt    42540
tatcatctgt gttgtataga cttataagga tgccagatta atacaaatct ccaaaatatg    42600
tttaaagtag gtcactactt tagaaccagc agatcacagt ctctcaggga cttatttaag    42660
gtacagctct aagggcatca ctataccgaa tctcaacttg tggagatggg gtgtgagaac    42720
cctaatgttt ccaactagca tctacataaa agttatttat gtagaagtat caggactgct    42780
taggccataa tgtttataga gtgtgtgtgt gtgtgtgcat gtgtgtgtgt gtattttaat    42840
gtttgaaaag aagtggagtg ttcctatcct aacttactaa tttcatttat tcaaacagca    42900
acatgagtga ctgttgagat ttatggatgt agataatcac agcctttctc tatacatggt    42960
ggggcagagc atcttgaagg aagtcgggaa tactaggttt ttttaatacc agctccacta    43020
ttacctggct gtgtggcctt ggacaaatca ctgaatcttt ctggcattca atttcctaat    43080
ttttcaaatg aggaacatgg acatgatcaa tagttattaa tctagggctg acaaacttca    43140
aatgcttaca catgaagctc agaattgtgc tgccttcata tgccttatgt tcatttctga    43200
ggagagtgtg tagcttttat catttctcag agaaatctaa gacccccaaag aagataagaa    43260 ctactaaatt agagaaactt ggaggccttt ttcagctttg aaattatttt attccataat    43320
gatgtttttt tcaggttgca cctcttggaa taattcaata ataactcgac tgaaggaggt    43380
tatataggat gagaggaatt tgctttgcag acataacctt gctacatttt atgtgaggga    43440
aagaaagtgg cctgacagtc catttttgcc tgtgctcaca gttattcctt caatggaaat    43500
cattcctttg cagcccctac cagtttcatc tttgcattag gtggcaacct gcactgtgcc    43560
cacacacttg aagttttttt gcttgaagtg attctcatgt cacagaagcc catgatttat    43620
gactttaatg tcaaattttt tttttaattt cttcttgaac actttgtact gcccccacgg    43680
tccccgtggt tttattcga aatgcttctg gcctgtttac taagcataat agttcatcta    43740
tttacagaac attttgcttt gtttctaaaa aaatgttgca acatttgttt taaatggcaa    43800
actcagactt acctaaagaa agggtcaagt atctgggaag aggatgaatc aagcttttat    43860
aacttgtatc tatgggatag ttaggttgca gattttagta gttgtaattg ttcatatagg    43920
aaggaaatcc agatattgaa aaagttcaaa ctagttttct ctgtgtattc tccctactct    43980
tctctttgtt tgtgacgact tgtttcttc atttgaggca atttaactca atatgatttt    44040
gttgctaaaa agaaaaaatg ttttgtcttt aactttctat tgggtaatga cttgtcttcc    44100
tcaaaatgtt tcttaaggtc ccatctccat ctcgtaaagg tgaaattact ctgtcttttc    44160
aaggtcagtc tacaaattag taagatagca ttagaacaaa ggaatctatt gtcttcctgg    44220
tcttgtgata ggcacttatt tcaagttggc tatatttata catgattcat ggagattatc    44280
gtaatgagag attataaaaa tatcctcaga taacacattt tcacactttg aatagacagt    44340
tttgattaat tctgattatt ttcttcttc aaatattatt gttctcaagt agaattacca    44400
ctgcattaaa gtgaagaatt ggagtctctg aatgtcccca tttctggatg aattctaagc    44460
ttttcttcag atgacctagg tatatcatta atagtgaaga tttcacataa ttttgtttga    44520
ccttcgaaaa ataatagttt gaaagatagt tttcaaattt tatttattta ggttgcaata    44580
tttagcattt taatttctgc tcctgtggtc agcagaaaat tctttctcta tttaaagcta    44640
```

```
aatttaggac attttgtatt ttaaaaaaag gactattaga aataatattt attaaaactc   44700
tagatagatt gctatattat caagcatatg agtcttattg ttaggaaaac attgttcttc   44760
ctttatagaa taaactactt ggataatatg tcttctgctc attgaatttt tatttttatc   44820
ttttgtagag atgtgggtcc cattatgttg cccaggctgg tctcaaactc ctggccccaa   44880
gagatcctcc cacctctgcc tctcaaaatt ctgggattac aggtgtaagc caccatgtgc   44940
agcctgctcc ttggtttttt agaacaatag ttatgagtac acagacacca tgcagaaaca   45000
ctttgcatgg attgtctcct ttacttttca taaccttaca agataactat ttttagccca   45060
gtatattggt tagaaagctg agatctagtg gtatttagta atctgattat catcacttgg   45120
gaaatagttg agtagaggtt tgaccccttta actacctatc attgaggcac agtaatgcag   45180
ttcataattt ataatgcctt cccagtagtt aagatgtaa gtttcaacta caattaatga   45240
attatcattg taacctactg aattttattt cctgaatagt agtcaccttta tcttactgtg   45300 attaggaagc tatcatattg tagaagctca gttagttact taattggaat catcatcata   45360
aggtgtgtca tcatcataag gtatgtcatc atcatgaggt attatacact ccctaaatat   45420
tgtagtttat aatctcttct atttgaaaga aaaaattgtt atctatcttt atttagatat   45480
tctttactga ggaacgatga ccttgaaaag cctcctgaag ttgtcatctt aattttttt    45540 tgagacaggt tgtctatcac ccagtctggg gtacagtggg gcaatcatgg ctcactggag   45600
cctcaaactc ctgggctcaa gtgatcctcc tgcctcagcc tctctagtag ctgggactcc   45660
agagtagttg ccaccatacc tgactaattt tttaaatttt tttcttgaga tggactctca   45720
ctttgttgcc aagtctggtc tcaaactcct ggctttaagc aatcctctca ccttggcttc   45780
ttaaagcagt aggattacag gtatgaacca ctgtgccctg ccaatttatt tttaatcact   45840
aattgagtta ccattttaaa aaagtccagt tacatttgaa aactataggt aatacacctg   45900
gttggttaga ttttttagtca atattagtgg tagataattt tttaggagaa acaaagaagc   45960
aaaaagcttt tttgggggt gttatttctg aaggttgaac aactaacata gtaagctact   46020
gtacctgagt gaacgatgat agaagtgtag agcttttttc ctctacagcc atgattatta   46080
aactttgcta ggtctgaaaa tcatagactc tttccccaga aaagttgaca taggcacagc   46140
attttgtaaa agtgtcaagg gagtcataga taactaatga attttgattc ctgccttgga   46200
cttgggagag acagcataac aagtaagggt cttgcaaaga tgtccaaggt ggccactgat   46260
ctcatgagat ttagggacct cagtgaccct tgaaccatga gatccaaagg ttttagatc   46320 agtgatctag agaggaagtt aagtgttctg actttgagtt attttcttc tgagtccaaa   46380 tacctgcagg gtgtggtatg cagccagtgc cagtttggct tgcaaagact tcttgttggc   46440
caagtctcca gcatttccaa atgctgttct cccatggatg ttttttccagt gtcactggac   46500 atggtcaatc attaagacat ccaaagaaga cagtaaatgg ttcccaccta gcacagttag   46560
ctcatcatcc agtaacttgt ttttgcagtt tttatttta caatctggca tagtattgac   46620
atccttgcac tccaaaccag agctcattag aatgagttgg cctttggtaa aattttccgt   46680
caattaattt ttttttgcca tgaatttctt tagtagaaca gatttgtttt ttaaaatacg   46740
tagccttggt tacttatcca cttaacccta ccaataggga atactccctg gactctgagc   46800
ctggttcctg cttttctagt ttccagtttg catgtaaaca tttaatgtat attcaaattc   46860
ctagtggtct tctaatcttt tgtctgtctc tgttttctct tgctccaaa ctgtcttccc   46920 atactaatct tggtattttta ctaccaggtt ccttctctgc tgaaacacat tcagtgttgc   46980
```

```
atcaccactt acgtaagtaa gtcaaaccag actgaattta tagaaattat ctagtttgcc   47040
ctctttatct tacagacaag gagtagaact tccacagaga tgatgctatg tgtctaagca   47100
gaagcaactt gctgtggagt tctgatggta gaactgttcc tactgtacct tactacctac   47160
catttgacct ccctagctca acatttggag ggtctctctc aaaggcagtt ttcctggaat   47220
atttcttatc tcttaactgg tctccctaac acattatgag ctttcccatt tcttttgcctt  47280
tgcataagac ccttcctcta tctagactgt cccactccct cgcatttagt attaatagaa   47340
attcatactc attcacatac catgcctaac taagcactta gtattttata tgagttattt   47400
tatccttata aatccatcag ctagattcta tatgattccc atgtgacaca tgtaaaaatt   47460
taggctgaag tagatgaagt gacttgccca agacttctga gttagtaggt ttcagggcca   47520
ggatccaacc tgagtggtct gtctccagaa cctgtgctat taatccatac attaaattca   47580
ctgcctctaa ggagtatttt ccaagttgca ggccataggc tccctctact ctgtgaaact   47640
ttccacagtg atatatatca gagaagcaga atttatttca tggttatctg tgctttctgg   47700
aaggtgagtc aatatactac ggggttgaat atttcctacc caaaatgctt gggaccaaaa   47760
gtgtttcaga tttcatttt ttttttcaga ttttagaata tttgtggttt ttctttttta   47820
atatactttc aactattatt tttgattcag cagctacatt tgaaggttta ttacttgggt   47880
atattgtatg atgctgaggt ttggggtatg attgatccca tcacccaggt agtgaacatg   47940
gtacccaata ggtagttttt ttaaccctgt cttcctgctt cctatctagt tgtccctggt   48000
atctattgtt gccatcttta tttccatgag tatgcagtgt ttagtcccca cttgtaagtg   48060
agaacatgca atatttggtt ttctgttcct gtgttaattc actgacaatg atggcctcca   48120
gctgcatcca tattcctgcg aaagacatga ttttattgtt tttttttgtg gctgcatagt   48180
attccatggt gtatatgtat cacattgtct ttattcagtc cattgttgat aggcacatag   48240
gtcgattcca tgtcttctca ttgcgaatag tactgtgatg aacgtacaaa tgcatgggtt   48300
tatttggtag aaggacttat tttggatata cacccagcaa tgggattgct gggttgaatg   48360
gtagttctga attctttgag aaatccccaa atttcttttcc acagtggctg aacagtgtat   48420
atgcattccc ttttctctgc agccacacca gcatctgttg tttttgaca tttttttaaa   48480
ttatacttta agttctgggg tacaagtgca gaacgtgcag tttgttacat aggtatacac   48540
gtgccatggt ggtttgctgc agccatcaac ccctcaccta cattaggtat ttctcctagt   48600
gctatccttc gcctagcccc ccaatacccca acaggccctg gtgtgtgatg tttccctccc   48660
tgtgtccatg tgttctcatt gttcaactcc cacttatgag tgagaacatg tggtgtttgg   48720
ttttctgttg ttgtgttagt ttactgagaa tgattgtttc cagcttcatc catgtctctg   48780
caaaggacat gaactcatcc tttttatggc tgcatattat tccatgctgt atatgtgcca   48840
cattttcttt atccagtcta tcactgatgg acatttgggt tggttccaag tctttgctat   48900
tgtgaatagt gccgcaataa acatacgtgt gaatgtgtct ttatagtaga atgatttata   48960
atcctttgtg tatatacccca gtaatgggat cgctgggtca aatggtattt ctggttctag   49020
atccttgagg aatcgctaca ctatcttcca caatggttga actaatttac actcccacca   49080
acatgacagc cattctaacc cctatgagat ggtgtcttat tgtggttttg atttgcatt   49140
ctctgttgat tagtgaggtt aagcaatttt tcatatgttt cttggcccct tgcatatctt   49200
cttttgagaa atgtctgtgt cttttgctta cttgttgttt atggggttat ttttgcttg   49260
ttgaattgtt taagttcctt atagattctg gatattagat ctttgttgga tgcatagttt   49320
acaaatattt tcccccattc tgtaggttgt ctatttactc tgttagtagt ttcttttgct   49380
```

```
gtgtagtagc tctttagttt aattagctcc caattgtcat tttttgtttc tgttggaatt   49440
gcttttgagg acttagtcat aaattattcc ccaaggccaa tgtccagaat ggtgtttact   49500
aagttttctt ccagcatttt tacagtgtgg ggccttacat tttaatcttt aattccttt    49560 gagttaattt ttgtatgtgt tgaatagtag gggtctagtt ccattcttct gcatatagct   49620
agccagttat cccagcacca tttattgaat agggagtcct ttccctattg tgtatgtttg   49680
ttgactctgt caaagatgac atggcttgta tgcatgtagc tttattttag atttcagatt   49740
agagatgttc aatctgtata aatgcttaga aagtaatatt aacacaataa tttattaagc   49800
gaccacaaat atctacaact tgactttcta agttctcttc caaatgtaat tagaaggaaa   49860
ccaatgaaaa ccaaggacgt aataatggga tactgcgcta taggtagatg tgctgagccc   49920
cagcacacaa agccagggtt tgcatcctac ctgcaccagt tactcctaat gcgtgtacct   49980
tggggatacc ggttaacctc tctgagtttc catgacctca tttgtaaaat aagcttaata   50040
taatctctca tggggttgtg gtagagactg tatatgaaaa cttgttttaa attataaagc   50100
acgtttcaaa aacagtatta ttttcagtc tcaccagaaa ttgaatatca gtaaatcagc    50160
ttaacgaata aattacttta ttattataca ctgccctacc accagtggta gaatgtagat   50220
ttcagtgttt ttatcaggga acttcctata agccttcttt gaaccaatat tgtatataa    50280 attattcatg aaatggaatt ggtcaccata ctctttacat tttctttgct ttttagacat   50340
atactcagat cccacacttt ctaaatacta atctagttga ttgtattttt gtatttttaa   50400
aataatataa attatgctta agaaagggct ggattgttaa gcagcttgtg ttcagaatac   50460
ctgccacttc ttgctgcgtt tttctatctg gaatgccttt aatttacctg gtttattcaa   50520
aatgagatag aatattgctg cttacttatc gctttcacat ctgcaacagg tctgctctgt   50580
ctttgtcact agggtttaca taaaatgact agacgctttt tcctttcaaa gatgaggatg   50640
aagattaaga agagaaaaga aattatgaa gcttggtgga aagtttgaga ggaagaaagt    50700
taagtgtaaa gaataaggga gttaacgcca aaaataaatg aacaaaaatg ccgtcatgtc   50760
tggcagctca ggtgtgtttt caataagcag caatggaatg gacacggtgg ctcatgactg   50820
taatcccagc attttgggag gccaaggcag gcagatcact tgaggccagg agtttgagac   50880
cagactggcc aacatagcaa aaccccgtct ctgctaaaaa tacaaaaatt agccaggtgt   50940
agtggtgcgt gcctgtaatc ccagaggctg acacatgcga ggattcctta gcccaggag    51000 gtggaggttg gagtgagcca ggattgtgct actgcactcc agcctgggtg acagagtgag   51060
actctgtacc aaaaaaagaa aaaaaaagca gcaatgattc taatattta tttagggtgg    51120 tatgaagaag gttgatggtg aagattcaca agtggaaaat acccagaaca agtgcccaga   51180
gggtgtagag tgtgaaaata tgtagtggag ctaagagaca agggaggctc ttctctccag   51240
ggacctgagt tctagtctag acttaacatg tgatggctgt gtgaccttag tcaaggcact   51300 tgacccttc tagcctcagt ttcttcatct gttaaataga ggtaatatgt cagcgggatc    51360
tgaggataaa ttgtaataat gcagcccaag cccatagtga gcacagtgcc tagcacatag   51420
taaatatttg atacgtgtta gacactgtta ctattttatg attatgtgaa cttagggaag   51480
aggaaccata ctaagtgcct cagttcagag ctgaaatgag tgtcaggtgg cattactgga   51540
agtaggatgg tagtaagcac catgagatca gttactatct tagctcccat gtgactactt   51600
atgcccatgc ctaaattcat ttatcaataa attgttctca gattctagaa gctattgaca   51660
agaccaagca gaatcataca gaaaatgtta tggtaaactt gtgcgagatg acctagtcta   51720
```

```
gcaaacatgc acatgatctt agcttctat aaggaagata aagtttttag agacaaggtg    51780
aaggaaaaaa taagtctaca aagcaagata gacccttgaa gatgtaatgg tgcaaaacta    51840 cttttttaata tatgttatct taatacccaa tggtctaagt cagttgttgg ctaaattatt    51900
catctgggaa ttttaatggt gacataagag aaggttgcgg acagcaaagt tggtacagtg    51960
tgtaggaagg aagagaacct agaactctgt aacttactag ggttatatgc ctccaaagtc    52020
agttgccggt atagctctca gtaaagaaca tggattgagt gtttataatg tgtttggcac    52080
attcatctgt cttaattcta aatgaccatt tgacataggt atcttgatct tcattgtata    52140
aatgagagga accaacatac agagtttaga tttgtcccag attcctttgt cctaaaccta    52200
ttgcttattc acttatgcca gaatgactga tgtaagtaag tcagacgtta tttaaagcct    52260
tcaaaagaac ctaggcaaat atttgagact tctcaaatgt tcagccgaag gtaagagaat    52320
taagttacat cacaaaatga atcttctaa attatttctt ataaagcatt tgcatctcat    52380
aagtagcatt gttttttga agtttcactg atcattttt aggttcaaca taaaatagtt    52440
ctcaaatttg ggtgcacatc ggaatcacct ggaggacttg ttaagtaaga ttcagtagct    52500
ctggtatggc ctgagaatat gcatttctga cagattccct attgctggca catcactttg    52560
aggtccacat tttgagaacc actgacataa aaagcatgta ttttatgatt aatcctatgg    52620
aggaacaagt aggaaaatag tccttgaggg gaattccaag atcacaggtg gaagctgaaa    52680
ttcagatcat gttttccaaaa ctcagtaggt tatacctagc caggcataac tgaatttgga    52740
gtctaaaaga tctgtattat cactttttta ttttgaagga tgccttttga ttacagaggg    52800
aaatcaagga ttaaaaatca atatacatgt aaatattgaa attcattggt aacttttaaaa   52860 agcacaacag ttttgtgtgc ttttctccaa agcactacaa atatgattaa ttgatgtata    52920
agaattttct tatggaattt ttttttttgt ctctgtaggt ggcaaatctt ccaaaagact    52980
acatgataac cctcaaatat gtccccggga tggatgtttt ggtatgtaaa ctacatttct    53040
gagtttcatt ttagtagctc atagaagaaa tgggatcatt catattgaga tagtacacta    53100
gctgctattt aggagcttgc ttattgtcag gatttgaaga atttatcttt ggaatttgac    53160
ttgcaggctt ttttttcccc ctcttaagca actgttaaac tttatcagtg atcatttcag    53220
cacatatatc ctagacctgt atagttgttc ttcactatcc ttaggaaatt ggttccagga    53280
caccttccga ccctccatcc tccccactca ctccaccatc aggatacca atcctagga    53340 tgctcaagtc atttctatga atggcatagt atttgcatat aacctatgca cattcttctg    53400
tatactttat ttttaaattt ttatttttca ccatggaagg cacactggaa ctcctgtgtg    53460
ttccaggagt ttagttccag gaatttggaa ctaaattaaa ttatttctaa attaattcta    53520
aattaattct aatactgaat ataatgccta tattacataa atcattgtta tgctctgctt    53580
ttaaaatttg ctttatgttt tcttattgtt tgaatatttt ccatctttgg ttggttgaat    53640
ccgtggatac agagggccat ctgtacttcc aaagtaaata cgattatctt ctttagacct    53700
agccacagat tttctcattt tccttaagca tcccctaaa aaaggacttc agtgtaagtt    53760
tatgtaaatt cttttcata gctgacctac ctcacttgtt taatttgaaa gcacaatttg    53820
atttactagc agtgcaatag attccttagaa ccttacaaca agtgtatgtg tttactatta    53880
taagtactac tctgttgctg aaaccaagaa attttaatta ttttctcat tacacagtat    53940 cagaattcat acattaagaa atatttcaag catagagaat aatgtaatat ctgtatacct    54000
atcacagagc ttatcaaacc ttccattgt gcaatatttg cttcaaatat atttttaata    54060
atgaaacatt acaaatgtaa ctaatgccct atgtatgctc cttctctgtc ttcattaatc    54120
```

```
cccagtttgt ctcttagtgg taacacttat tctgagctgg acttttttcat tccaatgtgt    54180 gctttcaggg cttgtaatgt ggacagcatt cactagtgtt atgtagagca ggaggagcat    54240
tctcttatat gtttactgca gtgtatgcac ccatacataa gacatggaac tttttgaata    54300
tttaataatt ttatgttaag cttctatact ttgaagttcg cttatatctt tcaacatgct    54360
ttgacaagtt gttttatgtt gactcatttc aactactgta ctgtgtttct tgagtaaatt    54420
taaaaccatt tgagttactc tcttctctac aactctcatc tttccataat ctaccaaaac    54480
ttattaaaca tctactttgt gtaggttttg accaattttt gtggatcagt ccatcaaagt    54540
tgttaccaat ttaaacacat cattatgtgc ttgtgcttaa aatgcatttc aaagactaca    54600
aggctgtcat ttcaagagaa tgtcaaagct acatttcttt ttattagtaa gcattttagc    54660
atgaactacc taaagttttt tttagaattc cttagaacat gtatcttcat gttgaaccat    54720
ttatcctcaa gcctatgtca atgtctatcc tattgagtta gggggagttc tctggaaata    54780
gaaatggaaa attattagca gcctgaaagt taattaattt tattatttgg ttactaagca    54840
agtatttagt taggaaaaac taaccaggag ccagcacttt ggcagacact tgaagaaaca    54900
aacacacacc aattaggcaa tgatctttag ttcaaaaagt ttagtaattg ggaaggcagg    54960
caggggggat tatgtggcct ttttataaca ctttttccatt tgcaaaatga tttcacatat    55020
taattttctt ggctgattag aaaaactctg aggaaggtaa aatagctatt atgattccta    55080
ttttacaaat gatatattga gctttacagc gcaaaagtat tttgcccaag gctatacaat    55140
tagaacgtga cagagtctta aaaagaaacc cgtaggtcat cagactctta accctgggtt    55200
acggaaagtg aggatctata taattacaac acttagggaa agtgtttgaa gggaagcctc    55260
taggtaataa agacccaccc cagatccttc ctgactgcag cagcatttag gattgtgatt    55320
gccaagcacc caaagataac ctgctgctct ttgaaaaaca aatgctaaac tgaaaacaac    55380
taaatagaat ttttttgtgct ggtataatca tagaatatgc taaatcatag atttcaatgt    55440
cggcttgtga tagcaagagc caagcttgtg aaaataaagc tgattcactg ccacatattt    55500
tgtgcttgtt tctgtaattg agaaaaatct actattgatt ctggcatgct atactggcac    55560
aactggagaa acactgttct tcttggccac caccatgggc aagaaaaaca aggccacgtt    55620
tagagcattg gacagaacca ggggtctcac ccttttgtttt accttcatttt tgacatgttc    55680 gtttctgcga agaccagagg agtttcccag tggggaggcc tctgattatt tgcgagtggt    55740
cagagtccca gctgccttat cttttgtctt taaacaatag agggtggagt gggaatgggt    55800
gccaaaaaga ttctctggtg ccaaagcaat aaaattctgc ccatgggcac tgggcagaag    55860
aaagctctag aatagaatac acttttattt ttatttttat tttgccttca tttttaaaaaa    55920 cagctaaatt ctcctagaaa agggagttca cttttccaag gtccttctta gaaaattacc    55980
tagcagattc tgtctcacaa atagcagggt gtgatcaacc acttagtatt taaatctaac    56040
gataatcacc aatgctattt taaactcttt gaaactatta tattgccgga ctgttgaaat    56100
ttcctttaac ttcctaacct taaagaatac ctggatattt ctggtctttt acatttactg    56160
gtaatgttat tgtagaaaga ataaaaatgg cattgctgaa ttgttgccac acaccttcat    56220
tcacttgaac ttccatagca tttacataaa ctgtgggttg cttgtaatat ttgagtttaa    56280
aaatcttcat ttttaaaaaa attttttttat ttttagctat tatggataca taagagttgt    56340
gtatatttat ggggtacacg tgatattttg atgcaaccat acagtgtgta atgatcaaat    56400
cagagtaact ggaatattca tcagctcaac tttacaattt ctttgtgtta ggaacattcc    56460
```

```
aattccactc ttttagttat tttgaaacag acatttttat taactgtgcc acctatttttg    56520
ctactgaaca ctggatctta ttcgttttc aattttact taaagtatat attcatcagt       56580
tttcttttag ttttttattt gcaaataatt ttaaatttac aaaaacgttg caagaatatt     56640
taaagaacac ccatgtgccg tttaatccag attcacctat ttcaagtatt tttaacattc     56700
tgcctcattt gctttatcag ttgctttctt tctatgtatg catgtgtgtt ttattatgtt     56760
tctgaacttc ttgaataagt tgtatactga tgcatacatg gccatttact cttaaatact    56820
tcagtgtgta tttcctatgt gaaggatatt ttcttaccta aacacagtac atttgcaact     56880
tcaacacatt ttacaataat tatagtactt taatctaggt ctgcatttca atttagcttt     56940
tttgttttg tttttgtttt ttgtttttg catttcttttt ccttcagtat aagatcctat     57000
ctaggattgg aattttcatt ttgataccat gtaaataatg actcccaaag atgccttgtt    57060
ttgggaatat attacctgac atggcaaaaa ggactttgca gatgtaatta aattaaggat    57120
ttatagatgg aaaagttatt ttggattatc caggtggtcc cactctgatt tacatgagtt    57180
cttataaaag ggaggcagga gtgtcagagc cagagaggga gatttgaaaa tattacactg    57240
ctggcttcaa agatggaaga gggattcaca agccaaggaa cgcacatggc ctctgaaagc    57300
tggaaaaggc aaagaaaatg attttccctt tacagcatcc aaaagaaaca cagccctaat    57360
gaataccttg gtattagcct attcagacct attttaaact tctgacctcc agaactgtaa   57420
aataacaaat ttgtgctgct ttaagccacc aagtttgtag tactttgtta tagcagcaat    57480
aataagctac tacatcctgt ctctctagtc tcctttaaga tttcctcagg cttctttgt    57540
ctttatggca ctgacatttt tgaatgagac agtcctcccc tttaagaaaa gtgtttctct   57600
ttgcaacatt tgattgatgt ttcttaatgc ttctgtggag cttatgcaat tcaagtgaca    57660
atgctacgaa agtgatgatt tgtgctcagg taaccacatc cagaggcaca cagagtccat    57720
cctctcctca tggtgctgtt tgttttgatc atctggttaa gatgttcaac tgtttatgta    57780
tatttactca ttcacaattt ggggagagac actttaaggc catataagca atccttctcc    57840
ttctcaaagt ttctcccaca gatttagcat ctattgatga tacttacctg aaccaatctt    57900
tgctatcatt gtcagttttt cgttcagact ttttaaaggc acagctaaat atggaagtga    57960
ttggcagcat gtgatgccac tctaacaata agccttccaa acttcttccc tcttcagtac    58020
ccttcctcag gtatgcacaa tttcacttct tggctattct catcttttt tgcctggccc    58080
tgttacttac ctctgggctc tttccatttt ctttgatacc tgaggattta ttatttgatg    58140
ttttgattct tcctgaatag acagagtgat ttaaaagaa atacatccaa tcatttcatt    58200
cctgtttctt tatattcatt gaatggcttt ttgctgctct taggaaacag gaaaaggagc    58260
tgcttcaaca aggcctccaa gactgtagtg atctagctgg gcacagtggc tcacgcctgt    58320
aatctcagca ttttgggagg ctgagacagg tggatcatga ggtcaggaga tcgagaccat    58380
cctggttaac acagtgaaac cccgtctata ctaaaaatac agaaaattag ctgggcgtgg    58440
tggcgggcgc ctgtagtccc agctactcag gaggctgaga caggagaatg gcgtgaacct    58500
gggaggtgga gttttcagtg agccaagatt gcaccactgc actccaggct gggtgacaga    58560
gcgagactcc gtctcaaaaa aaaaaaaaaa aaaaaaaga ctatactgat ctggcacctt    58620
tccacatcct ttttcagtcc tttatcgtta tcgttaccag ttccttgctg ccacatagct    58680
tcttgcctgg ctttctctat tcctggaatc ctgattggtt cttttgtcta gctaacacct    58740
gattctttta gattttggtt ttgattttg atgaaaccaa attgttctac tggaaactct    58800
tctcatcgca ctcctcagag tagcagtttt ggatgtattt gtgggatgat ttaatagata    58860
```

```
atcttccacc aacctgtaaa cttcacaaag gtaggaacta tattcttttt gctctgcatt    58920
agattctcag tgcctcatgg atgctcatat gcatttaatg aatatttgct gaaagaaagt    58980
gaagaaagga aggaggaaga aaatttccct accatataat catttgtaat ttccttgagg    59040
cacagatttg aacttagttc acaaggttat aatgatgagg tgagtgccta aactcgtca     59100 cacagtatct gcactgcaac gttattatct tctttagat acgtgtgaat tttttgaaat     59160
attttaggtg taagaattgt attatgcaat tttggggaat cacagcttct ttaagccttt    59220
ggttctactg ctttaattga gttattttg cattcaagaa cctgcttatt gttcccattt     59280
actaaaggct gagagccaga ttcctgaacc taatgttcat gactctctgt aatccttccc    59340
taccctaacc aactcatctg aatacccatt attccccaac acaaacttgc cacctcagcc    59400
acatgcatca ctgcctccta aaataatgcg cctgttctca aaggatgccc tttcttctcc    59460
catccactta tccaaattct acccatagaa tcatgcaata tcttgggct taacccatct     59520 tagtggtcat ctcctccaag gtcagtttaa gattctctt tcacacaagg acattttctg     59580
ctctttcagc ccacattttc tctcccatgt atcatttgat caggtgctac tctgtgctga    59640
gtgttttgct tgatgctgga gcttggtggt cagcaatact atcattgcac ctgctatgtg    59700
gaccctatct tttagtttat tatcttgtga cttctatgga atttgtccag aagctattca    59760
tcttgggtac atgatcatat attgcttaca tagagcttaa tattttaagt gttatatatt     59820
tgtctcaaag tattatcgtg agaaataatt aaaatacaaa aaatatgagt tgtggtgtgc    59880
atataataac atcagatacc atcattatta ttttgttgtt gtgttctctt tttactatat     59940
tttgactatc tacagagcaa ggttgaaatc ttttactcct gtgtatctcc tcaccattct    60000
ttagacaatc caatgcatat agtcgctcct caaaaaatag ttatgaataa acatttaact    60060
cttggcaaaa atgctagatt tccaaatctt gaaggagccc atcttattag tttagattcc    60120
tgtggttttc actaatagta aaagtcccat tattataagg acactaaaga atagcatgtc    60180
acctaagggc atgggtgcaa caggccccat gaaaagactg gaaccaggat tggaaactat    60240 cagttttcc ttctccatct ctgaatctct gtttctccgc ctcattctat tgtgcagat      60300 attttctcct ttgttccagt cacttggtag aatgtaactg cccaagagct gccaggttta    60360
catatttcaa tttcagccct attcagagat taattatcag tttctaatga tcaataccaa    60420 tttggggag gaacgttctg gttggcctat ccaagtcagg tgtctaccat catccaacca    60480
actatggcta cagggaaagt tcaccgtttg taagcatgga ttctgaggct ccactcctat    60540
gatgcggcat tctctctata aaatagacg tcagccaaat agacacttgt agtcaactat     60600
ttatctgcct cgatctccca tgtaataaga agtatttat ttaaaaggaa taagcataaa     60660
atgttagttg aatgaataaa atatgacatt aaatgctatt ttaagtagtt cttttgtata    60720
ctgtactaca gcacagggc ccgtcttcct aataagtgat tatattaaga tgctgttcag     60780
attatctagg ccattattct ctgatagaaa tacaatggaa gccacgttca taatcttaat    60840
tgtctggtag caacactaaa aaaaaataa ataaaaacga gcagctgaaa ttaagtataa     60900
tgaaatttat ttagccccat gtatccaaaa tattgtcatt tcaccttaaa atcaatataa    60960
aaattattaa tggaatgttt tatatgtttc atattattca aaatccacag tgtgttttac    61020
atctgcaaca tattacagtt catacactaa attttcatta gaaatagtta ttccatattt    61080
agatttttta ataaaattta ccattgagaa gatagtcaca tttctgtgtt ttccaaacat    61140
acttaaaagt tccagcctct aaatagggtg atattattga cttttcaatt taagaaaatt    61200
```

```
ataattaagt aaaatgaaaa ttttagctct gcagtcacat tcaatgcatt ttgagtgaga    61260
ggagctgcag atggatagtg ggattcccat attggccagc atcgattaga atttatttta    61320
tagatggaga aactgaagcc ctgaatagat taaatgactt gcctgaaatc acaaagtgaa    61380
ttgacagagt tgggactaaa aactgggcct ctagttcatc gttgctgccc tcactcccca    61440 aaccctgtg ctgttccttc actgttctat tttagggcgg gcctaggggc catttatagg     61500
tctgccctgg gaaataacac atatttagag tgctttggtt gattaccatc ttaatcagat    61560
tgagatttct acggcacttt aattcaaaca agaaatgtaa agttagatgc ctaaagtgaa    61620
cactgaagac ccaaattaat tgtttaggga gaggactaaa ataaatcatt acaaaaccca    61680
gctaatccaa agagaagtta agatttcgga gactacactg gcaacatgaa catgcaatat    61740
tttgcaaagt gcttttatag gaaacttta aatttgcctg cccatggaat gtttgagagt      61800
agaatgtcag ctttctagcc acaacgaaaa aaaccaaaag aacagtaaat aaagtccaca    61860
aatggcaatt gtcacaattc ctcagagaaa tttaccttca ttggtatgac tctggattaa    61920
ctgaaatgaa acagaaagaa ccatttctat tccaaagaga tttcttaatt gagccgaaga    61980
atcgtgtctg gtccagacgt gagaccacat gggtcatagt gaattcagca gaaaaaaaca    62040
cttcagtttt atgtgctttc actattctca tggctactag aacaaaatga gtgatcgaga    62100
gtcctggttt ctcgcgtttc tgtgtaaatt tgttatgtaa cctggaacga gacacttcac    62160
tactctaagc cttgattttc ccgcttatac aattggtgag actggtcctc agtattcctt    62220
ctaggtctgg aattctggtg attctgatga catggctcta gattttgatt gcacatccca    62280
gaggtagatg ctgaaagcac aaacagaaag gtacacttcg tgccctaggc atgcatacgt    62340
ctaattccag caagactgaa gtttgacacg aattaaagaa agtaaaacaa aaacaaactg    62400
ggtggtaatg ctggtattta gattaatcag attagaaggc tgggtgaata ctccttatga    62460
atattcttag aaacctcata gtttatgagc caggcttttc actctgagaa tctctaattg    62520
gtatttcacc aactcctgtg aaaagaacgt tctcactggg tagatactag ctttaggccc    62580
tataagaaag aacatagata tctctctgtg aatagctacc aaattgaaag taatgtaaag    62640
tgcttcagtg aagaagtgtt acagtattat tttgtctact ttcagcttct taatccgtaa    62700
atcttaccgt gactgctctt aaagactgtc tgtggggtgg gcgcggtggc tcactcctgt    62760
aatcccagca ctttgggaaa ccagagatggg tggatcacct ggagtcagga cttcaagatt    62820
agcctagcca acatggtgaa atcccatctc tactaaaaaa acaaaagtta gctgggcgtg    62880
gtggcagatg cccgtaatcc caactactca ggaggctgaa gcaggagaat cgcttgaacc    62940
caggaggcag aggttgcagt gagctgagac cacgccattg cactccagcg tgggcgagaa    63000
gagcaagact gtctcaaaaa aaaaaaaaaa aaaagactg tgcatctaat accaatgtgg     63060
aataatgtgt caaattattt cacctaataa accagcacag tttcttgaat gaggcaggag    63120
atagagagga gaaagcatgc cagaattagc aagtctccag gatgatttta aaacacatgg    63180
tttatttcag ccggtttctc aaatttactg gttctggaac tacagagatt ctgtgtcaca    63240
tattctgtgg aattaatata ttacctttta aaaatttatg cttagtctta gaatgtgcat    63300
atatttctgt tgttggtctt tggaaacagt catattccta gttatgttta gaatactttt    63360 aatttattc attttaaatt atatattta tttaatcatt tagcgagatc atgatttggt      63420
gttcatggta ctttaaaatt cctaaggaag ttcacagttt ttgactgaat tgtcagtggt    63480
agtgagatgc tagcagtcca atatcattga gtcaatatca ttgagtcagt ttggattcta    63540
gaataataac atgttataag tacataggga tagaaagcac atgttttag tagtcctagc     63600
```

```
tagagctgct ataattaacc aagaaaacat aagacagaag ctatcaagaa agaaggtaag    63660
aaattgagag catggagtca agaaaaaagt ttttacactc aaagcagaat ctatatgttt    63720
cttcttttgg aaacaataca tacaggcgaa taaagcatca aattacatgc acatcaggaa    63780
tttaaaagca atcatttgtg tcacctttga catcctgtat gactgtcaat tttcttaatc    63840
ctttatattt tctagtgaaa gagagaacat tatatcttac tttcttctaa tgaatatcat    63900
tgagtaaata tttatataaa actatttaag tttaaaatat ctctgaaaaa taagaaacag    63960
tgataatatc atttattaag gcaaacaaaa agtacgtttg taaatttgac aatctttaat    64020
catttatttc ataatcataa tcgtggagga attgaaaaac agaaagacct gctatcacct    64080
cacaaatgaa atacttagtt cattgtgttt tattctcctt gcaaatcatt gacgatattt    64140
aattaaaaat tacaaaactg ctagacattc cagtcaaaac tagtttcctc tcttacaagc    64200
aggcagatca aaactgactg acatttaata ttatttgttt accttcattt tatctttaat    64260
aaactcaaga atcttaaaaa gccaatatat acatggttaa acaaattact gaaaaataga    64320
actttgaatt tatgattcag cctttttccaa agaaacaata gcacaagcaa aataaaaaaa    64380
tgagtgaaac atgattacaa gtgttttaga aatacacgat ttttcagctg tgtaggcacg    64440
tagtttatat caactatcaa caaattgttc atgactttag aagggcaaac attagagtag    64500
gattagattg tggaatttcc atggtttaac tctaagaaag cacaggattg gggttggaaa    64560
ttttactgga aagagttgat tgtttagact gttgatttag ttatgtgaaa atgggaggag    64620
gtagggtaat agctaaatag gaactagaat ataaaatgta aacatagagt tcggttgaaa    64680
atagtgatca acagaagtgg cagtaagtac cccagaattc ctcagcttaa aaataagaaa    64740
caaatcaaca aaacattttc tactttaacc acaaaaaaaa agcaaaatga acaaagtacc    64800
cattcatata agacaactac cacagaaact aaaggaatgt cttaattcaa aacaaggaat    64860
ttgattttgg ttcttacttg ccagagatcc taggcaagca tactcataaa gtgaggaaat    64920
agagtcctaa gagattaata cctggaattt cattgttaga aaaatttgca caatttcaac    64980
ggaatgaatt ggtgaaagct actctatcac ataaatacta ttcaaatagc aatttacagt    65040
gtatgctgtg ttccatatcc taggaaatct gttcattgtt gatagggctg acggtctata    65100
aggaattatc actccctaaa aggaaagaaa cttgcagagc aattcagcat ccaaggaaag    65160
actgacagct ttgaaagaga cctgataatg atgcaagtag gaacttgcat gtgcttgaag    65220
taagcactga tttaacaaaa caaagactct gttctgcaca tactttggaa acacatattc    65280
tttgagaact tggttatgac gagttgaaat ggccacttga actaaattcc catgttgaga    65340
tttgtttatc cttcttatct gaagccagag ccaacaatcc taaaagtttt gagtgacatt    65400
taatggttcc aggaattggg gcttacctat ctgcagataa acctgcttcc tttttggctg    65460
tattatatta agtaaaacag ttctgttaaa tgaatataaa gtggtccctt ctatacttta    65520
gaataaataa atgacttgag ccagatgcag tgactcacgc ctctaatccc agcattttag    65580
aatgctgagg agggaggatt gcttgaggcc aggagttcaa gagcagcctg agcagcaaag    65640
caagatccca tttatataaa aaaattaaaa attagccaca cttggtagca tgcgccttgt    65700
agtgccagct acttgggagg ctgaagtggg aagatcactt gggcccagga attcaacatt    65760
gcagtgaacc atgattgcac ccctgcacta cagcccagga ctcagagaga gagcctgtct    65820
ctgtaaaaaa ttaaagcata aataaataaa taaataaata aaaggcttga cttttcccac    65880
agagatattc tgctggtaaa tagagaaata aagcttagta gtttgattta ttttccatga    65940
```

```
catcagttac tctgagtaca atattttgt tacaagttgt attaaattat ttgtgctttt   66000
aatgagccaa ttcaatgtta ttcttaataa caatgttatt tttgtcactg cagcatttca   66060
gcagtgttca aaatacatca gagtttccac ttaaagatc tttataagag aaaagataac    66120
acattaaaat catataaagc atgcaaactt acaacctcct cctcctgtta caagagtccc   66180
tcctcctatt acaatagtcc ctcctcctcc tgtcacacta gtcccttctc ttcctgttac   66240
aataacccct gtcctcctat tacaacattt taagtaatgt aatattaatt ttaaaaatct   66300
ggccaggcac ggtggttcat gcttgtaatc ccagcacatt gggaagctga gacgggtgga   66360
tcatttgagg tcaggaagtt tgagacagcc tggccaacat ggtgaaactt cctctctact   66420
aaaaataaaa aagtagccag gcatggtggc aggcacttgt aatctgagct actcgagagg   66480
ctgaggcagg agaatcactt gagtaactaa aacgatagct ttgaagagta ctccgagttt   66540
tatggcactt acttattaaa atagctgttt tgtctctttt ttcatatctt gcagccaagt   66600
cattgttgga taagcgagat ggtagtacaa ttgtcagaca gcttgactga tcttctggac   66660
aagttttcaa atatttctga aggcttgagt aattattcca tcatagacaa acttgtgaat   66720
atagtggatg accttgtgga gtgcgtgaaa gaaaactcat ctaaggtaac tttgtgttca   66780
ttgggattat ttttcattac gcttctctaa aaacccatgc ttcttggtgc tgttgggggaa  66840 aatgaggcac ctttatttat gatattttga ttgtataaac ttcaaattta aaaatcttgt   66900
tcagatgagc aaagaaaaca agtatttgca gttatactgc aatactgaag tgcacattca   66960
aacttaaatg ttgtcatcta atacaaaaat aaaacttatt tacattacaa tgcaaaatca   67020
gtcctgcctt tatctttatt cttcataagt gaagtccttg aaacctttct attaagttac   67080
aagtgttcat ttaaatggaa aattgtctgt aataaacaca tatccttta tgcataatgt    67140 aatcacccca taggtcacag caaaggaata cattttggct cctcaaagtc attggataac   67200
tgatcatcac caacttcagg atatgggcat gacatatgga ataggcaatg tactccagaa   67260
aataagagtg agatattgga gtttaaattc tggctctgtc gctaatgagt tctgtgagcg   67320
taacttcttt gtacctcact ttctttatct ttaaaatggg ggcaatgcca gaattcatct   67380
aacagggtcg acgttaggtt atttgccatg agtactttaa caccctacct agcaaaataa   67440
atattaataa aatttgatgt ttttcatca cactgtgtct atagcaaaat catgcttagg    67500
agacctgatt tggtatacag ttcaaatggc caaagattag cttaggagac ttatgtaagt   67560
ttaaattcaa agttttaagc aggattctgt accttaatac ctaaatgctt tttcctgtgt   67620
cccatctaaa ttccagctat tctgtaagac ccaacttcaa tcccatttgt actatcctat   67680
cttataattc ttaccatact aataatccaa tcactacctt taatctttgt attatttct    67740 aatttccaaa gtcagaatgt ggtgttaacc actctttcat attactactg catatagtgt   67800
gccaatggca ttcaaaagaa gtagagatca caaaaagtag agtgcatcac acaaggtgtc   67860
acaaaggaaa taacatgtgc attagagcct taaagatgag ttaggtaaat gagttaggtc   67920
aatggtgatg ttgggaagaa cactgcaaac aacaaagaat gtgcatttac taatcatggc   67980
actttggtgg gaacccagga gattaccaat tatatttctc agttgttttg gagattgagt   68040
tactgtatat aaagcactta gaatagtcca tagtaagtaa cagatagttg tttattttgg   68100
ttacctactt ttcttatataa tccattatgt atccctacaa catagctttg atttgctttg   68160 gggaattta tattaatttt atatcaatta atcataccat tttattatt tgggacttg     68220 cctcttcac tcagctttag gtttagaaga tgtatccact ttaaagcata tagctgtagt   68280
taaccttctc ttgaattgaa ctccactaat tcaatatatc actagttatt aagccactct   68340
```

```
gtctggattg acataagtga tacagatatt gctgcaaaaa aactttttta tatgtctgat    68400
ggtatatatg tgcaatagtt tcagtaggtt atttacctga gaatggaatt tctgagtcac    68460
aggatggtca catgtctaac tttactggat aatatcaaat gtaccaactt acattatctc    68520
agcagtatgt aagagttccc ttgccaatat ttagtatcat ctgactttct aattttttgga   68580 tattagagca tgcattatgg tgtggttttt ttttttttt  tctaaagact ggaagttctt    68640
gtaatggagg ggtcttttaa aaataaaccc tcatgttttt aatgagcatc tctaaagaaa    68700
aatatcccca gcttgttttt aaggttattt attttatttt attttttgcc atgacattgt    68760
gttcactgcc ccagattcaa cttgtgatcc cactgggatc actaccctgc attaccaatc    68820
tgaattacat acgttaaaac agccatctaa aagtgctagt tgtaagagtc taaatacttg    68880
aatctttgag agacatattt atagtccatt atcttcacct cagttaagtc tgaagactat    68940
ttgaaaaatg taatcctatt ttttcttcta ggatctaaaa aaatcattca agagcccaga    69000
acccaggctc tttactcctg aagaattctt tagaattttt aatagatcca ttgatgcctt    69060
caaggacttt gtagtggcat ctgaaactag tgattgtgtg gtttcttcaa cattaagtcc    69120
tgagaaaggt aagacatgta agcatttcca gttcaaatgt aaacaacaaa cttaaatctt    69180
ccctatgtag taagaatcta cctctgtgtt aagctgtagc aagatacatg catgtacgtc    69240
taataaaaaa gcagatatca atagcacaga agaaactaat gattgtagat tgtgggttt    69300 ctaacccaaa gcaatattca tcagtttcaa attagtgagc tgtttgtgag taaacaatat    69360
atgagatggc cactcatacc ttttctcatc taatatttgc cagtaattac aattatatta    69420
ttctgtacct ccagtctact taatggtcct tctcaaattt tttcttaagg atctaactct    69480
aagtcacaaa ttctgatcct ccccagttac tctgtattaa gactcttttt tcccttcact    69540
gggtccctat aatacaaacc tggattcatt gctttctttt tttaatgaga aattaccatc    69600
aatgtgtcat tatttgtatt tattaacata tttattcaat aagtatttgt tctacaaggt    69660
gataatggtg gatttcttag taaaatagaa tagcaggacc cagtatgaaa taaataggat    69720
ctgaatactc tagatttggg aagcagacct ggcaagtaat ctggtattgc acttcacctt    69780
tcagggactc tataactcat acaaatcacc atataacact gacacattat tgctttctat    69840
ttagattcca gagtcagtgt cacaaaacca tttatgttac ccctgttgc agccagctcc     69900 cttaggaatg acagcagtag cagtaatagt aagtacatat atctgattta atgcatgcat    69960
ggctccaatt agcacctata ggagtattgc atgggctttc aaggaaactt ctacatttat    70020
tattattgat actgttctgt tactgttatt ccttttatgg tcttcttgag acttaagttt    70080
gtagaattaa atttccctag agctggagat aatgtttaga gaattaggcc aataaatttt    70140
ctgctgaggt tattttaaat aagacataaa attaattta  gaaatatgat ttatgccttt    70200
tgttgaatca ttaacatata ttctgtgtgg aatgtgtctg acaaaaacgg aagtttaaaa    70260
ttaagtgtat aaatgctggt tgttaacata tattctgtgt ggaatgtgtc tgacaaaaac    70320
ggaagtttaa ttgtataaat gctggttgta tagaattcca aagatatttt cagatttgtg    70380
tatatcagta tttactattg cgcatttgga aatttgatga ttttgttatt ttaccacaga    70440
attatatgct tgatgagaat aggcttattt ttctgaaatt tctgtcctct tttgccaaga    70500
acccaatttt ctttgaaaat ccagacaaag gtcattataa agtttattgt atttactaaa    70560
tactctctag cctcatggaa ggtgcaggaa gaataaaaac catcttgtga tctaggctaa    70620
aaaagtcatc cctaggact  tataaatggg gcactgtcat ttgttcaggg acttagaaga    70680
```

```
cctatctgtg aaaagaagta atcaatttat tactaattca taatagcttg ttacaatgca    70740
gaacatttaa aaaaactcta aaatacaatt tacttatttt ggaatttttt gccaccaaaa    70800
cctgacctga agtgatttga ggctatttat agtctatttz tctttctaaa agtgaatata    70860
```
(Note: line 70860 — reading "agtctattta" as printed.)
```
tatttactα atgaaatatt aatgtatttg attacagaat gctacccagg attcactggg    70920
gatagtatat gttatacatt atgtgcagga cagaatcttc tgaaacctaa aattctaaat    70980
tacgtagcat atcagttcta aaatgtgtca aaaagggact agagccctgt tgtgtgtta     71040 gtcaattaag ggttttctta ccaactatgg attttattaa cattttcaaa ggagcaactt    71100
ttgtcttctt aaattctctg cttatatttc attgatttct aatctttatt atttccttcc    71160
atttgctttg tgtttcattt actccacttt ttctagcttt tcgaagtgga aaaattagat    71220
cattgatttt aaactatttt tgctaattac aagcacttaa aggtataaat tttcttaaat    71280
acactgcttt agctgcacct cacacatttt tgtgttgtga ttttattatt tttctaaata    71340
tttgtcaact gtgatttctt ctttgattca tggataatat aaaagtgcgt tgtttgatgt    71400
caaaaagttt gagattttcc tatatatctt attgttacta gtctatgaat tttgttgtca    71460
gaaaacatac tctataattt ttttgaaatg tactgaaact atttatgta tgttatttaa     71520 ctgttgaatg cagcattcaa atttggccaa aatggttgat agtgttgttt atatcttccc    71580
ttccttatta agcttttgt ctaatttta ttaattattg agaaaaggga attgaaaata    71640
ttaacttttg attgtggatt tgtctgattt tccatttggt tttgggtttt ttgcttcata    71700
tattttaaag ctttattatt atgggcttat acattgatta ttgttagatc ttccctgttt    71760
aattgacctt ttaatcttac tgaaatatcc ctcattatct ctgatagtgc tttttgtctt    71820
gaagtttatt ttgtctgata ttagagcaaa tcttcttat gcttactgtt ttcatggtat     71880
atgtttggct ttccttatt ttcagtctgt tgtctgtatt tttaaagtac atctctagta    71940
gacaacatac acttgggctt cactatttta tttagtgtat ctctgattgt taattagagt    72000
gcttcatcca tttctatgta ataaatcatt ggtatagttg gattttaatc caccatttcc    72060
ttacttgttt tttatctgtc ccatttgtgt attgaccttc tgttccttat ttctagccct    72120
ttttttttgg ttaattattt tttttctagt gtttaattag tgttggattt tcaacagcac    72180
ccttttgcat tattttgtgg ttattttgga aattaaagta tacactttaa cttgtaatat    72240
tctacttaga gttactattg tagcacttga gaaaaaatg caagaacctt gaaacagggt     72300
agttttattt acccatccc atcttttgtg tcatcattga catatattaa catatctaca    72360
tcagttataa atttcacaat acagtctaca atacacaatg cagttcaatt atttctttga    72420
actgtcatac gtatttaaa gtaagagaag aagaaatata ttgtctttta tattaacctg    72480
catatttatt atttcctgta cccttcattc cctcttgtca gtccaggttt ccatttggta    72540
ttaatttcct tcaggctgaa aaacattcta tagcatctct tataatacag atctgctggc    72600
aacaaattct ttttctttt taattggaaa atatctttgt tttgtcttcc atgtagcagg    72660 tacttttac tagatattga agtctgggta cacaggattt ttttctttt agtctttta     72720 aaatatcact atagtattcc tgcagttatt gtttctgaaa aaataaaaa aggtagccac    72780 catttgtctt attttaccc tgtatgtaca gggtcatttc ttcctctgcg ttctttcaaa    72840
gtgttctcct ttttaacatt tgagctagaa tatgcctatg agtggttttc tttgtattta    72900
tctttcttga gatttgtcaa gcttttggat ctatatattt gttttccctc aaatttgggg    72960
aaaaaatagt cataaattttt tcaattttt taatccattt tatctatcct ctcattctga    73020
gatactactt gcatatatgt tagcagattg ctagtgtgtc ataggtcgca gaagttttgt    73080
```

```
tcatttattt atcctctttt ctctgtgttc ttctgagtaa tttctacttg tctgctttca   73140
agttcattga ccttttgttc tgccatctct gatctgctga attttcatc cagtgaatta    73200 ttctatttat gaatttatat tttctgttct agaatgtcca gttaattgtt taatgtattt   73260
catatttctc tgctggaatt ttccatctgc atactcatta tgaaaaaaaa ttcttttttg   73320
tcacttaaat ataatagctg ctctaaagtt cttgtctcca aatttcaaca cataggtcat   73380
ctcagagttg atgtctattg acttcttcct ctctgattag gggtcacatt tccttttaaa   73440
tggttagtga ttgtttaata tatgctggat attatgaatt ctatgctgtt gaatatcttt   73500
cagattctat agcgtttctt tagaggctat tgaattgtgt tttggtagga ggttcgaata   73560
gtagcagatg aggtttatct tttctcccag ccttgttttt aaactttctt gggtacaagg   73620
gaaagtagcc ttattcctaa ggcatggaat atctgagata tctgtaaagt gctcagaaaa   73680
tctctccaat attgcttgtc ttaataattt tgtccccatt gttctgtgtc tgctagggcc   73740
tctactaaga ttatagcttc ccatgagttt ggtgtttggt tatttttttt tattataatt   73800
ttattttttg gtcaggtttt gtgacttctc tactggtgca tatacagctt attattggac   73860
cagtaactta aggagattca tctagggatt tctgatgctc cttctttgca cagctcccct   73920
cttccaaata acctagatct agaaactcca gctgcatcgg cagccctgaa cttcaatctc   73980
tgactcctta gcttagtgag gccattggtc cttgtttgaa ctctgtcttc cacacctcaa   74040
tctgaaagtg caccccagac aggagagctg aaagccagaa aaccagggca aacatgagcc   74100
tcacttagtg tggatgccct gtctcgtgaa ttacacattt gtactgctgt tcactaattt   74160
ctgaaaagag ttgcctcata atttgtctag aattataatt acttaggttg gaaaggctag   74220
tctgctacca tcgtatttgg aaacaaaagt cttccctact aattttaaaa gacaaactaa   74280
atataaaata cctattcaat cccgtgcctc tgaatctgag attacttttt aaattgcaag   74340
atgaatggac agccttcttt tttgttcact gtttctttttt tcttccttttt taaaaaattt  74400 tgagtcttgc attgtcagca acttttagct aggtgatgtc actcatgaat atgccactta   74460
gatacctctg cacaggacaa gattttgtgg tgctaacatt cagagagaaa cagacgtaaa   74520
taaaatactc atagtacagt atacaatatg tatcataata gaattatgca aatgttttta   74580
ggtgtagcac aaaggggta agactttttt gggagaaggg ttagggaaat ttgaagaaag    74640
catgctagtt ttcagggata actcaaaagc tggccatgtc agagtaccag ggcatatgaa   74700
aacttattac agagatgtga gtgtgtaagg aaaagtcatg ggagaatgga ataacataca   74760
aacctattag ttatccaaag ggaattatgt ttatagcata acagtaatat cctttatgat   74820
aagcaaagag aatgtttaaa agatgtttta tgtttgagat tcttgcagac agtacctaaa   74880
tgatagagaa agaaatccta actttgacat tatcttatac attttctaga aatagtcttg   74940
acccaacctt cctggactca tataccagtc aagttaaact cttttgactc ttcggtcaaa   75000
tggaagatca taatacctcc ttcacagagt ttctgtgagt tttaagtgag ttagtacaca   75060
tgtgcttgga gacataactg atgtcttata agagttcatc attaagtact agaacaatga   75120
gatgcaataa gactttggat cagtaattat gttgaacctt tagtgagctc tggatctgaa   75180
tcaaggaaga atactcattt gcttgtttca taagcaccaa gataaccatg tcacaggcat   75240
ggtgctccta aaaatgctca ctctaaaaag aagttcagca aaattatagc acaattcttt   75300
gtgttctgta tttctacaga tgttggttat tattagtcaa atgaaacaag tcagttccca   75360
agatttctgg acagtgaata gttttggtaa taaggagata taattaatat ggtaataacc   75420
```

```
caggaatttg ggattactca aatccggccc agatgagctt cctctccaca taaattctct    75480
gcaggctatc tttgcataaa atcaaaactt tgttgtcagc ttaagttttg tccccaaata    75540
cccttcattt gggccttgag gcatgcaatt caaatctcat tgattcctac tcgatagctg    75600
cagtggaaag tattgaaagt cattccctgg aggtataagc aaatctcttc tgataaagtt    75660
ctttttgtct gcctgcaaga gggacagtag tatccctgat ggaccaaagg cctggttctt    75720
aagccccacg catgaacaag tgaaataaaa aaagtgaggt aacattgacc tctatgggag    75780
gtgaagctca gtaacctatg ggcgcttccc ccaaccctcc tctccactgc cgccccgcca    75840
tccagtcttt gctgtttctc tccctccctg tctcctgcag gaagattgct gctgtgtctt    75900
agtcagactc caggattgtg tattggctca cagtcttagg gatggaactg tcaacatggt    75960
agtcaccgca ctctcagaga gcaagtctga gctttcttta gtaaggcctc ccacacagct    76020
ttgttggaag cccttccctt agatgctatc cttctgcctg agaaaggttt taggtagcaa    76080
attccagaat atctcactct ttagtaagct gcttttgct tttgagtctg gtctttcctt     76140
tggtctgagt ggtgaatttc aagacttagg tttggtcttt gtatagaaca agaagaacat    76200
ggtgtttggc taccttgatt acagggcatc tggctgaccc aacgtagata atggagttct    76260
ccatagcatc ttcctagctt gttagagttt tccattggat tttaaggaca aaatcttaat    76320
taatttattt gttctctctg tgtacattga ttatggcctc ttaaggaggt tacctagtaa    76380
atctattgta attacatacc agcaatccca atagataatg ggggccacag cagattggcc    76440
ttcaaggaga accaaaacag ccaaatgatt tatttacaaa cagtattatt aaaattcctc    76500
aaatggtgcg aattgtttgt aaccctgaat ccatttcata tagagagcac ttttatagat    76560
agtagttaaa tcccaaacga gtccacgtaa tcttacataa tccttaaaat agctctgtta    76620
ttgtaatgat agtactttaa ttataccaaa tcccatttta ttactcagat ttattttggt    76680
gagaaaattc acattgggct ccaacttgag atggtaaaac atatctccca tgggctata     76740
ggatgtgggg tgggccagga ggaggaatcc taaggaggat attcatggtt atgtgaatgg    76800
aagaccctat ttctgacaac tccctacgtg gggatcacca gcaccttatt gttcatccct    76860
cactgtctcc tccccaaca cacacacaca cacacacaca cacacgtgag cacacatcca    76920
tacatcccat cattagagtc tccttggaaa cataccattt ataggatgag ggaatttcct    76980
gctctcagtt cacatatggt agaggaatgg gctgttcctg tcctcaccat agtagataaa    77040
atctatttct gacttatcaa gttaaatcta tgaattaatt tttccctgta agatgttgat    77100
acacacatag tagatctatt attttatatt atgtactcta ggtactttgt atgttaaata    77160
ggtataggta tatagaaaaa tctgtcaaaa taagtttcat gttggaagag acccttgtgg    77220
gagatgtgtt ttgtttattt aattcgtgaa tcattctgct cctttttttt ttttaaagac    77280
agagtcttgc tctgttgccc aggctggagt gcagtgacat gatctcggct cattacgact    77340
tccgcctccc gggttcatgc gattctcctg cctcagcctc cgtagtagcc gggattacag    77400
gcatgcgcca ccacacccag ctaattttg tatttttagt agagacgggg ttttaccgtg     77460
ttggctgggc tggtcttgaa ctctggatct caggtgatct gcttgactcg gcctcccaaa    77520
gtgctgggat tacaggggtg agccaccaca tccaacctaa attcatgaat cattttgctt    77580
ctcatggaag agccaggcag gatcaagaaa ggtgtcccaa accaattcca tatatgttct    77640
ctctcattga gtttcttatt tagacgtagt atgggacaac actagtgcct tcaaccattc    77700
cccttagtgt tagtcttaag cttttccaaca ttaaagtcc aaactcttag tccgttgcac    77760
agtggcatcc gacaaatgtg tgttgaagat atgaacgtgg aaacagccat gattctaagc    77820
```

```
atgagatacc taaaaatact ataaccacag tgcacataca attatttaat attttcaaca   77880
gtccaaacat agctgaatgc atacagatct tgatccaggt tgtaaaatgt catgtttaaa   77940
atttctgagc aagctgtcaa gagtgagaaa gcaaaaagat tttagaagat aaaggcatgg   78000
gagatagatt tgcttgatag tataagtcat tttcccccca gaaatatatt aagtctgtgt   78060
tccatatgtg tcagaattac ccaagccaga tctctttctg tctctgtgat ttctttcttt   78120
tttaatgcat tcatcttttg gagactacat ggatttatat tgccttgcaa agcaatatt   78180
cagcagaaaa atcaatcttt tgaatacttt aaacagatat aggtccagaa tgtgttacag   78240
aaacagttaa aaacaaccac agcataagag caaaacttct agaatggata tgctgtattc   78300
atcagtgtgt tctttaaatt atagggaagg ccaaaaatcc ccctggagac tccagcctac   78360
actgggcagc catggcattg ccagcattgt tttctcttat aattggcttt gcttttggag   78420
ccttatactg gaaggtaagt ggtaccattc ctttttttaa aaatatgcta tgtttacata   78480
aattatcatc ttttttttcct caagaaatga tcctttaaga aaacagtgaa ttctacctta   78540
gcttataatc taaacaaaat ttaaatttta taaagtttcc tgtttctcat tatgtctgga   78600
gacaatccct ctagctgata attcacgctt aagaattagg aactggtgtt aatagcctga   78660
actaaatatg aaaaggaaga tctgacgaaa atcatatgat atacttaaaa gacaaataga   78720
aatgtcattt gtattatctg ctattttgga tttctactct tttgttctct tcttattgaa   78780
gcctgtctaa aattttaaaa tgtgcaaaaa tcattgtgac tcagcttctt gaaatgtctt   78840
ttgaatttga ttaagtgtca gcttcttat tactctttag cccccaacat cctaaaaatg   78900
ttgagttgat agtaccatgc agctttcata attttttatt acaaagatat tttgcatgct   78960
acatgctgaa aaaactgtta ttggagttat tgccataaaa gataaaagtg gagtccactt   79020
acctcttaaa tattagacca ttcattgatt attttacagt atatgtcttt cttcttttc   79080
cagaagagac agccaagtct tacaagggca gttgaaaata tacaaattaa tgaagaggat   79140
aatgagataa ggtatttgt tttgctaaat gtgtgcccaa tcaagcatga cattgccatt   79200
tcacacactg tgtacctgcc cataatgtct ttaagaagtc cttcactcat gacagtagct   79260
cctaaccagt gagtcccaac tctatccatg tttctgatgt ctcactctct cttcagtgct   79320
gcatctccat ttacctacag aataccttca cataattgtc ttcatgactc ttcttagggt   79380
ttgtaaaggg gttacctctg ctttcttatt taagtaaggc agcagaatct tctcagactc   79440
ctggttgtgg aactctggag gcacatttgc tcatgttctg tcttttccac acttttatca   79500
aaacatactg attcagctct tggagcgtct tcctaagctt agttctttca gtaggaagca   79560
ttatcatcac tgacatcttt atgatctcat gagttgctgc cactgatctt ttctttagcc   79620
cttctaaact caacctttag tcacactctt ctgtaaaccc tggttcatag tgtgacttct   79680
tattcaaaat acgttcagtg attttctctt gtatatttta tatatcttt attttactct   79740
ggctttcaga gcccttaact attctcaaca tactcgttgt tttctctaaa gctgaataca   79800
aaatttgctg taagatgact ttccattcac tgtagctggc tcttgtcatt cttcaccctt   79860
accctatact gcccagcact catatgttcc cttacctttg attataattt tcatttggtg   79920
tgttgccttc tctcatgtca tgcctgtatg tatacacaga cacatatgaa atgcatatag   79980
gcatgcttgg tatgtgtata tgcatataca gagaaagaaa tgttttaact acttggaaag   80040
actaccttaa gacaaatgaa gtcttccctc ttccctatag taataagaag gtaggctccc   80100
cattcaattt tgcaatcttc tgctactata tttacagaaa agctgccttt tacaatgccg   80160
```

```
agatcatggt gtacctcaga atctctgacc aagagcaaat aagcattttt tcttattgtt    80220
tttcagtatg ttgcaagaga aagagagaga gtttcaagaa gtgtaattgt ggcttgtatc    80280
aacactgtta ctttcgtaca ttggtaagtt ttttttcttct ttccttttttt tttctttttt    80340 ttattatact ttaagttcta gggtacatgt gcacaatgtg caggtttgtt acgtatgttt    80400
acatgtgcca tgttggtgtg ctgcacccat taactcgtca tttacattag gtatatctcc    80460
taatgctatc ccttcccct ccccccaccc catgacaggc tccattgtgt ggtgttccct    80520
accctgtgtc caagtgttct cattgttcaa ttcccaccta tgagtgagaa cacgcagtgt    80580
ttggttttct gtccttgcga tagtttgctc agaatgatgg tttccagcct cagtcataca    80640
tgtgcatgtg tctttagagc agcatgattt ataattttat aatcctttgg gtatataccc    80700
agtaatggga tgcctgggtc aaatggtgtt tctagttcta gatccctgag gaatcaccac    80760
actgacttcc acaatggttg aactacttta cagtcccacc aacagtgtaa aagtgttcct    80820
atttctccac atcctctgca gcacctgttg tttcctgact ttttaatgat caccattcta    80880
actggtgtga gatggttatc tcattgtggt tttgatttgc atttctctga tggccagtga    80940
tgatgagcat ttttttcacgt gtctgttggc tgcataaata tcttcttttg agaagtgtct    81000
gttcatatcc ttcgcccact ttttgatggg gttgtttgat tttttcttgt aaatttgttt    81060
aagttctttg cagattctgg atattagtcc tttgtcagat gggtagattg taaaaatttt    81120
aattcaaact gaaatattta gcaagaacta tacagcatat gagatgccaa agtttagaaa    81180
caaacttcat tagtaagtct tctatcaagc agatgtcagt atgttggctg aagctgttac    81240
ataattgaaa tgtgcatatc taattcattg tgtattctcc agttttgaaa ggtaagcagt    81300
gtttgtcctg actagtggat tcatctagtg tgggatatgc acaaaaatta acagttgtat    81360
gtttacttag actgttttttg agaccagaaa attaattaga caagggaaat atagcaaatt    81420
aggactaaaa ttaagtatta ctaatagaat aaaaatatat ggaatcaatt ttatttaggt    81480
gtgaccacta taacatgact gtatcccatg tgttagatgc tgaaacaaga gaaaaccaga    81540
atgtttccct gccatttttca ggaaaaagag aaaacatcca aatatcttag agtcaggaga    81600
gtaagatttt ccaggtcaat tgccaccttc cacatgacta gtaataatta tgcattataa    81660
tagttcagag cccaggatgc acggaacata aacgcatggc agacaggtgc tgtgactgtg    81720
tgggtctgcg gagggattgt gggagaaagg agagtaagat gtggctagaa ggtactggta    81780
tcattatctc ctgtcccgtc tgctttctct gctcccttgc tgcagatact gttgcgggaa    81840
gacccacagc tgcattaact taatcagtat tgattcatgc tgtccctcac ttttgcttct    81900
gctaattggc tgttattttt gttactggca tggaatcctg agagcattta ccacagttgc    81960
atgcgaatat tctctcctct ttcaaattcc tcatttcttc tgtgcattcc ctcattgtca    82020
aaggattatt tactctcctc tttattacct agatagtctg tggtggattc cttctttacc    82080
ctgcaagtca ctgcccttcc agctttaact cctgtcccag gttcagagat ttgtctctag    82140
acttaatctt cttcagtgga actgagtcat aaattatctt gcctcctgta tgagcttact    82200
tttatggtta tacagcaaca ttttttaaca actcaagata acatgatata attatgttgc    82260
acatttctct aacactgtaa tacttttatt tacacactct gtcacttttta ccttcaatca    82320 tactcttgat taacatgtcc gtagcatgaa tagcaccctc tattttctgc tgcccattgc    82380
cacttctttc taggctcatt cttcctgtca aataatgtaa atggatagac cgtttgcttg    82440 acactttta ttttccgaag caatatttcc caagctgaaa ccatgctttt tcctagaaat    82500 tcatttttt gcctttgaac cataagatga gattcactgt tttcttttttt ttttccttcc    82560
```

```
ttttcttctt cttgacagcc atttcagttc tctcaagtgg cattcacaaa ccacacatta    82620
aatggttaat tgagtcttaa atgctcaaat gctcaagtaa tgtcctctgt tgtttggttt    82680
gggattgcat tgctgggatc ctgttttggc acacaggtct ttaatcatgt ggttttaatt    82740
acgacattcg tcccatgaca tttgggagtg gattaggata cggaaaccca ggccattgt     82800 ttaggaggaa aaagatggt attttaaagc aaccatagtc aaacaactta tgaatgtgtt     82860
gaatagtcag ttagcattcc aagaaaagag ttaggtcttt ctgtttcttg ctgtaccctc    82920
aacacctaac ttgctgcccg tgcattgttg gctctctata aatgtttgtt gaatgagaga    82980
ctgagtgagt gactcagccc taaatgaaag tttaagcaaa tggcaaagaa gattgttctt    83040
ctgaagtagg gtttgttttt atcttttgtg tgaatgtgtg tatttaatgt attgggttgg    83100
attaatgaga cagcaaggta tgcatatcaa gggggaatat aatcacatga gaaattaact    83160
aataaattat ttttcttaag gtatgaatta ttactcatgt ataaaatgaa tcacattagc    83220
caggttaaag aagccagaat tatccagaaa aaaacccagc tcacttattc agtagtcaat    83280
gggaaataga tggcagaatg aatgaaaaca tgactcattc tccttcacaa agtgccttac    83340
tcgtcatctc tgcaaagctc caccaaggct caggtcacat actgccacct acaaaaacct    83400
gacttcccaa atgaaaataa tctctatttc tggccctcta aatagatttc atatgacact    83460
tggtaggaca tcacagtcac ctaaatgaac attttgtgcc cttttcaaaa ccataaactc    83520 ttaggggggca ggattttttt ttcttaattt agttttggag ccccactaaa caatgtcact   83580
tatactgtgc acatataaat gatgaataac tatttgttga ataaattaat ggaaagatga    83640
atgaatatct cagaattaca ataagatgag aataaaatat atgaaaataa aaacagaaat    83700
aaacttgtat gtgtctatga gtacataaga attcaaatgc tgagggaaaa gtaggaaaag    83760
aggtagaaaa gggccagttc gtcctcagaa tctgaaaacc ccaaagtaaa aatgtgtgta    83820
tatcatttgt aatcatctat tgactaccca ttatatgaag taaacccttta catttggcct   83880 tctaccagca gagatggaaa accctccaag gaactcttaa gtctagttcc tagataggtg    83940
tgtagtagag ggaaggtctg ggagaacaaa ctgtgatgtg gttggagaga aaatcttcta    84000
aaaaataaga ataaccgtag taaaaaatgc caagacagaa ataaaatgtg gagttgcaat    84060
tatacattta aaaatagat ataatttgga ttataatcat tttcttggtt aacaaggaag     84120
gggaaaaata caaggaatga ctcaggttta tggcaaggat ttctccctga aatggaagtt    84180
tcaccaacta aaacaaatta aatcaagaca aatattggaa cactagaata gagaacatat    84240
gggctagttc tcttaaggaa ataacctata attggaaaat gaaagaagg agggtttaat     84300 atcttaacta caaggaacaa acgtggaagg aatgtattga actagaaaca acaacaaaaa    84360
aagttgcacc taggaataaa taggccagga gtggtagctc attcctgtaa tcccagtacc    84420 ttgggggggct gaggtgggag gatcacttga gcccaggagt tcgagaccag cctgggaaac   84480
ataggaagac cccatctcta caaataattt aaaaattggg tggcatagt ggtatgcacc     84540 tatggtctca gctactcagg aggctgaggc aggaggattg cctgagcccg agaggttgag    84600
gctgtaataa gccatgatca aatcacagca ttccaacctg ggtgatagag caaggcctgg    84660
tctcaaaata taaaaataaa aaattaactg aagtgtgttt atttgacacc atgcgtgaga    84720
acagctatgt gaaaagttaa aaatttactt ggtcacatag cttatgccaa atatccatag    84780
tagcatccta caaaaacctt tttcatattg ggttgtggat agcaaagatt aagatagata    84840
aataaaacag atggattaca ttaaaaactt tatgttaata cgttacagga aacttttgct    84900
```

```
ctttactctt cccacaaatg tgattccaac aaactctagc aggtgcattg atgatgcaa    84960 agcttaatat aactttgttg tgtcctcaaa ttgtttatag cctacaaaag gaaatcagac    85020
atatacataa taaccaattt ttaaaagtga actaaaagtt tacagagtta ctttgatcaa    85080
agtccaggcc tctgcatatg ttcatacaag ttgtgaattc aacacagttc tagatactgg    85140
aatgaatgac atattagaat tgagcacacc caaatacagt tacctatttt tgaaaggaga    85200
gagaaatcac taacaatagg agaaaagctt cactttgtaa gtggtggagg tagcatctgt    85260
actgagcaca tggcgtaaac taagtcagta tagtcccaaa gtagaaactg tgttcaaggg    85320
tcagtttgga cagttggatt ccagtggaag tcacatataa agagttaaat gctgagaaga    85380
aagggtgagc atcggtttga gaaagggttt gaattccagg aatggggctt aaatgccttg    85440
tgtcacataa ggaggtattg ggagaaaatg gtgtaggaaa gatgtgggtg acaatcaaag    85500
ctgaggtgtg agaaaactaa tcgggtgttg gtatggcaag atgtacggga gtggttaact    85560
agagaaattg agtccactta ccaggccagt ctttaaataa gatgtgagag agaatgacaa    85620
ctgaattagc atcagggcca ggaaataaga aagcatagac catttgaaga cattgcagta    85680
aaagaatcaa caaatcctag ttactaatgg gatgtgagac ttggcatcac aggcagaact    85740
caagaatgat ttggagacta tgggacttac cagagtgcgg tggcattaac aggaaatgga    85800
aaatcaggag aagaagctgt tggtaaatat tattgaaact aaccagtggc caaatatgtt    85860
agactggaac ttcagataac agtcaggcct ggaaagaatg atttgcaatt tgagagttat    85920
ctgcaaagaa tcttatttga gaccttgaaa gagaaattgc ttagtcacag aaatggcccc    85980
gtgtggttga tagtaaatag catgggtttg attgtggaga ggttcactaa agaaatacaa    86040
acaaaatttt ggtatatctg agctaagggg gaagaaaata aatcttagaa ttggaataaa    86100
ggacaagctg aagacaagct tggaaattta ggcctcaagg cttggcaatg gttggttacc    86160
aaatagcaag acctgtgatt ctttgctaga tgtttcctaa gactttcaaa gctttgggag    86220
tttggtttct gtagatacat tgtaaagcag atgattagaa aggattaggc ttggattcaa    86280
gccttgactc tttggtgtag aatactagat gaatttatat cagttatcag ttcatgtctt    86340
ttaaaccctg gttttcatg tgtaatgagg gttagtgata aatgtactct tcttatttca    86400
caagggttct tgcaagaacc caggttatca ttataaaat tgtagttttg ttctatggga    86460
aaacaggtgc cagtctttac gtttatttc tttgctaagt gacccgggga caaaaatcaa    86520
aaatagattt ccaatcttct ctacatttaa ttctctctct ctctctttct ttcttgagag    86580
tctttctttc ttaagagtct tgctctgtag cccaggctgg agtgcagtgg cgtgatctca    86640
gctcactgca acctccgcct cctgggttga aggggttttt gtgcctcacc cccagagtag    86700
ctgggactac agatgtgcac taacacaccc agctaatttt tgtattttta gtagagacag    86760
ggtttcacca tgttggccag gctggtctca aactcctgac ttcagatgat ccgcctacct    86820
cagcctctca aagtgctggg attacaggtg tgagccacca tgcctgtcct atatttaatt    86880
ctctatatta agctttgtgt ttccaattat ttatacattt aaaaaataca tccttttgct    86940
ttttgtgatt ccctttttgct ttctaaccat gcttttaaaa tatcttctat atattttgga    87000
tttctgaagt tttatcttag tatctcttaa tttttgttct agatttaatt ctgatttcct    87060
aaatacaggt tgtctagctt ctagagttct ctgcttggta aattgttgta taagacagtt    87120
tttaatatat tacatttaga gagactggaa aaatattgca attcttatta cactatggaa    87180
ttttatggct aatctgtgta atgatctcaa tactttaaaa acagtgatct gtgatgctgg    87240
gttgataaac aaggacaaaa gtagtgaaag agattgagca gagaagacga gaaatgcaaa    87300
```

```
acacatttat ttagagactg ggattgaaga tgggatgata ccatctatat gtattttttt    87360
taagtagaga aggaaataca aatactttac tggaaagttg aaacatctga aagctagtag    87420
attaacacaa gtactgaata actaaaacaa aatatggctt tcatgcttca acaagtacaa    87480
taagctatgc tgaggccaaa cgaactttcc ccagaacttt gttgggatgc ggtgccaaga    87540
ttacagtctt tctttttttg gttggaagta ttgaacgaaa tctttctgct gctatttcct    87600
cagctggaag aaatgattgc tagaacctaa ctagatagtc aagatactag agcggctcag    87660
tggccatgtg aggctattac ttgttggtgg ccattgacca gcttctccac ctgtcttagg    87720
gatctctttc atgctactcc atctatctcc atttctctaa tctccactct ccagacactt    87780
tgttcgtcaa tccttctccc ttcacccctg tttactacct tttataatct gctagagaa    87840 attcaaagct aactaagttg ataattatat tatcacaaac tgagatcatt ggtagaatgt    87900
caggaggtat gaaagtcaca gggtgaaata tttattgagt gtctattaag tgccagacat    87960
tattataaga gtggaggtac agcagtaaaa gagatagaga agctccctgc cctcatggag    88020
cttacatttt aatgggagga catagataat aaacaaaaag taagattgtt tcagataatg    88080
tgttaccaag gagatcatag aaaatgactg atcactgcat ctaagaaaat atttatgaag    88140
ttcttttctg ctatataagt gaagcataca ttgcaaattt gttactcatt ctgtggtcat    88200
atatgatttc ggctattgag attttttaaaa aggcagaagg cagatacacc ataatctctc    88260
ttttcttcct tcctttctag gctggtaaca gttcatgttt gcttcataaa tgaagcagct    88320
ttaaacaaat tcatattctg tctggagtga cagaccacat ctttatctgt tcttgctacc    88380
catgacttta tatggatgat tcagaaattg gaacagaatg ttttactgtg aaactggcac    88440
tgaattaatc atctataaag aagaacttgc atggagcagg actctatttt aaggactgcg    88500
ggacttgggt ctcatttaga acttgcagct gatgttggaa gagaaagcac gtgtctcaga    88560
ctgcatgtac catttgcatg gctccagaaa tgtctaaatg ctgaaaaaac acctagcttt    88620
attcttcaga tacaaactgc agcctgtagt tatcctggtc tctgcaagta gatttcagct    88680
tggatagtga gggtaacaat ttttctcaaa gggatctgga aaaaatgttt aaaactcagt    88740
agtgtcagcc actgtacagt gtagaaagca gtgggaactg tgattggatt tggcaacatg    88800
tcagctttat agttgccgat tagtgatatg ggtctgattt cgatctcttc ctgatgtaaa    88860
ccatgctcac ccatatccca ctatacaaat gcaaatggtt gcctggttcc atttatgcaa    88920
gggagccagt actgaattat gccttggcag aggggagact ccaaaagagt catcgcagga    88980
agaagttaag aacactgaac atcagaacag tctgccaaga aggacattgg catcctggga    89040
aagtccgcct tttcccttga ccactatagg gtgtataaat cgtgtttgca aaatgtgtta    89100
tgatgtgttt atattctaaa actattacag agctatgtaa agggacttag gagaaaatgc    89160
tgaatgtaag atggtcccat ttcaatttcc accatgggag agcctaaaaa taaattatga    89220
catttagtat ctaaggttag aaaaccacgc ccacatgcta atatgggtgt tgaaaactag    89280
gttacttata atgcaaggaa tcaggaaact ttagttattt atagtataat caccattatc    89340
tgtttaaagg atccatttag ttaaaatcgg gcactctata ttcattaagg tttatgaatt    89400
aaaaagaaag ctttatgtag ttatgcatgt cagtttgcta tttaaaatgt gtgacagtgt    89460
ttgtcatatt aagagtgaat ttggcaggaa ttcccaagat ggacattgtg cttttaaact    89520
agaacttgta agacattatg tgaatatccc ttgccaattt tttttataat aagaaaacat    89580
ctgactaaag tcaaagaatg atttcttatg gtttattttg atgaaagttc ttttaacatg    89640
```

```
tcttgaatgt acacataaag gaatccaaag ctttccattc taacttaatc tttgtgataa    89700
cattattgcc atgttctaca accgtaagat gacagttttc aatgtagtga cacaaaaggg    89760
catgaaaaac taactgctag cttttccttc atttcaaaag tccaagaatt tctagtatat    89820 ttggattta gcttctgttc aaagcaaatc cagatgcaac tccagtaagt ggcctttgct     89880
cttttttgta ccaaagagcc cagatgattc ctacagtccc tttcttctct aacatgctgt    89940
ggttccttaa atatgagtaa tttctctaag atataaccca ggtgctttga gaagctgcat    90000
taaggtgttc aggccctcag atatcacatg gtacacttga ttagtaataa aaccagagat    90060
caatttaaat tgctgatagg tcctgtctca gtgtgtggca ttgactgttt tcaggaaaat    90120
agatacagat taatatgagt tatgcgtgta ggttgtgtat agattgagaa gatagatact    90180
tctcaatcta gtagtttgat ttatttaacc aatggtttca gtttgcttga gcatatgaaa    90240
atcctgctta atgtgcttaa gagtataata aatgtgtact tttgtcctca aacctagtag    90300
ctgggtttta acactcatgg acatggtctt aatcaatgga gttaaataaa caaattcagc    90360
aagttattaa atctgacatg gtaggagagg ggagatgtgt cctgcttatt aaatgtgttg    90420
gtccattgaa agttacatgg attgccaatt tttaaaacac taaagttgaa taaaatgcat    90480
gaacaataga aaaatgctga acattatttt ggatgctagc tgcttggaca ttaactgtgt    90540
tatttctgct ttgagatgaa aatatatatt tatctttgct tattttatcc cagatgtgtt    90600
ctgaatatcc ttcttcataa atcatggaaa actcactgct gagatagtaa accatgaaat    90660
cgccttttca gttggtgcca tgtatctgac agttccatct tggaaggttt caaaattacc    90720 tttaaaatg atctcagaag tctgtagatt ctcaatgata ctgaaagctt tgcacctctt     90780
tggtagaaac caggtctatt tagaaaatgg ctttatgata aatgttgcct cctgagtgat    90840
aatgaagtgt tcctggatat tgtattgtaa tttaatgtgc ttaccacact gccacatttt    90900
aatgagtcag agaaaaatta attttcttc aatacaataa tagaacaagt agcctattct     90960
cttaaaaagt atgtgaaaag aaaattatga aaaaatatgc ataacctaatg aagtattggt    91020 tttagtaaga attaaataca tttcattgag ctttaaagta ctttggagaa actttggggc    91080
acgttttcct actctaattc aactaaagtt ataaataaag agaaaaactc attcagaaat    91140
catggatttt aaaaatattt tactgcagcc aagttttcat ttcaaaatgt aatttcagtt    91200
tggagctttt aggcattatg tatatttaaa aaatatattc ttcaaaaatg cattttggca    91260
tggtgggatg gatgttgcaa aagatatccg gagcctccag tctgtcatta actgatatgg    91320
taaatcacct ctcttctttg ggtctcaatt tttatttat ctatatggta aactcagaga     91380
tcactcctta ggggtgagtc ctattgcaat atgaccgaca agaagacaa aatagcattg     91440 aaactaaccc atacaaaata tccaactctg gattctgtga ataagtatct tgaccataaa    91500
aagtcattgc tgttcttgtt tctaatgtaa atagtgtcca ttagtaaaag tgaaattcag    91560
tcttaagtag ggtgaattgg atcaccattt acacaagaga tggcttttttc ctttgcttga   91620 ataaacattt tggatcacct ccaaagaatg aaaaccagta gtacgtttta gtcatattag    91680
tcaggatgag aaactataag atgtgtgtaa catttggaaa tgcaccaaag tgagcgttta    91740
aatcttctca ttttattgaa aactaagagc agaaaatgta aatgctcat gaaggttttg     91800 aatgccaaaa gatatttag aatcaattta taaaggggta attcattaat tacacttaa      91860 aattggaaag tgggataaga aatctaaagt aaaccagctt atctttgaaa caatattatt    91920
ttgaaattgg ctttaaaata aaaccattca gattgaaatt ctaattagct catttgtgga    91980
gtttgatcac acaattcata atgttgctgc tttccattaa ctagtcttga aatgcctttg    92040
```

```
tttgtaaaaa taaaataatg gtactttcat tttataacaa ggtgttttt tcaagaaata    92100
atccatgcta aaatggatat ttgtgatcct gaaatgttta ctaagcattg taaatttatt    92160
tataactgcc atctccaact acatccttat gatgttttta acaataaaat taaaacaact    92220
gttaaactaa aaaccacacc gttttccagt acttgatctc tgagctacaa tactcactaa    92280
atataatttt ccaatcaaaa tattctattc tatattctaa gggttaatat gtgattatag    92340
tgtccacttg ccaccatttt tttaaatcaa tggacttgaa aagtattaat ttagatggat    92400
gcgcagatat accctcagtt cagtcataga ttggagtttg catataataa tgtaaatgta    92460
tgtcgacact attctaaata gttctattat gactgaaatt taattaaata aaaaaggttg    92520
taaaatgtga tgtgtatgtg tatatactgt atgtgtactt tttaaaatag gtgtatgtcc    92580
caacccttt ttatacaggt ttgaatttaa aattacatga tatatacata tactttattg    92640
ttctaaataa agaattttat gcactctcat aaatttaccc tgtcatttta tatcttaagg    92700
ttatcacata tgtctacaac atggttgaac atttattaag ctacagtcaa aattttctgt    92760
ggaaactttt gtcattaatc tagattttat taagctacag tcaaaatttt ctatggaaac    92820
ttttgtcatt aatctagatt tgttgaaat atggacacaa ggggataaga aattatttaa    92880
attcaataaa tatttattga ttactaaaat aagtaatcaa ggaaaataaa aatgaatta    92940
acacgacgtt tgctttcaag agatttataa cttgtctgga gaaagaaat gcaatagata    93000
tatagaaaag cactataata gatatagata cagaaaatag atacagatat agaaaagcag    93060
tataatatgt atagtccctg aagtaaaatac ctacatgcaa aacagaggtc cagttaatgt    93120
gcttagggca tgcaggaagg agaaatggat acagaataag ggagactgtg gaggaattga    93180
tgtttgggct aatacttaga aggatgagac aaatttttat agtgagaatt atgcccagtc    93240
agggcagcat tttccataga aagaagttat aaaatttcta agcttatttt accaactcaa    93300
acaggtatgt ccttagcata caccaaataa aaagacacac ggagagataa gaccagaccc    93360
ttcaatgtaa cagtgagtgc agacactatt cttagggtcc ctgagaagcc tagactcctt    93420
tgcttgtttc tgagaagagg aatgacgaga tcaaaacgca ctacggatcc tgtgatttag    93480
gcagtagata atcatcctgc ttaaccactg gttgctattt gactctcaag cacataccct    93540
tgctatatga caccacactt attcacccac catttctttt cagaatttgc tgattctctc    93600
tcctctgttt acctttata ttgccaactt cgaccaatat atgactagat aactagaata    93660
gcctcctaac tgatcacatg attctacttt caccctttt caatcagttc atcacattat    93720
agtcaataat agggagacat ctggtgtgtg tgtgtgtgtg tatgtgtgtg tgtgtgtgtg    93780
tgtgtgtgtg tgtgtttctg gctaaaacac ttggatggct tctcattatt ttttagctaa    93840
agcccaaact cttcaacaca gcctacaagg ctctacttga gccatctcat cttttttgtt    93900
ttgttttgtt ttggattgct gattgttttt gcctttaatc cataaacaac atgaaggttg    93960
ggcccataaa tactaatata actgcagtcc taaaatttag tgcaaattat tagtggaatt    94020
gaaacaaaat gtgatctaaa tagctatcac ctgttgtact gagaagttat ttttttaagat    94080
ttttattatg gacaatttga aatatatgca aaagtcgata agatagtgta ataaattcat    94140
ataaccataa ccctacttca accttactca actcctgaat aatcttgttt tatctaaact    94200
ccctatccac tccccatttt gtatcatttt caggaaagta cttaaaagta tttgatctgg    94260
aaacatttct atgtatatct ctgttaactt tcagaaagcg taaccctgat acccttgtta    94320
tacctaagaa aagttattaa caatttctta ataccaagga gccaacaagt atttacattt    94380
```

```
taactcttttt acactgtaca ctgcagtatt gcactagagt agggtataaa atacagttaa    94440
aagtccccct tgaacattaa agttagtttc cctggaggta aacactgcta attattcctc    94500
attaacttct agaattttt ggcatgtaca aactatatat acatgtatat acaatactag    94560
tctctaactt tatctctttc atttattagg agaacgcaga acactacatc agcctagata    94620
aatctttacc cactgcacca taataaccag gaaattatag ataggcatta cga          94673
```

<210> SEQ ID NO 8
<211> LENGTH: 11
<212> TYPE: PRT
<213> ORGANISM: Homo sapiens

<400> SEQUENCE: 8

Glu Gly Ile Cys Arg Asn Arg Val Thr Asn Asn
1               5                   10